US007659097B2

(12) United States Patent
Renninger et al.

(10) Patent No.: US 7,659,097 B2
(45) Date of Patent: Feb. 9, 2010

(54) PRODUCTION OF ISOPRENOIDS

(75) Inventors: Neil Stephen Renninger, Oakland, CA (US); Jack Newman, Berkeley, CA (US); Keith Kinkead Reiling, Oakland, CA (US); Rika Regentin, Hayward, CA (US); Christopher John Paddon, Pacifica, CA (US)

(73) Assignee: Amyris Biotechnologies, Inc., Emeryville, CA (US)

( * ) Notice: Subject to any disclaimer, the term of this patent is extended or adjusted under 35 U.S.C. 154(b) by 213 days.

(21) Appl. No.: 11/754,235

(22) Filed: May 25, 2007

(65) Prior Publication Data
US 2008/0274523 A1 Nov. 6, 2008

Related U.S. Application Data

(60) Provisional application No. 60/808,989, filed on May 26, 2006, provisional application No. 60/870,592, filed on Dec. 18, 2006.

(51) Int. Cl.
C12P 7/04 (2006.01)
C12P 5/00 (2006.01)
C12P 23/00 (2006.01)
C12N 9/02 (2006.01)
C12N 15/82 (2006.01)
C12N 15/64 (2006.01)
C12N 1/20 (2006.01)

(52) U.S. Cl. ........................ 435/157; 435/155; 435/166; 435/167; 435/67; 435/128; 435/189; 435/252.3; 435/252.8; 435/466; 435/69.1; 435/91.4; 435/170; 435/320.1

(58) Field of Classification Search .................. None
See application file for complete search history.

(56) References Cited

U.S. PATENT DOCUMENTS

| 4,500,707 | A | 2/1985 | Caruthers et al. |
| 5,436,327 | A | 7/1995 | Southern et al. |
| 5,460,949 | A | 10/1995 | Saunders et al. |
| 5,599,711 | A | 2/1997 | Flen et al. |
| 5,700,637 | A | 12/1997 | Southern |
| 6,352,840 | B1 | 3/2002 | Gwynn et al. |
| 6,989,257 | B2 | 1/2006 | Berry et al. |
| 7,192,751 | B2 | 3/2007 | Keasling et al. |
| 2003/0148416 | A1 | 8/2003 | Berry et al. |
| 2003/0148479 | A1 | 8/2003 | Keasling et al. |
| 2004/0005678 | A1 | 1/2004 | Keasling et al. |
| 2004/0029239 | A1 | 2/2004 | Ohto et al. |
| 2004/0063182 | A1 | 4/2004 | Ohto et al. |
| 2004/0131637 | A1 | 7/2004 | Chatfield |
| 2005/0084972 | A1 | 4/2005 | Barr et al. |
| 2005/0266518 | A1 | 12/2005 | Berry et al. |
| 2005/0287655 | A1 | 12/2005 | Tabata et al. |
| 2006/0121558 | A1 | 6/2006 | Stephanopoulos et al. |

FOREIGN PATENT DOCUMENTS

| WO | WO 96/17951 A2 | 6/1996 |
| WO | WO 96/17951 A3 | 10/1996 |
| WO | WO 2005/033287 A2 | 4/2005 |
| WO | WO 2005/033287 A3 | 4/2005 |
| WO | WO 2006/014837 A1 | 2/2006 |
| WO | WO 2007/005604 A2 | 1/2007 |

OTHER PUBLICATIONS

Kisselev L., Polypeptide release factors in prokaryotes and eukaryotes: same function, different structure. Structure, 2002, vol. 10: 8-9.*
Wishart et al., A single mutation converts a novel phosphotyrosine binding domain into a dual-specificity phosphatase. J. Biol. Chem., 1995, vol. 270(45): 26782-26785.*
Witkowski eta l., Conversion of b-ketoacyl synthase to a Malonyl Decarboxylase by replacement of the active cysteine with glutamine. Biochemistry, 1999, vol. 38: 11643-11650.*
Broun et al., Catalytic plasticity of fatty acid modification enzymes underlying chemical diversity of plant lipids. Science, 1998, vol. 282: 1315-1317.*
Seffernick et al., Melamine deaminase and Atrazine chlorohydrolase: 98 percent identical but functionally different. J. Bacteriol.,2001, vol. 183 (8): 2405-2410.*
Alpuche-Aranda, et al. *Salmonella typhimurium* activates virulence gene transcription within acidified macrophage phagosomes. Proc. Natl. Acad. Sci. U.S.A. 1992; 89(21):10079-10083.
Amann, et al. ATG vectors for regulated high-level expression of cloned genes in *Escherichia coli*. Gene. 1985; 40: 183-190.
Amann, et al. Tightly regulated tac promoter vectors useful for the expression of unfused and fused proteins in *Escherichia coli*. Gene. 1988; 69:301-315.
Bennetzen, et al. Codon selection in yeast. J. Biol. Chem. 1982; 257(6):3026-3031.
Bitter, et al. Expression and secretion vectors for yeast. Methods in Enzymology. 1987; 153:516-544.
Bochar, et al. Sequence comparisons reveal two classes of 3-hydroxy-3- methylglutaryl coenzyme A reductase. Mol Genet Metab. Feb. 1999; 66(2):122-7.
Bruschi, et al. Introduction of nonselectible 2 mu plasmid into [cir(o)] cells of the yeast *S. cerevisiae* by DNA transformation and in vivo site-specific resolution. Curr. Genet. 1989; 15: 83-90.

(Continued)

Primary Examiner—Ganapathirama Raghu
(74) Attorney, Agent, or Firm—Wilson Sonsini Goodrich & Rosati

(57) ABSTRACT

The present invention provides methods for a robust production of isoprenoids via one or more biosynthetic pathways. The invention also provides nucleic acids, enzymes, expression vectors, and genetically modified host cells for carrying out the subject methods. The invention also provides fermentation methods for high productivity of isoprenoids from genetically modified host cells.

41 Claims, 20 Drawing Sheets

OTHER PUBLICATIONS

Chatfield, et al. Use of the *nirB* Promoter to Direct the Stable Expression of Heterologous Antigens in *Salmonella* Oral Vaccine Strains: Development of a Single—Dose Oral Tetanus Vaccine Biotechnol. 1992; 10:888-892.

Christainson, et al. Multifunctional yeast high-copy-number shuttle vectors. Gene. 1992; 110:119-122.

Deboer, et al. The tac promoter: a functional hybrid derived from the trp and lac promoters. Pro. Natl. Acad. Sci. U.S.A. 1983; 80:21-25.

Dunstan, et al. Use of in vivo-regulated promoters to deliver antigens from attenuated *Salmonella enterica* var. *typhimurium*. Infect. Immun. 1999; 67:5133-5141.

Erhanrt, et al. The presence of a defective LEU2 gene on 2 mu DNA recombinant plasmids of *Saccharomyces cerevisiae* is responsible for curing and high copy number. J. Bacteriol. 1983; 156(2):625-635.

Erhart, et al. The presence of a defective LEU2 gene on 2 mu DNA recombinant plasmids of *Saccharomyces cerevisiae* is responsible for curing and high copy number. J. Bacteriol. 1983; 156: 625-635.

Eyre-Walker. Synonymous codon bias is related to gene length in *Escherichia coli*: selection for translational accuracy? Mol. Biol. Evol. 1996: 13(6): 864-872.

Farmer, et al. Precursor balancing for metabolic engineering of lycopene production in *Escherichia coli*. Biotechnol. Prog. 2001; 17:57-61.

Geiser, et al. Integration of PCR fragments at any specific site within cloning vectors without the use of restriction enzymes and DNA ligase. BioTechniques. 2001; 31:88-92.

Gouy, et al. Codon usage in bacteria: correlation with gene expressivity. Nucleic Acids Res. 1982: 10(22): 7055-7074.

Guzman, et al. Tight regulation, modulation, and high-level expression by vectors containing the arabinose PBAD promoter. J. Bacteriol. 1995; 177:4121-4130.

Harborne, et al. Transcriptional control, translation and function of the products of the five open reading frames of the *Escherichia coli* nir operon. Mol. Micro. 1992; 6:2805-2813.

Hedl, et al. Class II 3-hydroxy-3-methylglutaryl coenzyme A reductases. J Bacteriol. 2004; 186(7):1927-32.

Hillen, et al. In Saenger W. and Heinemann U. (eds). Topics in Molecular and Structural Biology, Protein-Nucleic Acid Interaction. 1989; 10: 143-163.

Hoffmann, et al. Heat-inactivation of plasmid-encoded CI857 repressor induces gene expression from Ind- lambda prophage in recombinant *Escherichia coli*. FEMS Microbiol Lett. 1999; 177(2): 327-334.

Kajiwara, et al. Expression of an exogenous isopentenyl diphosphate isomerase gene enhances isoprenoid biosynthesis in *Escherichia coli*. Biochem. J. 1997; 324:421-426.

Kim, et al. A xylose-inducible *Bacillus subtilis* integration vector and its application. Gene. 1996; 181:71-76.

Kim, et al. Metabolic engineering of the nonmevalonate isopentenyl diphosphate synthesis pathway in *Escherichia coli* enhances lycopene production. Biotechnol. Bioeng. 2001; 72:408-415.

Korz, et al. Simple fed-batch technique for high cell density cultivation of *Escherichia coli*. J Biotechnol. 1995; 39(1):59-65.

Kovach, et al. Four new derivatives of the broad-host-range cloning vector pBBR1MCS, carrying different antibiotic-resistance cassettes. Gene. 1995; 166(1): 175-176.

Lange, et al. Isoprenoid biosynthesis: the evolution of two ancient and distinct pathways across genomes. Proc. Natl. Acad. Sci. USA. 2000; 97(24): 13172-13177.

Lee. High cell-density culture of *Escherichia coli*. Trends Biotechnol. 1996; 14(3):98-105. Review.

Longtine, et al. Additional modules for versatile and economical PCR-based gene deletion and modification in *Saccharomyces cerevisiae*. Yeast. 1998; 14:953.

Looman, et al. Influence of the three nucleotides upstream of the initiation codon on expression of the *Escherichia coli* lacZ gene in *Saccharomyces cerevisiae*. Nuc. Acid. Res. 1993; 21:4268-4271.

Lutz, et al. Independent and tight regulation of transcriptional units in *Escherichia coli* via the LacR/O, the TetR/O and AraC/I1-I2 regulatory elements. Nucl Acids Res. 1997; 25:1203-1210.

Matteucci, et al. The Synthesis of Oligodeoxypyrimidines on a Polymer Support Tet. Lett. 1980; 21:719-722.

McKelvie, et al. Expression of heterologous antigens in *Salmonella typhimurium* vaccine vectors using the in vivo-inducible, SPI-2 promoter, ssaG. Vaccine. 2004; 22: 3243-3255.

Melton, et al. Efficient in vitro synthesis of biologically active RNA and RNA hybridization probes from plasmids containing a bacteriophage SP6 promoter. Nucl. Acids. Res. 1984; 12:7035-7056.

Merke, et al. Molecular cloning, expression, and characterization of amorpha-4, 11-diene synthase, a key enzyme of artemisinin biosynthesis in Artemisia annua L. Arch. Biochem. Biophys. 2000; 381:173-180.

Meyer, et al. Molecular vehicle properties of the broad host range plasmid RK2. Science. 1975; 190:1226-1228.

Mumberg, et al. Regulatable promoters of *Saccharomyces cerevisiae*: comparison of transcriptional activity and their use for heterologous expression. Nucl. Acids. Res. 1994; 22(25): 5767-5768.

Nakamura, et al. Codon usage tabulated from international DNA sequence databases: status for the year 2000. Nucleic Acids Res. 2000; 28(1):292.

Okkels. A URA3-promoter deletion in a pYES vector increases the expression level of a fungal lipase in *Saccharomyces cerevisiae*. Annals of the New York Academy of Sciences. 1996; 782(1):202-207.

Pansegrau, et al. Complete nucleotide sequence of Birmingham IncP alpha plasmids. Compilation and comparative analysis. J. Mol. Biol. 1994; 239:623-663.

Pechous, et al. Cloning and functional expression of an (E, E)-alpha-farnesene synthase cDNA from peel tissue of apple fruit. Planta. 2004; 219(1):84-94.

Picaud, et al. Expression, purification and characterization of recombinant (E)-beta-farnesene synthase from Artemisia annua. Phytochemistry. 2005; 66(9): 961-967.

Pirt. Principles of microbe and cell cultivation. John Wiley & Son. New York. 1975. pp. 4-14; 81-146.

Pulkkinen, et al. A *Salmonella typhimurium* virulence protein is similar to a *Yersinia enterocolitica* invasion protein and a *Bacteriophage lambda* outer membrane protein. J. Bacteriol. 1991; 173(1):86-93.

Ro, et al. Production of the antimalarial drug precursor artemisinic acid in engineered yeast. Nature. 2006; 440:940-943.

Roberts, et al. Genetic characterization of the stabilizing functions of a region of broad-host-range plasmid RK2. J. Bacteriol. 1990; 172(11):6204-6216.

Rohdich, et al. Studies on the nonmevalonate terpene biosynthetic pathway: metabolic role of IspH (LytB) protein. Proc. Natl. Acad. Sci. USA 2002; 99:1158-1163.

Rohmer, et al. Isoprenoid biosynthesis in bacteria: a novel pathway for the early steps leading to isopentenyl diphosphate. Biochem. 1993; 295:517-524.

Schiestl, et al. High efficiency transformation of intact yeast cells using single stranded nucleic acids as a carrier. Curr. Genet. 1989; 16:339.

Shetron-Rama, et al. Intracellular induction of Listeria monocytogenes actA expression. Infect. Immun. 2002; 70:1087-1096.

Sia, et al. Different relative importances of the par operons and the effect of conjugal transfer on the maintenance of intact promiscuous plasmid RK2. J. Bacteriol. 1995; 177:2789-2797.

Sikorski, et al. A system of shuttle vectors and yeast host strains designed for efficient manipulation of DNA in *Saccharomyces cerevisiae*. Genetics. 1989; 122:19-27.

Song. A soluble form of phosphatase in *Saccharomyces cerevisiae* capable of converting farnesyl diphosphate into E,E-farnesol. Applied Biochemistry and Biotechnology. 2006; 128:149-158.

Valdivia, et al. Bacterial genetics by flow cytometry: rapid isolation of *Salmonella typhimurium* acid-inducible promoters by differential fluorescence induction. Mol. Microbiol. 1996; 22:367-378.

Van Dijken, et al. An interlaboratory comparison of physiological and genetic properties of four *Saccharomyces cerevisiae* strains. Enzyme microb technol. 2000; 26:706.

West, et al. *Saccharomyces cerevisiae* GAL1-GAL10 divergent promoter region: location and function of the upstream activating sequence UASG. Mol. Cell. Biol. 1984; 4(11):2467-2478.

Yun, et al. mRNA sequences influencing translation and the selection of AUG initiator codons in the yeast *Saccharomyces cerevisiae*. Mol. Microbiol. 1996; 19:1225-1239.

Shiba, et al. U.S. Appl. No. 60/709,605, entitled "Genetically Modified Host Cells And Use Of Same For Producing Isoprenoid Compounds", filed Aug. 19, 2005.

Shiba, et al. U.S. Appl. No. 60/759,674 entitled "Genetically Modified Host Cells And Use Of Same For Producing Isoprenoid Compounds", filed Jan. 17, 2006.

Jackson, et al Metabolic engineering to produce sesquiterpenes in yeast. Org Lett. 2003; 5(10):1629-32.

Martin, et al. Engineering a mevalonate pathway in *Escherichia coli* for production of terpenoids. Nat Biotechnol. 2003; 21(7):796-802.

Tabata, et al. Production of mevalonate by a metabolically-engineered *Escherichia coli*. Biotechnol Lett. 2004; 26(19):1487-91.

Whisstock, et al. Prediction of protein function from protein sequence and structure. Q Rev Biophys. Aug. 2003;36(3):307-40.

* cited by examiner

Figure 10A-B
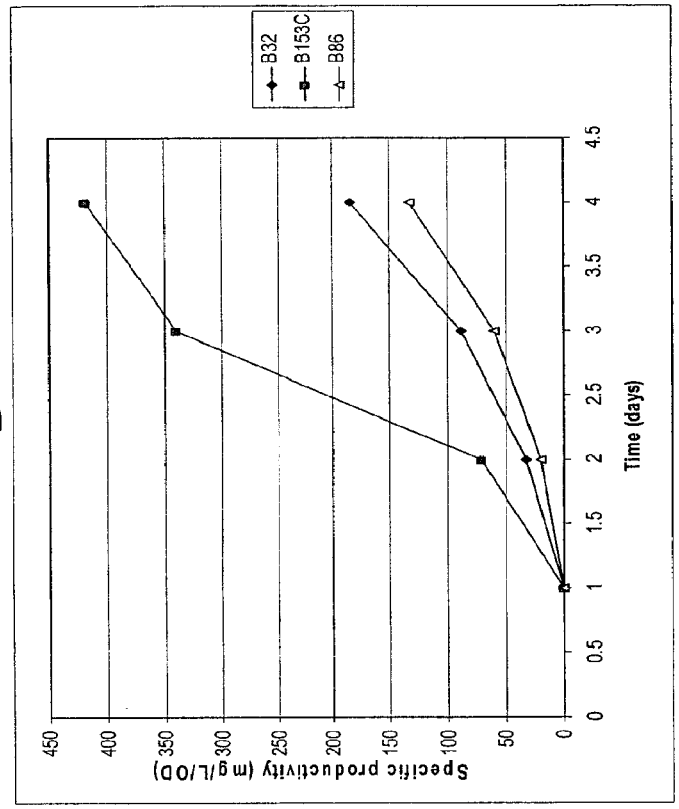
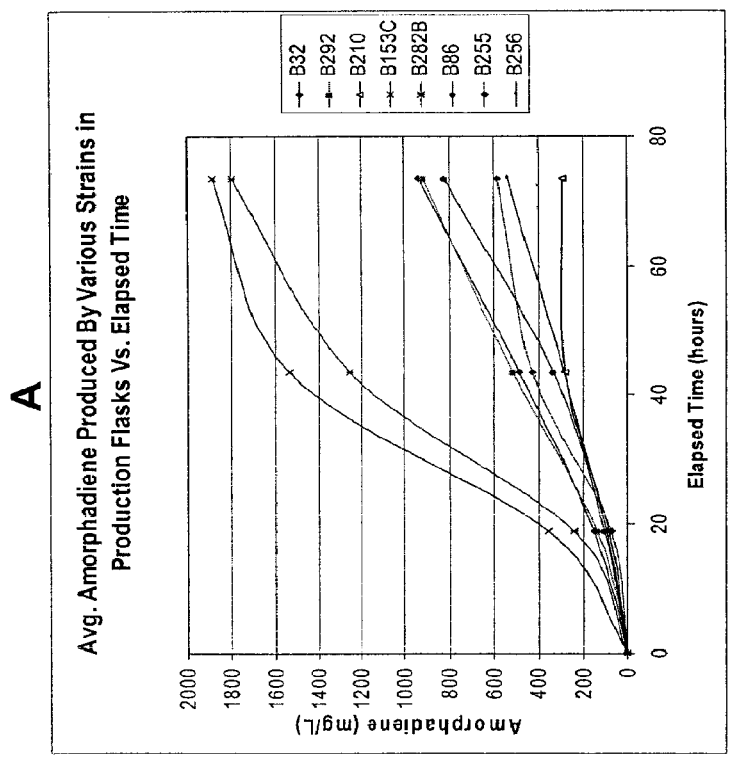

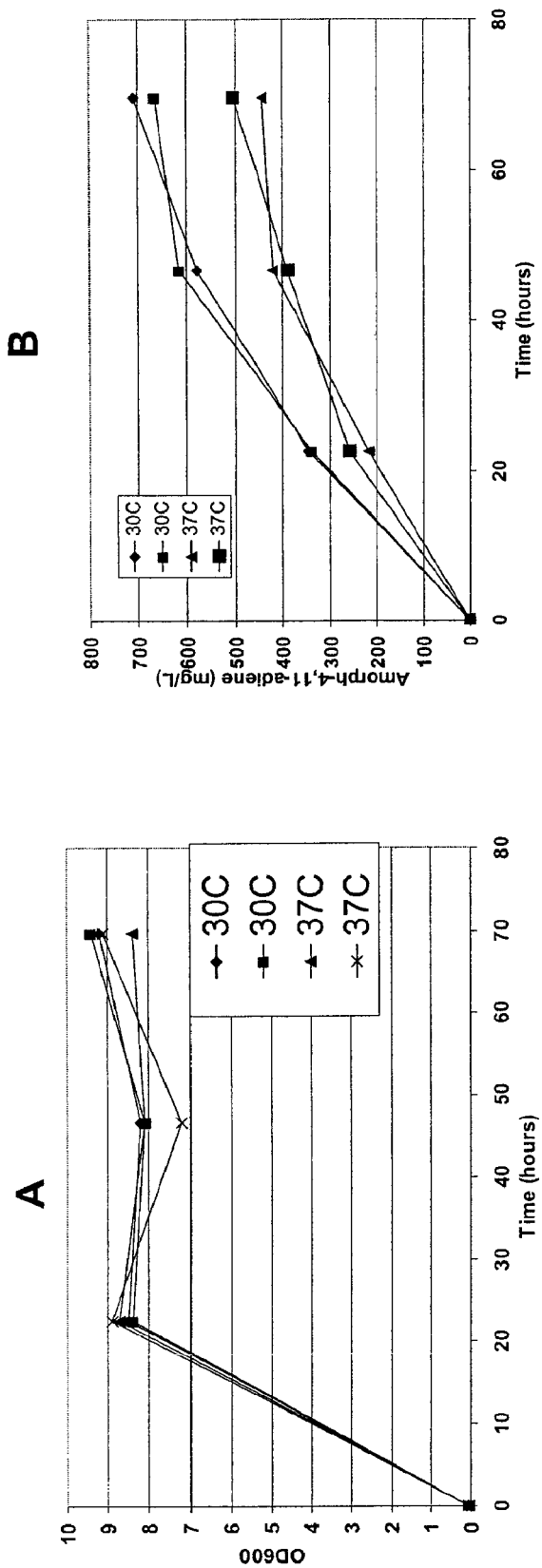
Figure 11A-B

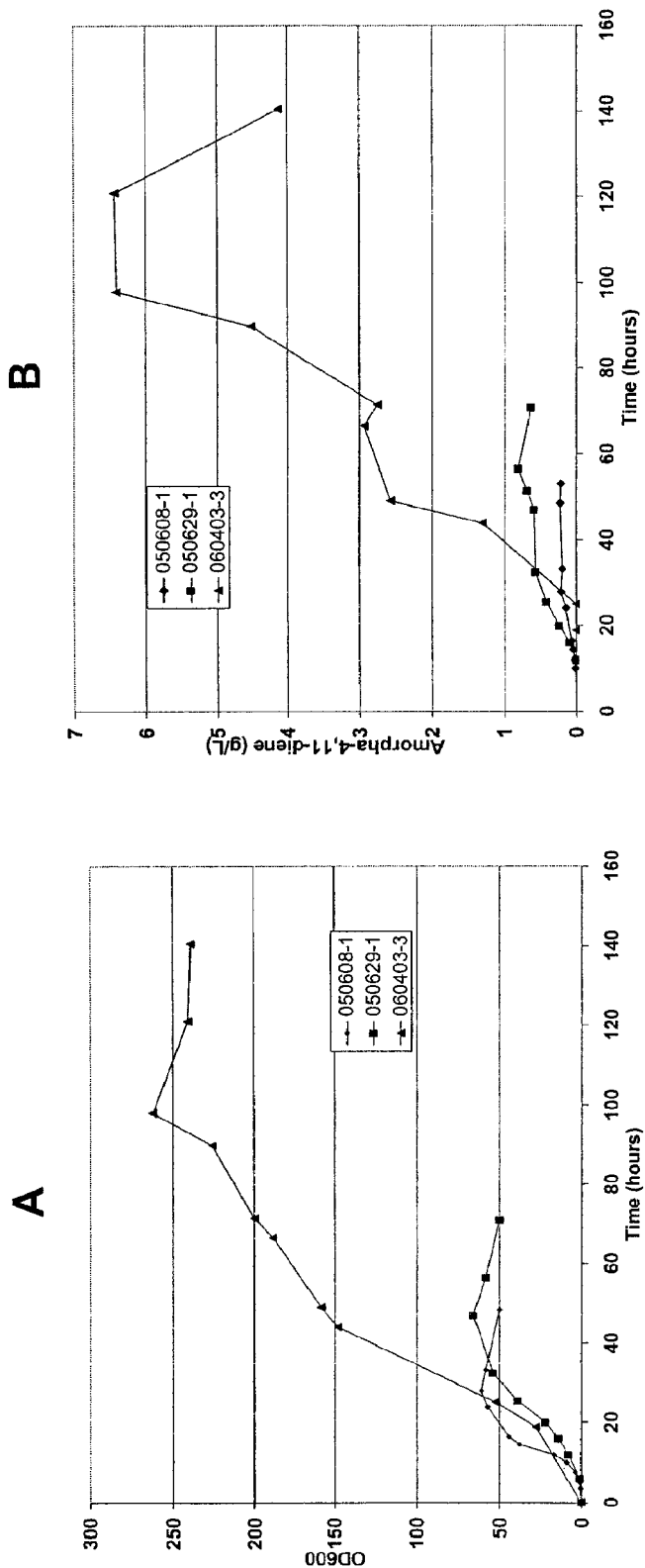
Figure 12A-B

Figure 12C-D
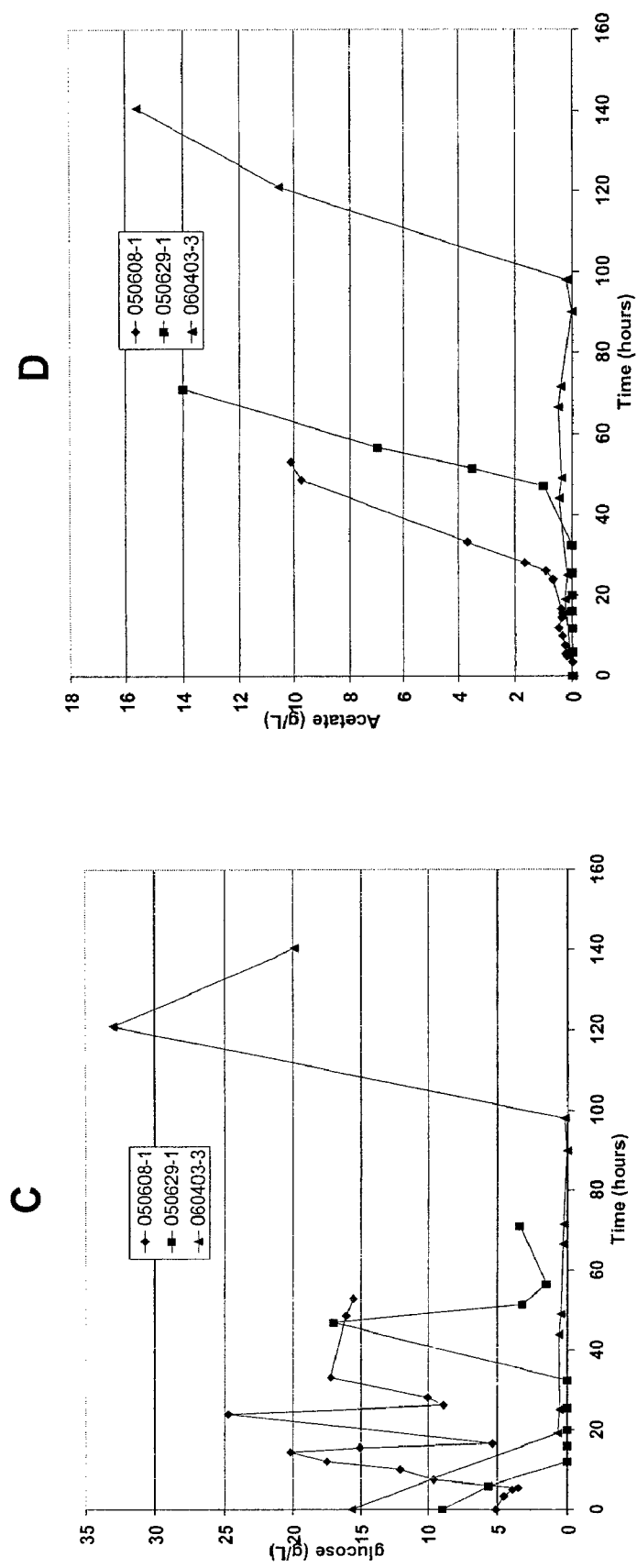

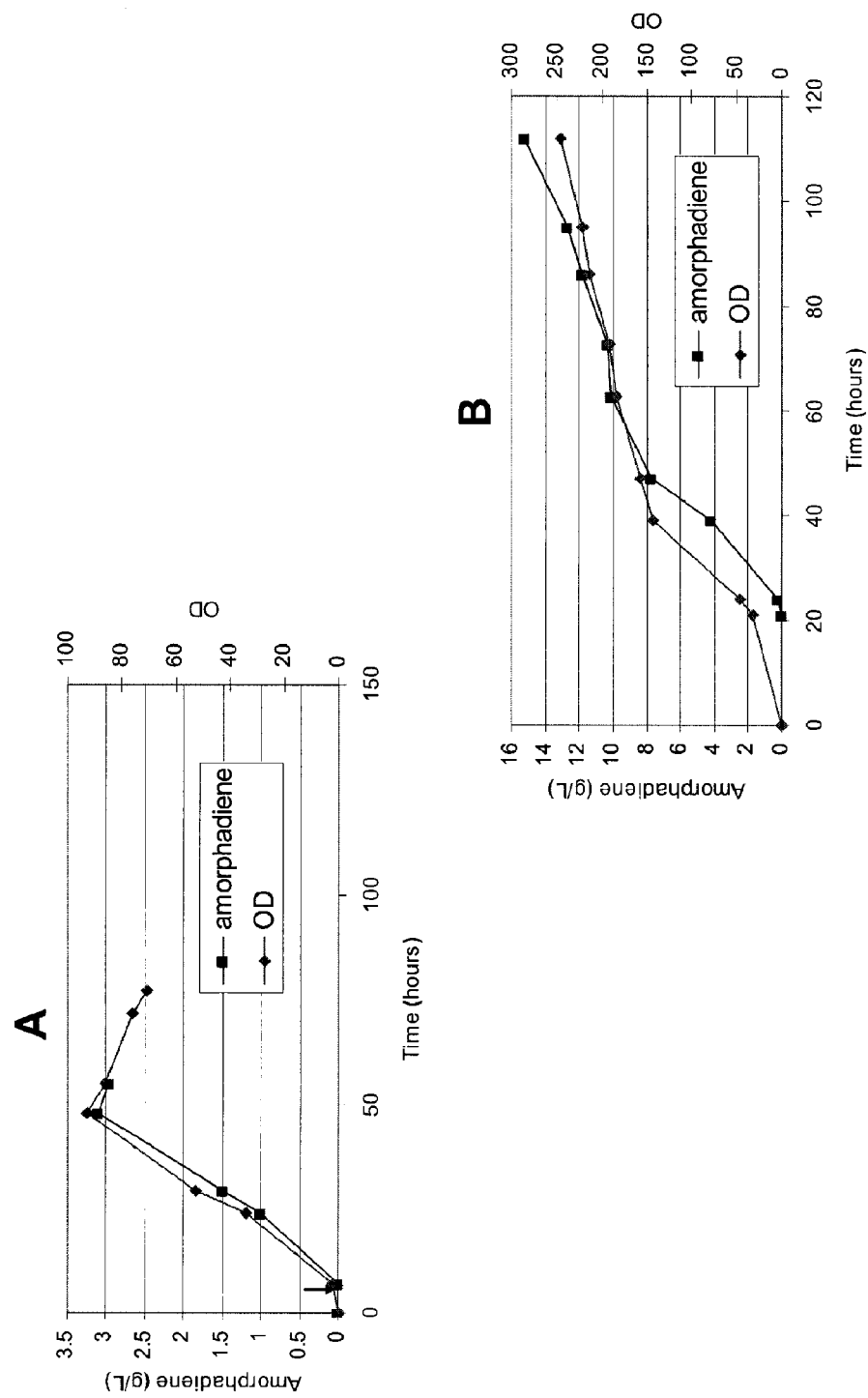
Figure 13A-B

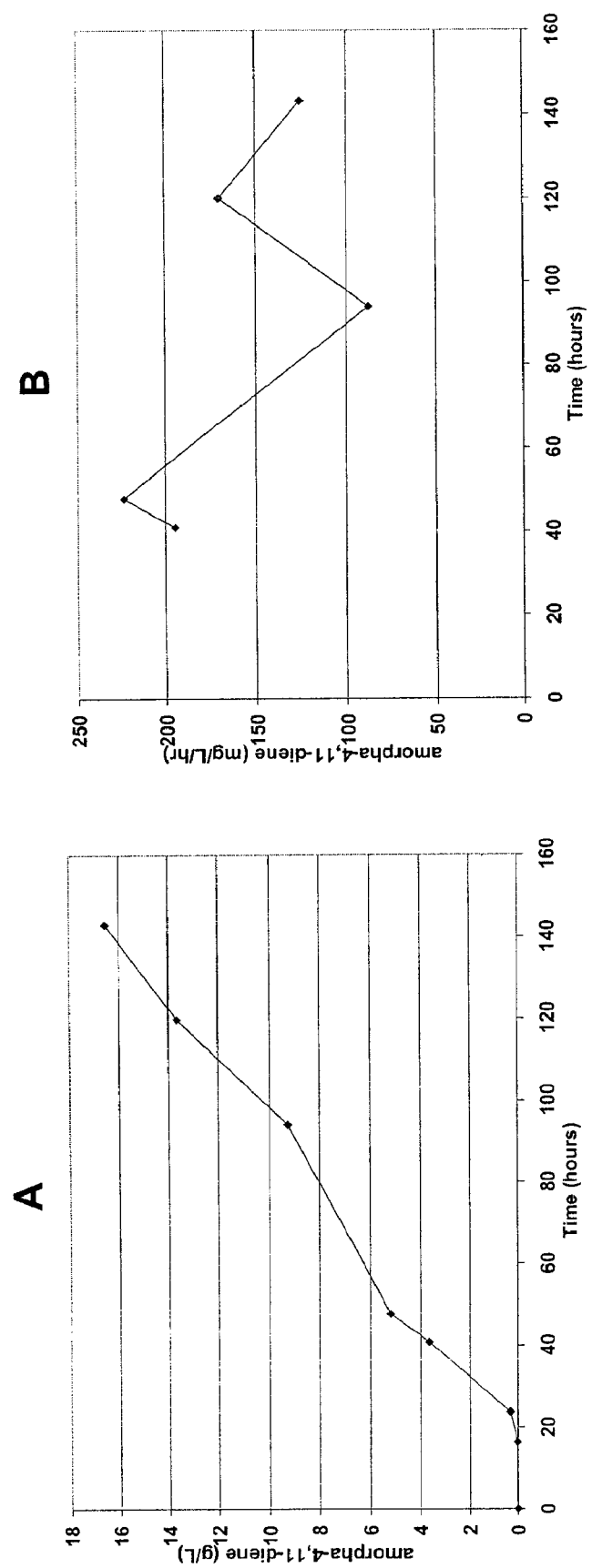
Figure 14A-B

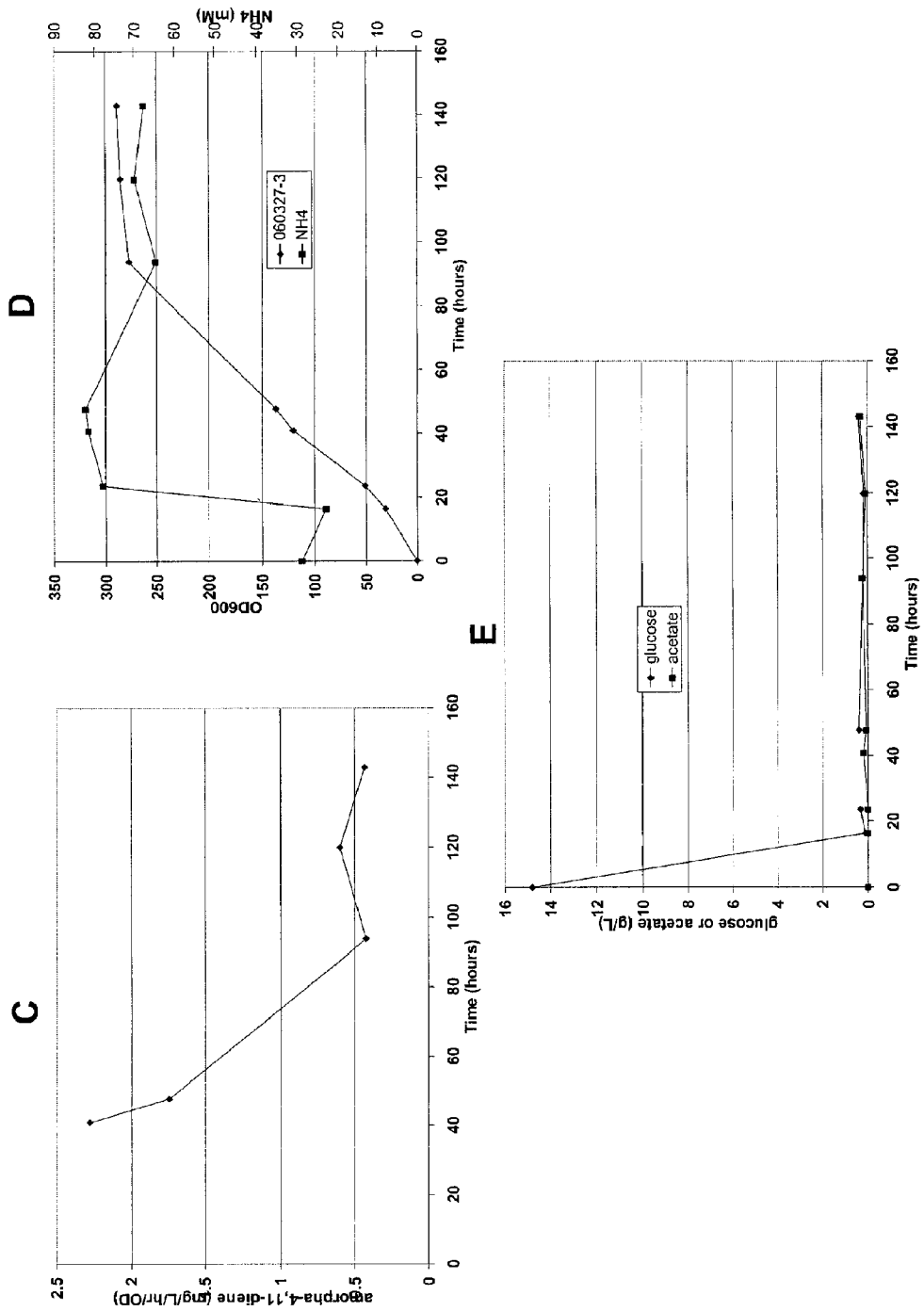
Figure 14C-E

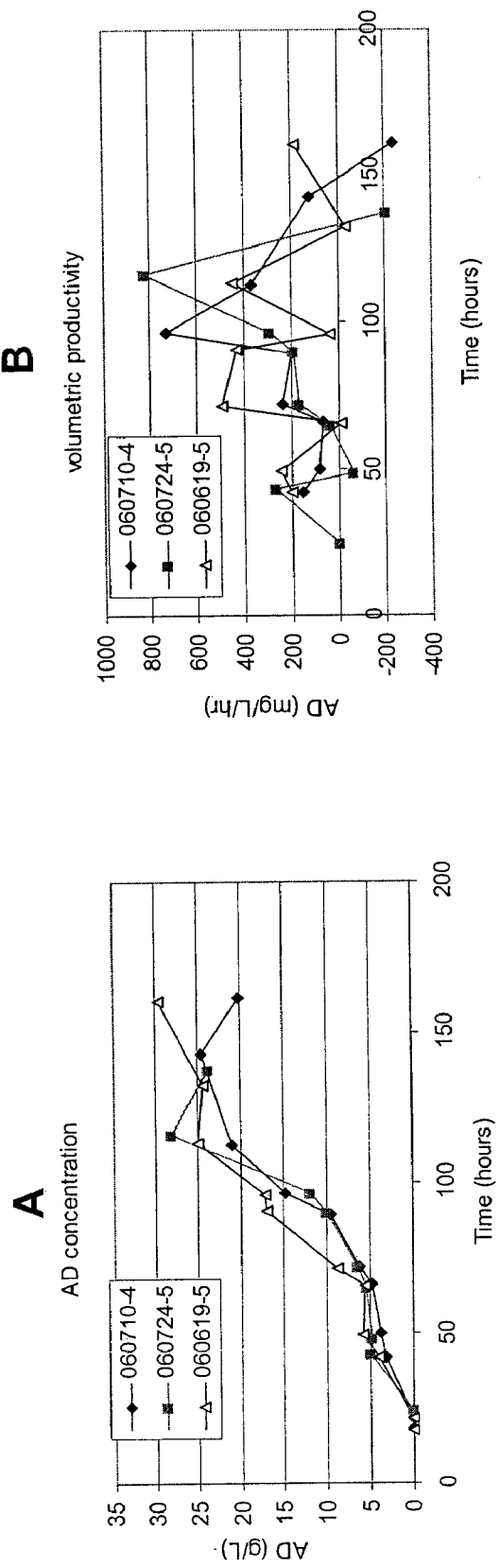
Figure 15A-B

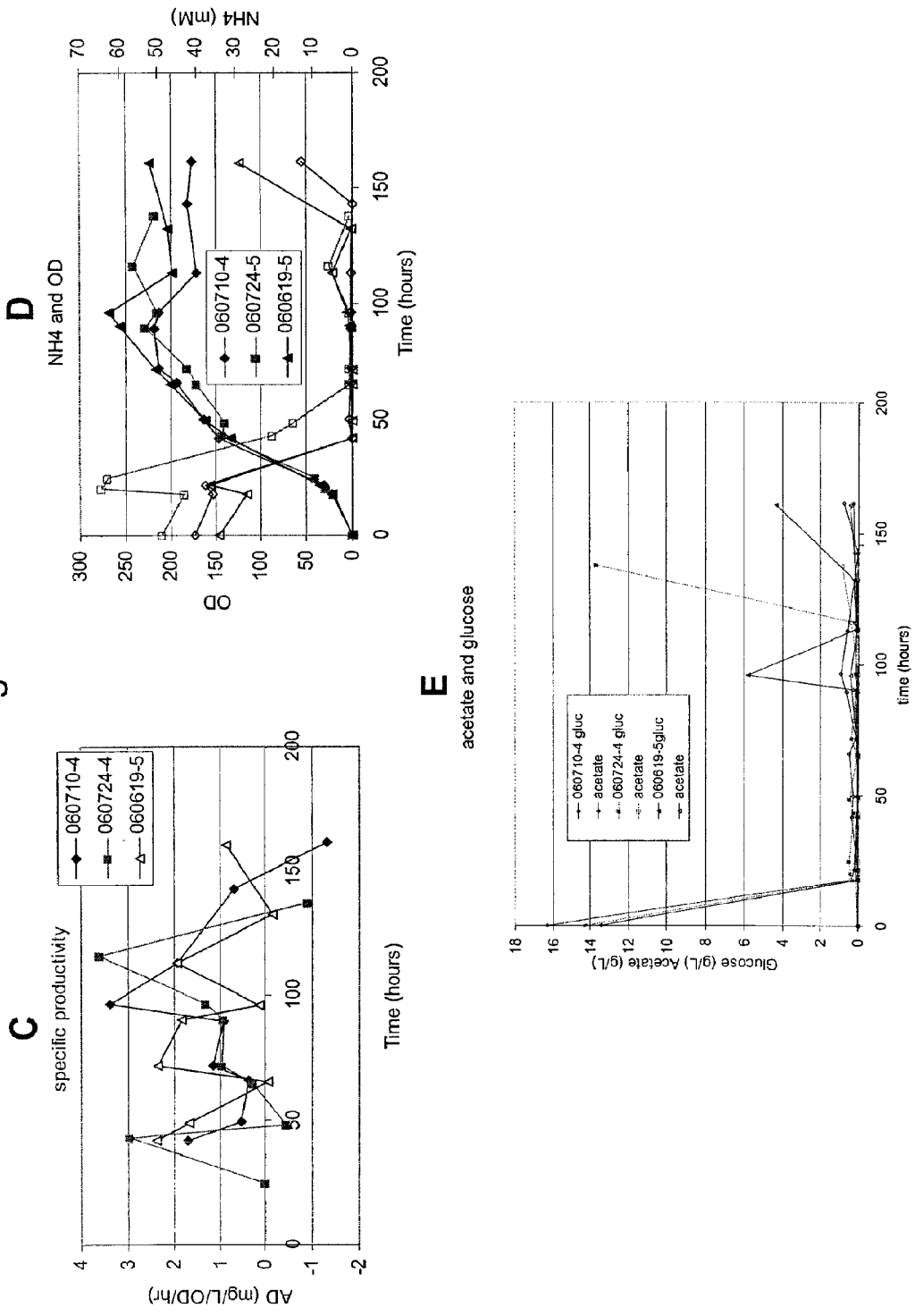
Figure 15C-E

SEQUENCE LISTING

<160> NUMBER OF SEQ ID NOS: 54

<210> SEQ ID NO 1
<211> LENGTH: 4247
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gaattcaaag gaggaaaata aaatgaagaa ctgtgtgatt gtttctgcgg tccgcacggc      60
gatcggcagc tttaacggct ctttagcgag cacctctgca atcgatctgg gtgcgacggt     120
cattaaggcc gccattgaac gcgccaaaat cgacagccag cacgttgatg aggtgatcat     180
gggcaatgtg ttacaagccg gcctgggtca aaacccagcg cgtcaagcac tgttaaaatc     240
tggtctggcc gagaccgtgt gtggcttcac cgtcaataag gtttgcggct ctggcctgaa     300
gagcgtggcc ctggcagcac aagcgattca agccggtcag gcacaaagca tcgttgcggg     360
tggcatggag aacatgtctc tggcgccgta cttattagat gccaaagccc gcagcggtta     420
tcgcctgggc gatggtcagg tgtacgacgt catcttacgc gatggcttaa tgtgcgcgac     480
ccacggttac cacatgggta ttacggccga aaacgtggcg aaagaatacg gcattacgcg     540
cgagatgcag gatgaattag cactgcactc tcagcgcaaa gcagcagccg cgatcgagtc     600
tggtgcgttt acggcggaaa tcgtgccagt taacgtggtc acgcgcaaga agacgttcgt     660
```

-continued

```
tttcagccag gacgagttcc cgaaggcaaa cagcaccgcg gaggccttag gtgccttacg       720
cccagccttt gacaaagcgg gcacggtcac cgccggtaat gcgagcggca tcaatgatgg       780
tgcagcggca ctggtcatca tggaagagag cgccgcatta gcagcgggtc tgacccatt        840 agcgcgcatt aaatcttatg ccagcggcgg cgtcccacca gccctgatgg gcatgggtcc       900
ggtcccagcc acgcaaaaag ccctgcaatt agcgggcctg caactggccg acattgatct       960
gatcgaggcg aacgaggcgt tgcagcgca gttcctggcg gtgggtaaga atctgggctt       1020
cgacagcgag aaagtcaatg tgaacggtgg cgcgattgcg ttaggccatc cgattggtgc      1080
aagcggcgca cgcatcttag tgacgttact gcacgccatg caggcacgcg acaagacctt      1140
aggcctggcg accttatgta ttggtggcgg tcaaggtatc gccatggtga tcgaacgcct      1200
gaactgaaga tctaggagga aagcaaaatg aaactgagca ccaagctgtg ctggtgtggc      1260
atcaagggtc gcctgcgccc acaaaagcag caacagctgc acaacacgaa cctgcaaatg      1320
accgagctga aaaagcagaa gacggccgag caaaagaccc gcccgcagaa cgttggcatc      1380
aagggcatcc agatttatat cccgacgcag tgtgtcaacc aatctgagct ggagaaattc      1440
gatggcgtca gccagggtaa gtacaccatc ggcctgggcc agaccaacat gagcttcgtg      1500
aacgaccgtg aggacatcta ttctatgagc ctgacggtgc tgtctaagct gatcaagagc      1560
tacaacatcg acacgaataa gatcggtcgt ctggaggtgg gtacgagac  gctgattgac      1620 aagagcaaaa gcgtgaagtc tgtcttaatg cagctgttcg gcgagaacac ggatgtcgag      1680
ggtatcgaca ccctgaacgc gtgttacggc ggcaccaacg cactgttcaa tagcctgaac      1740
tggattgaga gcaacgcctg ggatggccgc gatgcgatcg tcgtgtgcgg cgatatcgcc      1800
atctatgaca agggtgcggc acgtccgacc ggcggtgcag gcaccgttgc gatgtggatt      1860
ggcccggacg caccaattgt cttcgattct gtccgcgcgt cttacatgga gcacgcctac      1920 gactttttaca agccggactt cacgagcgaa tacccgtacg tggacggcca cttctctctg      1980
acctgctatg tgaaggcgct ggaccaggtt tataagtctt atagcaaaaa ggcgatttct      2040
aagggcctgg tcagcgaccc ggcaggcagc gacgccctga acgtgctgaa gtatttcgac      2100
tacaacgtgt tccatgtccc gacctgcaaa ttagtgacca aatcttatgg ccgcctgtta      2160
tataatgatt tccgtgccaa cccgcagctg ttcccggagg ttgacgccga gctggcgacg      2220
cgtgattacg acgagagcct gaccgacaag aacatcgaga agaccttcgt caacgtcgcg      2280
aagccgttcc acaaagagcg tgtggcccaa agcctgatcg tcccgaccaa cacgggcaac      2340
atgtataccg cgtctgtcta cgcggcattc gcgagcctgc tgaattacgt cggttctgac      2400
gacctgcagg gcaagcgcgt tggcctgttc agctacggta gcggcttagc ggccagcctg      2460
tatagctgca aaattgtcgg cgacgtccag cacatcatca aggagctgga catcaccaac      2520
aagctggcga agcgcatcac cgagacgccg aaagattacg aggcagcgat cgagttacgc      2580
gagaatgcgc atctgaagaa gaacttcaag ccgcaaggta gcatcgagca cctgcagagc      2640
ggcgtctact acctgacgaa cattgacgac aagttccgcc gttcttatga cgtcaaaaag      2700
taactagtag gaggaaaaca tcatggtgct gacgaacaaa accgtcatta gcggcagcaa      2760
ggtgaagtct ctgagcagcg cccaaagctc tagcagcggc ccgtctagca gcagcgagga      2820
ggacgacagc cgtgacattg agtctctgga caagaagatc cgcccgctgg aggagttaga      2880
ggccctgctg agcagcggca acaccaagca gctgaagaac aaggaagttg cagcgctggt      2940
gatccacggt aagctgccac tgtatgcgct ggaaaagaaa ctgggcgata cgacgcgtgc      3000
ggtcgcggtg cgtcgcaaag ccttaagcat cttagcggag gccccggtgt tagccagcga      3060
```

-continued

```
ccgcctgccg tacaagaact acgactacga ccgcgtgttt ggcgcgtgct gcgagaatgt    3120
cattggctac atgccgttac cggttggtgt gatcggcccg ctggtcattg atggcacgag    3180
ctatcacatt ccaatggcga ccacggaagg ttgcttagtc gccagcgcca tgcgtggctg    3240
taaggcgatt aacgccggcg gtggcgcgac gaccgtgtta accaaggatg gtatgacgcg    3300
cggtccggtc gtccgcttcc caacgctgaa gcgcagcggc gcgtgtaaga tttggctgga    3360
ttctgaggag ggccaaaacg cgatcaagaa agccttcaac tctacgagcc gtttcgcgcg    3420
tttacagcat atccagacct gcctggccgg cgacctgctg ttcatgcgct ccgcaccac     3480 cacgggcgat gcgatgggca tgaacatgat cagcaagggc gtcgaatata gcctgaaaca    3540
aatggtggaa gaatatggct gggaggacat ggaggttgtc tctgtgagcg gcaactattg    3600
caccgacaag aagccggcag ccattaactg gattgagggt cgcggcaaaa gcgtcgtggc    3660
agaagcgacc atcccaggcg acgtggtccg taaggttctg aagagcgacg tcagcgccct    3720
ggttgagtta aatatcgcga aaaacctggt cggcagcgcg atggcgggca gcgtgggtgg    3780
ctttaacgca catgcagcga atctggttac ggcggttttc ttagccttag gtcaggaccc    3840
agcccaaaat gtcgagagca gcaactgcat taccttaatg aaagaggttg acggtgacct    3900
gcgcatcagc gtttctatgc cgtctatcga ggtcggcacg atcggcggcg caccgttttt    3960
agaaccgcaa ggtgcgatgc tggatctgct gggcgtgcgc ggcccacatg caacggcccc    4020
aggcaccaat gcccgccaac tggcccgtat cgtggcctgc gcggttctgg cgggtgagct    4080
gagcctgtgc gccgcattag ccgcgggcca tttagttcaa tctcacatga cccacaaccg    4140
caagccggca gaaccaacca agccaaataa cctggacgca accgacatta accgtctgaa    4200
ggatggcagc gtcacgtgca ttaaaagctg agcatgctac taagctt                  4247
```

<210> SEQ ID NO 2
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctactagta ggaggaaaac atcatgcaaa gtttagataa gaatttccg                 49

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcttctagac tattgttgtc taatttcttg taaaatgcg                            39

<210> SEQ ID NO 4
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaactgaaga tctaggagga aagcaaaatg acaataggta tcgacaaaat aaact          55

<210> SEQ ID NO 5
<211> LENGTH: 52
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 5
ttgcatgatg ttttcctcct actagttact ctggtctgtg atattcgcga ac    52

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 6
gctaggccat cctggccatg aagaactgtg tgattgtttc tg    42

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 7
gcttgcgatc gccggcggat ttgtcctact cag    33

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 8
ccacctcgag atgtcattac cgttcttaac ttctg    35

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 9
tggtggagct cttatttaag ctgggtaaat gcagataatc g    41

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 10
ttcttgagct cttattcctt tggtagacca gtctttgcg    39

```
<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tatggatcct aaggaggata tttagatgaa aacagtagtt attattgatg c          51

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agctaagctt ttattgtttt cttaaatcat ttaaaatagc                       40

<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tatagatctt aaggaggata tttagatgac aattgggatt gataaaatta g          51

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tttggatcct tagtttcgat aagagcgaac gg                               32

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acactcgagg aggaataaat gagttttgat attgccaaat acccg                 45

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgatggtacc ttatgccagc caggccttga ttttggc                          37
```

```
<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
actaggtacc aggaggaata aatgaagcaa ctcaccattc tgggc              45

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aattgatggg ccctcagctt gcgagacgca tcacctc                       37

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cataaagggc ccaggaggaa taaatggcaa ccactcattt ggatg              45

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tattgttcat atgttatgta ttctcctgat ggatggttcg                    40

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aactaacaca tatgaggagg aataaatgcg gacacagtgg ccctc              45

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgttagttac gcgtttaaag catggctctg tgcaatgg                      38

<210> SEQ ID NO 23
```

-continued

```
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
acgggatcca ggaggaataa atgcgaattg gacacggttt tgacg            45

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tttagttggg ccctcatttt gttgccttaa tgagtagcgc c                41

<210> SEQ ID NO 25
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tactaagggc ccaggaggaa ataatgcata accaggctcc aattcaacg        49

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tccgggtacc ttattttcca acctgctgaa cgtcaattcg                  40

<210> SEQ ID NO 27
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aacaggtacc aggaggaaat aatgcagatc ctgttggcca acc              43

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tggatgaagt cgacttaatc gacttcacga atatcgacac gcagc            45

<210> SEQ ID NO 29
<211> LENGTH: 50
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
catcaagtcg acaggaggaa ataatgcaaa cggaacacgt cattttattg            50

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
taatgcaagc ttatttaagc tgggtaaatg cagataatcg                       40

<210> SEQ ID NO 31
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cagtaaagct taggaggaaa taatggactt tccgcagcaa ctcg                  44

<210> SEQ ID NO 32
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tagttccatg gttatttatt acgctggatg atgtagtccg c                     41

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
acatagacgt cgggaaagcg aggatctagg taggg                            35

<210> SEQ ID NO 34
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ttcccgctcg aggtggcgga ccatataggc agatcag                          37

<210> SEQ ID NO 35
<211> LENGTH: 23
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 35
gacgtcgata tctggcgaaa atg                                           23

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tactagtgct tggattctca cc                                            22

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ccatggacac tctgccgatc tcttccgtaa gc                                 32

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gagctctcat acgaccatag ggtgtacg                                      28

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccatggacct ggcagtagaa attgc                                         25

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gagctcttac atcggtaccg gctccag                                       27

<210> SEQ ID NO 41
<211> LENGTH: 3978
<212> TYPE: DNA
<213> ORGANISM: Artificial Sequence
```

<220> FEATURE:
<223> OTHER INFORMATION: Description of Artificial Sequence: Synthetic polynucleotide

<400> SEQUENCE: 41

```
atgaagaact gtgtgattgt ttctgcggtc cgcacggcga tcggcagctt taacggctct      60
ttagcgagca cctctgcaat cgatctgggt gcgacggtca ttaaggccgc cattgaacgc     120
gccaaaatcg acagccagca cgttgatgag gtgatcatgg gcaatgtgtt acaagccggc     180
ctgggtcaaa acccagcgcg tcaagcactg ttaaaatctg gtctggccga gaccgtgtgt     240
ggcttcaccg tcaataaggt ttgcggctct ggcctgaaga gcgtggccct ggcagcacaa     300
gcgattcaag ccggtcaggc acaaagcatc gttgcgggtg catggagaa catgtctctg      360
gcgccgtact tattagatgc caaagcccgc agcggttatc gcctgggcga tggtcaggtg     420
tacgacgtca tcttacgcga tggcttaatg tgcgcgaccc acggttacca catgggtatt     480
acggccgaaa cgtggcgaa agaatacggc attacgcgcg agatgcagga tgaattagca      540
ctgcactctc agcgcaaagc agcagccgcg atcgagtctg gtgcgtttac ggcggaaatc     600
gtgccagtta acgtggtcac gcgcaagaag acgttcgttt tcagccagga cgagttcccg     660
aaggcaaaca gcaccgcgga ggccttaggt gccttacgcc cagcctttga caaagcgggc     720
acggtcaccg ccggtaatgc gagcggcatc aatgatggtg cagcggcact ggtcatcatg     780
gaagagagcg ccgcattagc agcgggtctg accccattag cgcgcattaa atcttatgcc     840
agcggcggc tccaccagc cctgatgggc atgggtccgg tcccagccac gcaaaaagcc       900
ctgcaattag cgggcctgca actggccgac attgatctga tcgaggcgaa cgaggcgttt     960
gcagcgcagt tcctggcggt gggtaagaat ctgggcttcg acagcgagaa agtcaatgtg    1020
aacggtggcg cgattgcgtt aggccatccg attggtgcaa gcggcgcacg catcttagtg    1080
acgttactgc acgccatgca ggcacgcgac aagaccttag gcctggcgac cttatgtatt    1140
ggtggcggtc aaggtatcgc catggtgatc gaacgcctga actgaagatc taggaggaaa    1200
gcaaaatgaa actgagcacc aagctgtgct ggtgtggcat caagggtcgc ctgcgcccac    1260
aaaagcagca acagctgcac aacacgaacc tgcaaatgac cgagctgaaa aagcagaaga    1320
cggccgagca aaagacccgc ccgcagaacg ttggcatcaa gggcatccag atttatatcc    1380
cgacgcagtg tgtcaaccaa tctgagctgg agaaattcga tggcgtcagc cagggtaagt    1440
acaccatcgg cctgggccag accaacatga gcttcgtgaa cgaccgtgag gacatctatt    1500
ctatgagcct gaccggtgctg tctaagctga tcaagagcta caacatcgac acgaataaga    1560
tcggtcgtct ggaggtgggt acggagacgt tgattgacaa gagcaaaagc gtgaagtctg    1620
tcttaatgca gctgttcggc gagaacacgg atgtcgaggg tatcgacacc ctgaacgcgt    1680
gttacggcgg caccaacgca ctgttcaata gcctgaactg gattgagagc aacgcctggg    1740
atggccgcga tgcgatcgtc gtgtgcgcg atatcgccat ctatgacaag ggtgcggcac    1800
gtccgaccgg cggtgcaggc accgttgcga tgtggattgg cccggacgca ccaattgtct    1860
tcgattctgt ccgcgcgtct tacatggagc acgcctacga cttttacaag ccggacttca    1920
cgagcgaata cccgtacgtg gacggccact ctctctgac ctgctatgtg aaggcgctgg     1980
accaggttta taagtcttat agcaaaaagg cgatttctaa gggcctggtc agcgacccgg    2040
caggcagcga cgccctgaac gtgctgaagt atttcgacta caacgtgttc catgtcccga    2100
cctgcaaatt agtgaccaaa tcttatggcc gcctgttata taatgatttc cgtgccaacc    2160
cgcagctgtt cccggaggtt gacgccgagc tggcgacgcg tgattacgac gagagcctga    2220
```

```
ccgacaagaa catcgagaag accttcgtca acgtcgcgaa gccgttccac aaagagcgtg    2280
tggcccaaag cctgatcgtc ccgaccaaca cgggcaacat gtataccgcg tctgtctacg    2340
cggcattcgc gagcctgctg aattacgtcg gttctgacga cctgcagggc aagcgcgttg    2400
gcctgttcag ctacggtagc ggcttagcgg ccagcctgta tagctgcaaa attgtcggcg    2460
acgtccagca catcatcaag gagctggaca tcaccaacaa gctggcgaag cgcatcaccg    2520
agacgccgaa agattacgag gcagcgatcg agttacgcga gaatgcgcat ctgaagaaga    2580
acttcaagcc gcaaggtagc atcgagcacc tgcagagcgg cgtctactac ctgacgaaca    2640
ttgacgacaa gttccgccgt tcttatgacg tcaaaaagta actagtagga ggaaaacatc    2700
atgcaaagtt tagataagaa tttccgacat ttatctcgtc aacaaaagtt acaacaattg    2760
gtagataagc aatggttatc agaagatcaa ttcgacattt tattgaatca tccattaatt    2820
gatgaggaag tagcaaatag tttaattgaa aatgtcatcg cgcaaggtgc attacccgtt    2880
ggattattac cgaatatcat tgtggacgat aaggcatatg ttgtacctat gatggtggaa    2940
gagccttcag ttgtcgctgc agctagttat ggtgcaaagc tagtgaatca gactggcgga    3000
tttaaaacgg tatcttctga acgtattatg ataggtcaaa tcgtctttga tggcgttgac    3060
gatactgaaa aattatcagc agacattaaa gctttagaaa agcaaattca taaaattgcg    3120
gatgaggcat atccttctat aaagcgcgt ggtggtggtt accaacgtat agctattgat    3180
acatttcctg agcaacagtt actatcttta aaagtatttg ttgatacgaa agatgctatg    3240
ggcgctaata tgcttaatac gattttagag gccataactg cattttttaaa aaatgaatct    3300 ccacaaagcg acattttaat gagtatttta tccaatcatg caacagcgtc cgttgttaaa    3360
gttcaaggcg aaattgacgt taaagattta gcaaggggcg agagaactgg agaagaggtt    3420
gccaaacgaa tggaacgtgc ttctgtattg gcacaagttg atattcatcg tgctgcaaca    3480
cataataaag gtgttatgaa tggcatacat gccgttgttt tagcaacagg aaatgatacg    3540
cgtggtgcag aagcaagtgc gcatgcatac gcgagtcgtg acggacagta tcgtggtatt    3600
gcaacatgga gatacgatca aaaacgtcaa cgtttaattg gtacaataga agtgcctatg    3660
acattggcaa tcgttggcgg tggtacaaaa gtattaccaa ttgctaaagc ttctttagaa    3720
ttgctaaatg tagattcagc acaagaatta ggtcatgtag ttgctgccgt tggtttagca    3780
cagaactttg cagcatgtcg cgcgctcgtt tccgaaggta tccagcaagg ccatatgagc    3840
ttgcaatata atctttagc tattgttgta ggtgcaaaag gtgatgaaat tgcgcaagta    3900
gctgaagcat tgaagcaaga accccgtgcg aatacacaag tagctgaacg catttttacaa    3960 gaaattagac aacaatag                                                  3978
```

<210> SEQ ID NO 42
<211> LENGTH: 3669
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
atgaagaact gtgtgattgt ttctgcggtc cgcacggcga tcggcagctt taacggctct     60
ttagcgagca cctctgcaat cgatctgggt gcgacggtca ttaaggccgc cattgaacgc    120
gccaaaatcg cagccagca cgttgatgag gtgatcatgg gcaatgtgtt acaagccggc    180
ctgggtcaaa acccagcgcg tcaagcactg ttaaaatctg gtctggccga gaccgtgtgt    240
```

-continued

| | |
|---|---|
| ggcttcaccg tcaataaggt ttgcggctct ggcctgaaga gcgtggccct ggcagcacaa | 300 |
| gcgattcaag ccggtcaggc acaaagcatc gttgcgggtg catggagaa catgtctctg | 360 |
| gcgccgtact tattagatgc caaagcccgc agcggttatc gcctgggcga tggtcaggtg | 420 |
| tacgacgtca tcttacgcga tggcttaatg tgcgcgaccc acggttacca catgggtatt | 480 |
| acggccgaaa acgtggcgaa agaatacggc attacgcgcg agatgcagga tgaattagca | 540 |
| ctgcactctc agcgcaaagc agcagccgcg atcgagtctg gtgcgtttac ggcggaaatc | 600 |
| gtgccagtta acgtggtcac gcgcaagaag acgttcgttt tcagccagga cgagttcccg | 660 |
| aaggcaaaca gcaccgcgga ggccttaggt gccttacgcc cagcctttga caaagcgggc | 720 |
| acggtcaccg ccggtaatgc gagcggcatc aatgatggtg cagcggcact ggtcatcatg | 780 |
| gaagagagcg ccgcattagc agcgggtctg accccattag cgcgcattaa atcttatgcc | 840 |
| agcggcggcg tcccaccagc cctgatgggc atgggtccgg tcccagccac gcaaaaagcc | 900 |
| ctgcaattag cgggcctgca actggccgac attgatctga tcgaggcgaa cgaggcgttt | 960 |
| gcagcgcagt tcctggcggt gggtaagaat ctgggcttcg acagcgagaa agtcaatgtg | 1020 |
| aacggtggcg cgattgcgtt aggccatccg attggtgcaa gcggcgcacg catcttagtg | 1080 |
| acgttactgc acgccatgca ggcacgcgac aagaccttag gcctggcgac cttatgtatt | 1140 |
| ggtggcggtc aaggtatcgc catggtgatc gaacgcctga actgaagatc taggaggaaa | 1200 |
| gcaaaatgac aataggtatc gacaaaataa acttttacgt tccaaagtac tatgtagaca | 1260 |
| tggctaaatt agcagaagca cgccaagtag acccaaacaa attttaatt ggaattggtc | 1320 |
| aaactgaaat ggctgttagt cctgtaaacc aagacatcgt ttcaatgggc gctaacgctg | 1380 |
| ctaaggacat tataacagac gaagataaaa agaaaattgg tatggtaatt gtggcaactg | 1440 |
| aatcagcagt tgatgctgct aaagcagccg ctgttcaaat tcacaactta ttaggtattc | 1500 |
| aacctttgc acgttgcttt gaaatgaaag aagcttgtta tgctgcaaca ccagcaattc | 1560 |
| aattagctaa agattattta gcaactagac cgaatgaaaa agtattagtt attgctacag | 1620 |
| atacagcacg ttatggattg aattcaggcg gcgagccaac acaaggtgct ggcgcagttg | 1680 |
| cgatggttat tgcacataat ccaagcattt tggcattaaa tgaagatgct gttgcttaca | 1740 |
| ctgaagacgt ttatgatttc tggcgtccaa ctggacataa atatccatta gttgatggtg | 1800 |
| cattatctaa agatgcttat atccgctcat ccaacaaag ctggaatgaa tacgcaaaac | 1860 |
| gtcaaggtaa gtcgctagct gacttcgcat ctctatgctt ccatgttcca tttcaaaaaa | 1920 |
| tgggtaaaaa ggcattagag tcaatcattg ataacgctga tgaaacaact caagagcgtt | 1980 |
| tacgttcagg atatgaagat gctgtagatt ataaccgtta tgtcggtaat atttatactg | 2040 |
| gatcattata tttaagccta atatcattac ttgaaaatcg tgatttacaa gctggtgaaa | 2100 |
| caatcggttt attcagttat ggctcaggtt cagttggtga attttatagt gcgacattag | 2160 |
| ttgaaggcta caaagatcat ttagatcaag ctgcacataa agcattatta aataaccgta | 2220 |
| ctgaagtatc tgttgatgca tatgaaacat tcttcaaacg ttttgatgac gttgaatttg | 2280 |
| acgaagaaca agatgctgtt catgaagatc gtcatatttt ctacttatca aatattgaaa | 2340 |
| ataacgttcg cgaatatcac agaccagagt aactagtagg aggaaaacat catgcaaagt | 2400 |
| ttagataaga atttccgaca tttatctcgt caacaaaagt tacaacaatt ggtagataag | 2460 |
| caatggttat cagaagatca attcgacatt ttattgaatc atccattaat tgatgaggaa | 2520 |
| gtagcaaata gtttaattga aaatgtcatc gcgcaaggtg cattacccgt tggattatta | 2580 |

```
ccgaatatca ttgtggacga taaggcatat gttgtaccta tgatggtgga agagccttca      2640
gttgtcgctg cagctagtta tggtgcaaag ctagtgaatc agactggcgg atttaaaacg      2700
gtatcttctg aacgtattat gataggtcaa atcgtctttg atggcgttga cgatactgaa      2760
aaattatcag cagacattaa agctttagaa aagcaaattc ataaaattgc ggatgaggca      2820
tatccttcta ttaaagcgcg tggtggtggt taccaacgta tagctattga tacatttcct      2880
gagcaacagt tactatcttt aaaagtattt gttgatacga agatgctat gggcgctaat       2940 atgcttaata cgattttaga ggccataact gcattttaa aaaatgaatc tccacaaagc       3000
gacattttaa tgagtatttt atccaatcat gcaacagcgt ccgttgttaa agttcaaggc      3060
gaaattgacg ttaaagattt agcaaggggc gagagaactg agaagaggt tgccaaacga       3120 atggaacgtg cttctgtatt ggcacaagtt gatattcatc gtgctgcaac acataataaa      3180
ggtgttatga atggcataca tgccgttgtt ttagcaacag gaaatgatac gcgtggtgca      3240
gaagcaagtg cgcatgcata cgcgagtcgt gacggacagt atcgtggtat tgcaacatgg      3300
agatacgatc aaaaacgtca acgtttaatt ggtacaatag aagtgcctat gacattggca      3360
atcgttggcg gtggtacaaa agtattacca attgctaaag cttctttaga attgctaaat      3420
gtagattcag cacaagaatt aggtcatgta gttgctgccg ttggtttagc acagaacttt      3480
gcagcatgtc gcgcgctcgt ttccgaaggt atccagcaag gccatatgag cttgcaatat      3540
aaatctttag ctattgttgt aggtgcaaaa ggtgatgaaa ttgcgcaagt agctgaagca      3600
ttgaagcaag aaccccgtgc gaatacacaa gtagctgaac gcattttaca agaaattaga      3660
caacaatag                                                              3669

<210> SEQ ID NO 43
<211> LENGTH: 2235
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
caataccgac ttaccatcct atttgctttg cccttttttct tttccactgc atggcggcgt      60
tagtatcgaa tggatggcgg cgttagtatc gaatcgacag cagtatagcg accagcattc      120
acatacgatt gacgcatgat attactttct gcgcacttaa cttcgcatct gggcagatga      180
tgtcgaggcg aaaaaaaata taaatcacgc taacatttga ttaaaataga caactacaa       240 tataaaaaaa ctatacaaat gacaagttct tgaaaacaag aatctttta ttgtcagtac       300 tgattagaaa aactcatcga gcatcaaatg aaactgcaat ttattcatat caggattatc      360 ataccatat ttttgaaaaa gccgtttctg taatgaagga gaaaactcac cgaggcagtt       420
ccataggatg gcaagatcct ggtatcggtc tgcgattccg actcgtccaa catcaataca      480
acctattaat ttcccctcgt caaaaataag gttatcaagt gagaaatcac catgagtgac      540
gactgaatcc ggtgagaatg gcaaaagctt atgcatttct ttccagactt gttcaacagg      600
ccagccatta cgctcgtcat caaaatcact cgcatcaacc aaaccgttat tcattcgtga      660
ttgcgcctga gcgagacgaa atacgcgatc gctgttaaaa ggacaattac aaacaggaat      720
cgaatgcaac cggcgcagga acactgccag cgcatcaaca atattttcac ctgaatcagg      780
atattcttct aatacctgga atgctgtttt gccggggatc gcagtggtga gtaaccatgc      840
atcatcagga gtacgcataa aatgcttgat ggtcggaaga ggcataaatt ccgtcagcca      900
```

-continued

```
gtttagtctg accatctcat ctgtaacatc attggcaacg ctacctttgc catgtttcag      960
aaacaactct ggcgcatcgg gcttcccata caatcgatag attgtcgcac ctgattgccc     1020
gacattatcg cgagcccatt tatacccata taaatcagca tccatgttgg aatttaatcg     1080
cggcctcgaa acgtgagtct tttccttacc catggttgtt tatgttcgga tgtgatgtga     1140
gaactgtatc ctagcaagat tttaaaagga agtatatgaa agaagaacct cagtggcaaa     1200
tcctaacctt ttatatttct ctacaggggc gcggcgtggg gacaattcaa cgcgtctgtg     1260
aggggagcgt ttccctgctc gcaggtctgc agcgaggagc cgtaattttt gcttcgcgcc     1320
gtgcggccat caaaatgtat ggatgcaaat gattatacat ggggatgtat gggctaaatg     1380
tacgggcgac agtcacatca tgcccctgag ctgcgcacgt caagactgtc aaggagggta     1440
ttctgggcct ccatgtcgct ggccgggtga cccggcgggg acgaggcaag ctaaacagat     1500
ctgatcttga aactgagtaa gatgctcaga atacccgtca agataagagt ataatgtaga     1560
gtaatatacc aagtattcag catattctcc tcttcttttg tataaatcac ggaagggatg     1620
atttataaga aaaatgaata ctattacact tcatttacca ccctctgatc tagattttcc     1680
aacgatatgt acgtagtggt ataaggtgag ggggtccaca gatataacat cgtttaattt     1740
agtactaaca gagacttttg tcacaactac atataagtgt acaaatatag tacagatatg     1800
acacacttgt agcgccaacg cgcatcctac ggattgctga cagaaaaaaa ggtcacgtga     1860
ccagaaaagt cacgtgtaat tttgtaactc accgcattct agcggtccct gtcgtgcaca     1920
ctgcactcaa caccataaac cttagcaacc tccaaaggaa atcaccgtat aacaaagcca     1980
cagttttaca acttagtctc ttatgaagtt acttaccaat gagaaataga ggctctttct     2040 cgagaaaatat gaatatggat atatatatat atatatatat atatatatat atatgtaaac     2100
ttggttcttt tttagcttgt gatctctagc ttgggtctct ctctgtcgta acagttgtga     2160
tatcggctgc cttcatctcg accggatgca atgccaattg taatagcttt cccatgttaa     2220
ttatacttta ttctt                                                     2235

<210> SEQ ID NO 44
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gagtgaacct gctgcctggc gtgctctgac tcagtacatt tcatagtgga tggcggcgtt      60
agtatc                                                                66

<210> SEQ ID NO 45
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cgtgtatacg ttttccgctt ctgctcttcg tcttttctct tcttccgata tcacaactgt      60
tacga                                                                 65

<210> SEQ ID NO 46
<211> LENGTH: 70
```

<210> SEQ ID NO 47
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46

```
ggtaagacgg ttgggtttta tcttttgcag ttggtactat taagaacaat cacaggaaac    60
agctatgacc                                                           70
```

<210> SEQ ID NO 47
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 47

```
ttgcgttttg tactttggtt cgctcaattt tgcaggtaga taatcgaaaa gttgtaaaac    60
gacggccagt                                                           70
```

<210> SEQ ID NO 48
<211> LENGTH: 5487
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

```
gtttaaactt gctaaattcg agtgaaacac aggaagacca gaaaatcctc atttcatcca    60
tattaacaat aatttcaaat gtttatttgc attatttgaa actagggaag acaagcaacg   120
aaacgttttg aaaattttga gtattttcaa taaatttgta gaggactcag atattgaaaa   180
aaagctacag caattaatac ttgataagaa gagtattgag aagggcaacg ttcatcatc   240
tcatggatct gcacatgaac aaacaccaga gtcaaacgac gttgaaattg aggctactgc   300
gccaattgat gacaatacag acgatgataa caaaccgaag ttatctgatg tagaaaagga   360
ttaaagatgc taagagatag tgatgatatt tcataaataa tgtaattcta tatatgttaa   420
ttacctttt tgcgaggcat atttatggtg aaggataagt tttgaccatc aaagaaggtt   480
aatgtggctg tggtttcagg gtccataccc gggagttatg acaattacaa caacagaatt   540
ctttctatat atgcacgaac ttgtaatatg aagaaatta tgacgtacaa actataaagt   600
aaatatttta cgtaacacat ggtgctgttg tgcttctttt tcaagagaat accaatgacg   660
tatgactaag tttaggattt aatgcaggtg acggacccat ctttcaaacg atttatatca   720
gtggcgtcca aattgttagg ttttgttggt tcagcaggtt tcctgttgtg ggtcatatga   780
ctttgaacca aatggccggc tgctagggca gcacataagg ataattcacc tgccaagacg   840
gcacaggcaa ctattcttgc taattgacgt gcgttggtac caggagcggt agcatgtggg   900
cctcttacac ctaataagtc caacatggca ccttgtggtt ctagaacagt accaccaccg   960
atggtaccta cttcgatgga tggcatggat acggaaattc tcaaatcacc gtccacttct  1020
ttcatcaatg ttatacagtt ggaactttcg acattttgtg caggatcttg tcctaatgcc  1080
aagaaaacag ctgtcactaa attagctgca tgtgcgttaa atccaccaac agacccagcc  1140
attgcagatc caaccaaatt cttagcaatg ttcaactcaa ccaatgcgga aacatcactt  1200
tttaacactt ttctgacaac atcaccagga atagtagctt ctgcgacgac actcttacca  1260
```

-continued

```
cgaccttcga tccagttgat ggcagctggt tttttgtcgg tacagtagtt accagaaacg    1320
gagacaacct ccatatcttc ccagccatac tcttctacca tttgctttaa tgagtattcg    1380
acacccttag aaatcatatt catacccatt gcgtcaccag tagttgttct aaatctcatg    1440
aagagtaaat ctcctgctag acaagtttga atatgttgca gacgtgcaaa tcttgatgta    1500
gagttaaaag cttttttaat tgcgttttgt ccctcttctg agtctaacca tatcttacag    1560
gcaccagatc ttttcaaagt tgggaaacgg actactgggc ctcttgtcat accatcctta    1620
gttaaaacag ttgttgcacc accgccagca ttgattgcct tacagccacg catggcagaa    1680
gctaccaaac aaccctctgt agttgccatt ggtatatgat aagatgtacc atcgataacc    1740
aaggggccta taacaccaac gggcaaaggc atgtaaccta aacattttc acaacaagcg    1800 ccaaatacgc ggtcgtagtc ataatttta tatggtaaac gatcagatgc taatacagga    1860
gcttctgcca aaattgaaag agccttccta cgtaccgcaa ccgctctcgt agtatcacct    1920 aatttttct ccaaagcgta caaaggtaac ttaccgtgaa taaccaaggc agcgacctct    1980
ttgttcttca attgttttgt atttccacta cttaataatg cttctaattc ttctaaagga    2040 cgtatttct tatccaagct ttcaatatcg cgggaatcat cttcctcact agatgatgaa    2100
ggtcctgatg agctcgattg cgcagatgat aaacttttga ctttcgatcc agaaatgact    2160
gttttattgg ttaaaactgg tgtagaagcc ttttgtacag gagcagtaaa agacttcttg    2220
gtgacttcag tcttcaccaa ttggtctgca gccattatag tttttctcc ttgacgttaa    2280 agtatagagg tatattaaca attttttgtt gatactttta tgacatttga ataagaagta    2340
atacaaaccg aaaatgttga aagtattagt taaagtggtt atgcagcttt tgcatttata    2400
tatctgttaa tagatcaaaa atcatcgctt cgctgattaa ttaccccaga ataaggcta    2460 aaaaactaat cgcattatta tcctatggtt gttaatttga ttcgttgatt tgaaggtttg    2520
tggggccagg ttactgccaa tttttcctct tcataaccat aaaagctagt attgtagaat    2580
ctttattgtt cggagcagtg cggcgcgagg cacatctgcg tttcaggaac gcgaccggtg    2640
aagaccagga cgcacggagg agagtcttcc gtcggagggc tgtcgcccgc tcggcggctt    2700
ctaatccgta cttcaatata gcaatgagca gttaagcgta ttactgaaag ttccaaagag    2760 aaggttttt taggctaaga aatgggggct ctttacattt ccacaacata taagtaagat    2820
tagatatgga tatgtatatg gtggtattgc catgtaatat gattattaaa cttctttgcg    2880
tccatccaaa aaaaaagtaa gaattttga aaattcaata taaatgaaac tctcaactaa    2940
actttgttgg tgtggtatta aaggaagact taggccgcaa aagcaacaac aattacacaa    3000
tacaaacttg caaatgactg aactaaaaaa acaaaagacc gctgaacaaa aaaccagacc    3060
tcaaaatgtc ggtattaaag gtatccaaat ttacatccca actcaatgtg tcaaccaatc    3120
tgagctagag aaatttgatg gcgtttctca aggtaaatac acaattggtc tgggccaaac    3180
caacatgtct tttgtcaatg acagagaaga tatctactcg atgtccctaa ctgttttgtc    3240
taagttgatc aagagttaca acatcgacac caacaaaatt ggtagattag aagtcggtac    3300
tgaaactctg attgacaagt ccaagtctgt caagtctgtc ttgatgcaat gtttggtga    3360 aaacactgac gtcgaaggta ttgacacgct taatgcctgt tacggtggta ccaacgcgtt    3420
gttcaactct ttgaactgga ttgaatctaa cgcatgggat ggtagagacg ccattgtagt    3480
ttgcggtgat attgccatct acgataaggg tgccgcaaga ccaaccggtg gtgccggtac    3540
tgttgctatg tggatcggtc ctgatgctcc aattgtattt gactctgtaa gagcttctta    3600
```

```
catgaacac gcctacgatt tttacaagcc agatttcacc agcgaatatc cttacgtcga    3660
tggtcatttt tcattaactt gttacgtcaa ggctcttgat caagtttaca agagttattc    3720
caagaaggct atttctaaag ggttggttag cgatcccgct ggttcggatg ctttgaacgt    3780
tttgaaatat ttcgactaca acgttttcca tgttccaacc tgtaaattgg tcacaaaatc    3840
atacggtaga ttactatata acgatttcag agccaatcct caattgttcc cagaagttga    3900
cgccgaatta gctactcgcg attatgacga atctttaacc gataagaaca ttgaaaaaac    3960
ttttgttaat gttgctaagc cattccacaa agagagagtt gcccaatctt tgattgttcc    4020
aacaaacaca ggtaacatgt acaccgcatc tgtttatgcc gcctttgcat ctctattaaa    4080
ctatgttgga tctgacgact acaaggcaa gcgtgttggt ttattttctt acggttccgg    4140
tttagctgca tctctatatt cttgcaaaat tgttggtgac gtccaacata ttatcaagga    4200
attagatatt actaacaaat tagccaagag aatcaccgaa actccaaagg attacgaagc    4260
tgccatcgaa ttgagagaaa atgcccattt gaagaagaac ttcaaacctc aaggttccat    4320
tgagcatttg caaagtggtg tttactactt gaccaacatc gatgacaaat ttagaagatc    4380
ttacgatgtt aaaaaataat cttcccccat cgattgcatc ttgctgaacc cccttcataa    4440
atgctttatt tttttggcag cctgcttttt ttagctctca tttaatagag tagttttttta    4500 atctatatac taggaaaact ctttatttaa taacaatgat atatatatac ccggaaagct    4560
tttcaattca tctttttttt ttttgttctt tttttgatt ccggtttctt tgaaattttt    4620
ttgattcggt aatctccgag cagaaggaag aacgaaggaa ggagcacaga cttagattgg    4680
tatatatacg catatgtggt gttgaagaaa catgaaattg cccagtattc ttaacccaac    4740
tgcacagaac aaaaacctgc aggaaacgaa gataaatcat gtcgaaagct acatataagg    4800
aacgtgctgc tactcatcct agtcctgttg ctgccaagct atttaatatc atgcacgaaa    4860
agcaaacaaa cttgtgtgct tcattggatg ttcgtaccac caaggaatta ctggagttag    4920
ttgaagcatt aggtcccaaa atttgtttac taaaaacaca tgtggatatc ttgactgatt    4980
tttccatgga gggcacagtt aagccgctaa aggcattatc cgccaagtac aattttttac    5040
tcttcgaaga cagaaaattt gctgacattg gtaatacagt caaattgcag tactctgcgg    5100
gtgtatacag aatagcagaa tgggcagaca ttacgaatgc acacggtgtg gtgggcccag    5160
gtattgttag cggttttgaag caggcggcgg aagaagtaac aaaggaacct agaggccttt    5220
tgatgttagc agaattgtca tgcaagggct ccctagctac tggagaatat actaagggta    5280
ctgttgacat tgcgaagagc gacaaagatt ttgttatcgg ctttattgct caaagagaca    5340
tgggtggaag agatgaaggt tacgattggt tgattatgac acccggtgtg ggtttagatg    5400
acaagggaga cgcattgggt caacagtata gaaccgtgga tgatgtggtc tctacaggat    5460
ctgacattat tattgttggg tttaaac                                        5487
```

<210> SEQ ID NO 49
<211> LENGTH: 5860
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49

```
gtttaaactt gctaaattcg agtgaaacac aggaagacca gaaatcctc atttcatcca      60 tattaacaat aatttcaaat gtttatttgc attatttgaa actagggaag acaagcaacg     120
```

```
aaacgttttt gaaaattttg agtattttca ataaatttgt agaggactca gatattgaaa      180
aaaagctaca gcaattaata cttgataaga agagtattga gaagggcaac ggttcatcat      240
ctcatggatc tgcacatgaa caaacaccag agtcaaacga cgttgaaatt gaggctactg      300
cgccaattga tgacaataca gacgatgata acaaaccgaa gttatctgat gtagaaaagg      360
attaaagatg ctaagagata gtgatgatat ttcataaata atgtaattct atatatgtta      420 attaccrtttt ttgcgaggca tatttatggt gaaggataag ttttgaccat caaagaaggt      480
taatgtggct gtggtttcag ggtccatacc cgggtatata tatatcattg ttattaaata      540 aagagtrttttc ctagtatata gattaaaaaa ctactctatt aaatgagagc taaaaaaagc      600
aggctgccaa aaaaataaag catttatgaa ggggggttcag caagatgcaa tcgatggggg      660
aagattattt tttaacatcg taagatcttc taaatttgtc atcgatgttg gtcaagtagt      720
aaacaccact ttgcaaatgc tcaatggaac cttgaggttt gaagttcttc ttcaaatggg      780
cattttctct caattcgatg gcagcttcgt aatcctttgg agtttcggtg attctcttgg      840
ctaatttgtt agtaatatct aattccttga taatatgttg gacgtcacca acaattttgc      900
aagaatatag gatgcagct aaaccggaac cgtaagaaaa taaaccaaca cgcttgcctt      960
gtaagtcgtc agatccaaca tagtttaata gagatgcaaa ggcggcataa acagatgcgg     1020
tgtacatgtt acctgtgttt gttggaacaa tcaaagattg gcaactctc tctttgtgga     1080 atggcttagc aacattaaca aaagtttttt caatgttctt atcggttaaa gattcgtcat     1140
aatcgcgagt agctaattcg gcgtcaactt ctgggaacaa ttgaggattg gctctgaaat     1200
cgttatatag taatctaccg tatgattttg tgaccaattt acaggttgga acatggaaaa     1260
cgttgtagtc gaaatatttc aaaacgttca aagcatccga accagcggga tcgctaacca     1320 acccttaga aatagccttc ttggaataac tcttgtaaac ttgatcaaga gccttgacgt     1380
aacaagttaa tgaaaaatga ccatcgacgt aaggatattc gctggtgaaa tctggcttgt     1440
aaaaatcgta ggcgtgttcc atgtaagaag ctcttacaga gtcaaataca attggagcat     1500
caggaccgat ccacatagca acagtaccgg caccaccggt tggtcttgcg gcacccttat     1560
cgtagatggc aatatcaccg caaactacaa tggcgtctct accatcccat gcgttagatt     1620
caatccagtt caaagagttg aacaacgcgt tggtaccacc gtaacaggca ttaagcgtgt     1680
caataccttc gacgtcagtg ttttcaccaa acaattgcat caagacagac ttgacagact     1740
tggacttgtc aatcagagtt tcagtaccga cttctaatct accaattttg ttggtgtcga     1800
tgttgtaact cttgatcaac ttagacaaaa cagttaggga catcgagtag atatcttctc     1860
tgtcattgac aaaagacatg ttggtttggc ccagaccaat tgtgtattta ccttgagaaa     1920
cgccatcaaa tttctctagc tcagattggt tgacacattg agttgggatg taaatttgga     1980
tacctttaat accgacattt tgaggtctgg ttttttgttc agcggtcttt tgttttttta     2040
gttcagtcat ttgcaagttt gtattgtgta attgttgttg cttttgcggc taagtcttc      2100 ctttaatacc acaccaacaa agtttagttg agagtttcat tttatgtgat gattgattga     2160
ttgattgtac agtttgtttt tcttaatatc tatttcgatg acttctatat gatattgcac     2220
taacaagaag atattataat gcaattgata caagacaagg agttatttgc ttctcttta      2280 tatgattctg acaatccata ttgcgttggt agtcttttt gctggaacgg ttcagcggaa     2340
aagacgcatc gctcttttg cttctagaag aaatgccagc aaaagaatct cttgacagtg     2400
actgacagca aaaatgtctt tttctaacta gtaacaaggc taagatatca gcctgaaata     2460
aagggtggtg aagtaataat taaatcatcc gtataaacct atacacatat atgaggaaaa     2520
```

```
ataatacaaa agtgttttaa atacagatac atacatgaac atatgcacgt atagcgccca   2580
aatgtcggta atgggatcgg cttactaatt ataaaatgca tcatagaaat cgttgaagtt   2640
gacgcagcga ctcgagatcc ataggagcaa ctcatgtctg aacttcaacg atttctatga   2700
tgcattttat aattagtaag ccgatcccat taccgacatt tgggcgctat acgtgcatat   2760
gttcatgtat gtatctgtat ttaaaacact tttgtattat ttttcctcat atatgtgtat   2820
aggtttatac ggatgattta attattactt caccacccct tatttcaggc tgatatctta   2880
gccttgttac tagttagaaa aagacatttt tgctgtcagt cactgtcaag agattctttt   2940
gctggcattt cttctagaag caaaagagc gatgcgtctt ttccgctgaa ccgttccagc    3000
aaaaaagact accaacgcaa tatggattgt cagaatcata taaaagagaa gcaaataact   3060
ccttgtcttg tatcaattgc attataatat cttcttgtta gtgcaatatc atatagaagt   3120
catcgaaata gatattaaga aaacaaact gtacaatcaa tcaatcaatc atcacataaa    3180
atggctgcag accaattggt gaagactgaa gtcaccaaga agtctttac tgctcctgta    3240 caaaaggctt ctacaccagt tttaaccaat aaaacagtca tttctggatc gaaagtcaaa   3300
agtttatcat ctgcgcaatc gagctcatca ggaccttcat catctagtga ggaagatgat   3360
tcccgcgata ttgaaagctt ggataagaaa atacgtcctt tagaagaatt agaagcatta   3420
ttaagtagtg gaaatacaaa acaattgaag aacaaagagg tcgctgcctt ggttattcac   3480
ggtaagttac ctttgtacgc tttggagaaa aaattaggtg atactacgag agcggttgcg   3540
gtacgtagga aggctctttc aattttggca gaagctcctg tattagcatc tgatcgttta   3600
ccatataaaa attatgacta cgaccgcgta tttggcgctt gttgtgaaaa tgttataggt   3660
tacatgcctt tgcccgttgg tgttataggc cccttggtta tcgatggtac atcttatcat   3720
ataccaatgg caactacaga gggttgtttg gtagcttctg ccatgcgtgg ctgtaaggca   3780
atcaatgctg gcggtggtgc aacaactgtt ttaactaagg atggtatgac aagaggccca   3840
gtagtccgtt tcccaacttt gaaaagatct ggtgcctgta agatatggtt agactcagaa   3900
gagggacaaa acgcaattaa aaaagctttt aactctacat caagatttgc acgtctgcaa   3960
catattcaaa cttgtctagc aggagattta ctcttcatga gatttagaac aactactggt   4020
gacgcaatgg gtatgaatat gatttctaag ggtgtcgaat actcattaaa gcaaatggta   4080
gaagagtatg ctgggaaga tatggaggtt gtctccgttt ctggtaacta ctgtaccgac    4140
aaaaaaccag ctgccatcaa ctggatcgaa ggtcgtggta agagtgtcgt cgcagaagct   4200
actattcctg gtgatgttgt cagaaaagtg ttaaaaagtg atgtttccgc attggttgag   4260
ttgaacattg ctaagaattt ggttggatct gcaatggctg gtctgttgg tggatttaac    4320 gcacatgcag ctaatttagt gacagctgtt ttcttggcat taggacaaga tcctgcacaa   4380
aatgtcgaaa gttccaactg tataacattg atgaaagaag tggacggtga tttgagaatt   4440
tccgtatcca tgccatccat cgaagtaggt accatcggtg gtggtactgt tctagaacca   4500
caaggtgcca tgttggactt attaggtgta agaggcccac atgctaccgc tcctggtacc   4560
aacgcacgtc aattagcaag aatagttgcc tgtgccgtct tggcaggtga attatcctta   4620
tgtgctgccc tagcagccgg ccatttggtt caaagtcata tgacccacaa caggaaacct   4680
gctgaaccaa caaaacctaa caatttggac gccactgata taaatcgttt gaaagatggg   4740
tccgtcacct gcattaaatc ctaaacttag tcatacgtca ttggtattct cttgaaaaag   4800
aagcacaaca gcaccatgtg ttacgtaaaa tatttacttt atagtttgta cgtcataatt   4860
```

```
tcttccatat tacaagttcg tgcatatata gaaagaattc tgttgttgta attgtcataa    4920
ctcccgggaa gcttttcaat tcatctttt tttttttgtt cttttttttg attccggttt    4980
ctttgaaatt ttttttgattc ggtaatctcc gagcagaagg aagaacgaag gaaggagcac    5040
agacttagat tggtatatat acgcatatgt ggtgttgaag aaacatgaaa ttgcccagta    5100
ttcttaaccc aactgcacag aacaaaaacc tgcaggaaac gaagataaat catgtcgaaa    5160
gctacatata aggaacgtgc tgctactcat cctagtcctg ttgctgccaa gctatttaat    5220
atcatgcacg aaaagcaaac aaacttgtgt gcttcattgg atgttcgtac caccaaggaa    5280
ttactggagt tagttgaagc attaggtccc aaaatttgtt tactaaaaac acatgtggat    5340
atcttgactg attttccat ggagggcaca gttaagccgc taaaggcatt atccgccaag    5400
tacaattttt tactcttcga agacagaaaa tttgctgaca ttggtaatac agtcaaattg    5460
cagtactctg cgggtgtata cagaatagca gaatgggcag acattacgaa tgcacacggt    5520
gtggtgggcc caggtattgt tagcggtttg aagcaggcgg cggaagaagt aacaaaggaa    5580
cctagaggcc ttttgatgtt agcagaattg tcatgcaagg gctccctagc tactggagaa    5640
tatactaagg gtactgttga cattgcgaag agcgacaaag attttgttat cggctttatt    5700
gctcaaagag acatgggtgg aagagatgaa ggttacgatt ggttgattat gacacccggt    5760
gtgggtttag atgacaaggg agacgcattg ggtcaacagt atagaaccgt ggatgatgtg    5820
gtctctacag gatctgacat tattattgtt gggtttaaac    5860

<210> SEQ ID NO 50
<211> LENGTH: 5050
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gtttaaacta ctattagctg aattgccact gctatcgttg ttagtggcgt tagtgcttgc      60
attcaaagac atggagggcg ttattacgcc ggagctcctc gacagcagat ctgatgactg     120
gtcaatatat ttttgcattg aggctctgtt tggaattata ttttgagatg acccatctaa     180
tgtactggta tcaccagatt tcatgtcgtt ttttaaagcg gctgcttgag tcttagcaat     240
agcgtcacca tctggtgaat cctttgaagg aaccactgac gaaggtttgg acagtgacga     300
agaggatctt tcctgctttg aattagtcgc gctgggagca gatgacgagt tggtggagct     360 ggggcagga ttgctggccg tcgtgggtcc tgaatgggtc cttggctggt ccatctctat     420
tctgaaaacg gaagaggagt agggaatatt actggctgaa aataagtctt gaatgaacgt     480
atacgcgtat atttctacca atctctcaac actgagtaat ggtagttata agaaagagac     540
cgagttaggg acagttagag gcggtggaga tattccttat ggcatgtctg gcgatgataa     600 aactttttcaa acggcagccc cgatctaaaa gagctgacac ccgggagtta tgacaattac     660
aacaacagaa ttcttttctat atatgcacga acttgtaata tggaagaaat tatgacgtac     720
aaactataaa gtaaatattt tacgtaacac atggtgctgt tgtgcttctt tttcaagaga     780
ataccaatga cgtatgacta agtttaggat ttaatgcagg tgacggaccc atcttttcaaa     840 cgatttatat cagtggcgtc caaattgtta ggttttgttg gttcagcagg tttcctgttg     900
tgggtcatat gactttgaac caaatggccg gctgctaggg cagcacataa ggataattca     960
cctgccaaga cggcacaggc aactattctt gctaattgac gtgcgttggt accaggagcg    1020
```

```
gtagcatgtg ggcctcttac acctaataag tccaacatgg caccttgtgg ttctagaaca   1080
gtaccaccac cgatggtacc tacttcgatg gatggcatgg atacggaaat tctcaaatca   1140
ccgtccactt ctttcatcaa tgttatacag ttggaacttt cgacattttg tgcaggatct   1200
tgtcctaatg ccaagaaaac agctgtcact aaattagctg catgtgcgtt aaatccacca   1260
acagacccag ccattgcaga tccaaccaaa ttcttagcaa tgttcaactc aaccaatgcg   1320
gaaacatcac tttttaacac ttttctgaca acatcaccag gaatagtagc ttctgcgacg   1380
acactcttac cacgaccttc gatccagttg atggcagctg ttttttgtc ggtacagtag    1440 ttaccagaaa cggagacaac ctccatatct tcccagccat actcttctac catttgcttt   1500
aatgagtatt cgacacccett agaaatcata ttcataccca ttgcgtcacc agtagttgtt   1560
ctaaatctca tgaagagtaa atctcctgct agacaagttt gaatatgttg cagacgtgca   1620
aatcttgatg tagagttaaa agctttttta attgcgtttt gtccctcttc tgagtctaac   1680
catatcttac aggcaccaga tcttttcaaa gttgggaaac ggactactgg gcctcttgtc   1740
ataccatcct tagttaaaac agttgttgca ccaccgccag cattgattgc cttacagcca   1800
cgcatggcag aagctaccaa acaaccctct gtagttgcca ttggtatatg ataagatgta   1860
ccatcgataa ccaaggggcc tataacacca acgggcaaag gcatgtaacc tataacattt   1920
tcacaacaag cgccaaatac gcggtcgtag tcataatttt tatatggtaa acgatcagat   1980
gctaatacag gagcttctgc caaaattgaa agagccttcc tacgtaccgc aaccgctctc   2040
gtagtatcac ctaatttttt ctccaaagcg tacaaaggta acttaccgtg aataaccaag   2100
gcagcgacct ctttgttctt caattgtttt gtatttccac tacttaataa tgcttctaat   2160
tcttctaaag gacgtatttt cttatccaag ctttcaatat cgcgggaatc atcttcctca   2220
ctagatgatg aaggtcctga tgagctcgat tgcgcagatg ataaactttt gactttcgat   2280
ccagaaatga ctgttttatt ggttaaaact ggtgtagaag cctttgtac aggagcagta    2340 aaagacttct tggtgacttc agtcttcacc aattggtctg cagccattat agttttttct   2400
ccttgacgtt aaagtataga ggtatattaa caatttttg ttgatacttt tatgacattt    2460
gaataagaag taatacaaac cgaaaatgtt gaaagtatta gttaaagtgg ttatgcagct   2520
tttgcattta tatctgtt aatagatcaa aaatcatcgc ttcgctgatt aattcccca     2580 gaaataaggc taaaaaacta atcgcattat tatcctatgg ttgttaattt gattcgttga   2640
tttgaaggtt tgtggggcca ggttactgcc aattttttcct cttcataacc ataaaagcta   2700
gtattgtaga atctttattg ttcggagcag tgcggcgcga ggcacatctg cgtttcagga   2760
acgcgaccgg tgaagaccag gacgcacgga ggagagtctt ccgtcggagg gctgtcgccc   2820
gctcggcggc ttctaatccg tacttcaata tagcaatgag cagttaagcg tattactgaa   2880
agttccaaag agaaggtttt tttaggctaa gataatgggg ctctttacat ttccacaaca   2940
tataagtaag attagatatg gatatgtata tggtggtatt gccatgtaat atgattatta   3000
aacttctttg cgtccatcca aaaaaaagt aagaattttt gaaaattcaa tataaatggc    3060
ttcagaaaaa gaaattagga gagagagatt cttgaacgtt ttccctaaat tagtagagga   3120
attgaacgca tcgcttttgg cttacggtat gcctaaggaa gcatgtgact ggtatgccca   3180
ctcattgaac tacaacactc caggcggtaa gctaaataga ggtttgtccg ttgtggacac   3240
gtatgctatt ctctccaaca agaccgttga acaattgggg caagaagaat acgaaaaggt   3300
tgccattcta ggttggtgca ttgagttgtt gcaggcttac ttcttggtcg ccgatgatat   3360
gatggacaag tccattacca gaagaggcca accatgttgg tacaaggttc ctgaagttgg   3420
```

| | |
|---|---|
| ggaaattgcc atcaatgacg cattcatgtt agaggctgct atctacaagc ttttgaaatc | 3480 |
| tcacttcaga aacgaaaaat actacataga tatcaccgaa ttgttccatg aggtcacctt | 3540 |
| ccaaaccgaa ttgggccaat tgatggactt aatcactgca cctgaagaca aagtcgactt | 3600 |
| gagtaagttc tccctaaaga agcactcctt catagttact ttcaagactg cttactattc | 3660 |
| tttctacttg cctgtcgcat tggccatgta cgttgccggt atcacggatg aaaaggattt | 3720 |
| gaaacaagcc agagatgtct tgattccatt gggtgaatac ttccaaattc aagatgacta | 3780 |
| cttagactgc ttcggtaccc cagaacagat cggtaagatc ggtacagata tccaagataa | 3840 |
| caaatgttct tgggtaatca acaaggcatt ggaacttgct tccgcagaac aaagaaagac | 3900 |
| tttagacgaa aattacggta agaaggactc agtcgcagaa gccaaatgca aaagattttt | 3960 |
| caatgacttg aaaattgaac agctatacca cgaatatgaa gagtctattg ccaaggattt | 4020 |
| gaaggccaaa atttctcagg tcgatgagtc tcgtggcttc aaagctgatg tcttaactgc | 4080 |
| gttcttgaac aaagtttaca agagaagcaa atagaactaa cgctaatcga taaaacatta | 4140 |
| gatttcaaac tagataagga ccatgtataa gaactatata cttccaatat aatatagtat | 4200 |
| aagctttaag atagtatctc tcgatctacc gttccacgtg actagtccaa ggattttttt | 4260 |
| taacccggga tatatgtgta ctttgcagtt atgacgccag atggcagtag tggaagatat | 4320 |
| tctttattga aaaatagctt gtcaccttac gtacaatctt gatccggagc ttttcttttt | 4380 |
| ttgccgatta agaattcggt cgaaaaaaga aaggagagg gccaagaggg agggcattgg | 4440 |
| tgactattga gcacgtgagt atacgtgatt aagcacacaa aggcagcttg gagtatgtct | 4500 |
| gttattaatt tcacaggtag ttctggtcca ttggtgaaag tttgcggctt gcagagcaca | 4560 |
| gaggccgcag aatgtgctct agattccgat gctgacttgc tgggtattat atgtgtgccc | 4620 |
| aatagaaaga gaacaattga cccggttatt gcaaggaaaa tttcaagtct tgtaaaagca | 4680 |
| tataaaaata gttcaggcac tccgaaatac ttggttggcg tgtttcgtaa tcaacctaag | 4740 |
| gaggatgttt tggctctggt caatgattac ggcattgata tcgtccaact gcatggagat | 4800 |
| gagtcgtggc aagaatacca agagttcctc ggtttgccag ttattaaaag actcgtattt | 4860 |
| ccaaaagact gcaacatact actcagtgca gcttcacaga aacctcattc gtttattccc | 4920 |
| ttgtttgatt cagaagcagg tgggacaggt gaacttttgg attggaactc gatttctgac | 4980 |
| tgggttggaa ggcaagagag ccccgaaagc ttacatttta tgttagctgg tggactgacg | 5040 |
| ccgtttaaac | 5050 |

<210> SEQ ID NO 51
<211> LENGTH: 6081
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 51

| | |
|---|---|
| gtttaaactt ttccaatagg tggttagcaa tcgtcttact ttctaacttt tcttaccttt | 60 |
| tacatttcag caatatatat atatatattt caaggatata ccattctaat gtctgcccct | 120 |
| aagaagatcg tcgttttgcc aggtgaccac gttggtcaag aaatcacagc cgaagccatt | 180 |
| aaggttctta agctatttc tgatgttcgt tccaatgtca agttcgattt cgaaaatcat | 240 |
| ttaattggtg gtgctgctat cgatgctaca ggtgttccac ttccagatga ggcgctggaa | 300 |
| gcctccaaga aggctgatgc cgtttttgtta ggtgctgtgg gtggtcctaa atgggtacc | 360 |

-continued

```
ggtagtgtta gacctgaaca aggtttacta aaaatccgta aagaacttca attgtacgcc      420
aacttaagac catgtaactt tgcatccgac tctcttttag acttatctcc aatcaagcca      480
caatttgcta aaggtactga cttcgttgtt gtcagagaat tagtgggagg tatttacttt      540
ggtaagagaa aggaagacgt ttagcttgcc tcgtccccgc cgggtcaccc ggccagcgac      600
atggaggccc agaataccct ccttgacagt cttgacgtgc gcagctcagg ggcatgatgt      660
gactgtcgcc cgtacattta gcccatacat ccccatgtat aatcatttgc atccatacat      720
tttgatggcc gcacggcgcg aagcaaaaat tacggctcct cgctgcagac ctgcgagcag      780
ggaaacgctc ccctcacaga cgcgttgaat tgtccccacg ccgcgcccct gtagagaaat      840
ataaaaggtt aggatttgcc actgaggttc ttctttcata tacttccttt taaaatcttg      900
ctaggataca gttctcacat cacatccgaa cataaacaac catggcagaa ccagcccaaa      960
aaaagcaaaa acaaactgtt caggagcgca aggcgtttat ctcccgtatc actaatgaaa     1020
ctaaaattca aatcgctatt tcgctgaatg gtggttatat tcaaataaaa gattcgattc     1080
ttcctgcaaa gaaggatgac gatgtagctt cccaagctac tcagtcacag gtcatcgata     1140
ttcacacagg tgttggcttt ttggatcata tgatccatgc gttggcaaaa cactctggtt     1200
ggtctcttat tgttgaatgt attggtgacc tgcacattga cgatcaccat actaccgaag     1260
attgcggtat cgcattaggg caagcgttca aagaagcaat gggtgctgtc cgtggtgtaa     1320
aaagattcgg tactgggttc gcaccattgg atgaggcgct atcacgtgcc gtagtcgatt     1380
tatctagtag accatttgct gtaatcgacc ttggattgaa gagagagatg attggtgatt     1440
tatccactga aatgattcca cacttttttgg aaagtttcgc ggaggcggcc agaattactt     1500
tgcatgttga ttgtctgaga ggtttcaacg atcaccacag aagtgagagt gcgttcaagg     1560
ctttggctgt tgccataaga gaagctattt ctagcaatgg caccaatgac gttccctcaa     1620
ccaaaggtgt tttgatgtga agtactgaca ataaaaagat tcttgttttc aagaacttgt     1680
catttgtata gttttttttat attgtagttg ttctatttta atcaaatgtt agcgtgattt     1740 atatttttt tcgcctcgac atcatctgcc cagatgcgaa gttaagtgcg cagaaagtaa     1800
tatcatgcgt caatcgtatg tgaatgctgg tcgctatact gctgtcgatt cgatactaac     1860
gccgccatcc acccgggttt ctcattcaag tggtaactgc tgttaaaatt aagatattta     1920
taaattgaag cttggtcgtt ccgaccaata ccgtagggaa acgtaaatta gctattgtaa     1980
aaaaaggaaa agaaaagaaa agaaaaatgt tacatatcga attgatctta ttcctttggt     2040
agaccagtct ttgcgtcaat caaagattcg tttgtttctt gtgggcctga accgacttga     2100
gttaaaatca ctctggcaac atccttttgc aactcaagat ccaattcacg tgcagtaaag     2160
ttagatgatt caaattgatg gttgaaagcc tcaagctgct cagtagtaaa tttcttgtcc     2220
catccaggaa cagagccaaa caatttatag ataaatgcaa agagtttcga ctcatttttca     2280 gctaagtagt acaacacagc atttggacct gcatcaaacg tgtatgcaac gattgtttct     2340
ccgtaaaact gattaatggt gtggcaccaa ctgatgatac gcttggaagt gtcattcatg     2400
tagaatattg gagggaaaga gtccaaacat gtggcatgga aagagttgga atccatcatt     2460
gtttcctttg caaggtggc gaaatctttt tcaacaatgg ctttacgcat gacttcaaat     2520
ctctttggta cgacatgttc aattcttcct ttaaatagtt cggaggttgc cacggtcaat     2580
tgcataccct gagtggaact cacatccttt ttaatatcgc tgacaactag gacacaagct     2640
ttcatctgag gccagtcaga gctgtctgcg atttgtactg ccatggaatc atgaccatct     2700
```

```
tcagcttttc ccatttccca ggccacgtat ccgccaaaca acgatctaca agctgaacca    2760
gacccctttc ttgctattct agatatttct gaagttgact gtggtaattg gtataactta    2820
gcaattgcag agaccaatgc agcaaagcca gcagcgagg aagctaaacc agctgctgta     2880
ggaaagttat tttcggagac aatgtggagt ttccattgag ataatgtggg caatgaggcg    2940
tccttcgatt ccatttcctt tcttaattgg cgtaggtcgc gcagacaatt ttgagttctt    3000
tcattgtcga tgctgtgtgg ttctccattt aaccacaaag tgtcgcgttc aaactcaggt    3060
gcagtagccg cagaggtcaa cgttctgagg tcatcttgcg ataaagtcac tgatatggac    3120
gaattggtgg gcagattcaa cttcgtgtcc cttttccccc aatacttaag ggttgcgatg    3180
ttgacgggtg cggtaacgga tgctgtgtaa acggtcatta gttttttc tccttgacgt      3240 taaagtatag aggtatatta acaatttttt gttgatactt tatgacatt tgaataagaa     3300 gtaatacaaa ccgaaaatgt tgaaagtatt agttaaagtg gttatgcagc ttttgcattt    3360
atatatctgt taatagatca aaaatcatcg cttcgctgat taattacccc agaaataagg    3420
ctaaaaaact aatcgcatta ttatcctatg gttgttaatt tgattcgttg atttgaaggt    3480
ttgtggggcc aggttactgc caattttcc tcttcataac cataaaagct agtattgtag      3540
aatctttatt gttcggagca gtgcggcgcg aggcacatct gcgtttcagg aacgcgaccg    3600
gtgaagacca ggacgcacgg aggagagtct tccgtcggag ggctgtcgcc cgctcggcgg    3660
cttctaatcc gtacttcaat atagcaatga gcagttaagc gtattactga agttccaaa     3720 gagaaggttt ttttaggcta agataatggg gctctttaca tttccacaac atataagtaa    3780
gattagatat ggatatgtat atggtggtat tgccatgtaa tatgattatt aaacttcttt    3840
gcgtccatcc aaaaaaaaag taagaatttt tgaaaattca atataaatgt cagagttgag    3900
agccttcagt gccccaggga aagcgttact agctggtgga tatttagttt tagatccgaa    3960
atatgaagca tttgtagtcg gattatcggc aagaatgcat gctgtagccc atccttacgg    4020
ttcattgcaa gagtctgata agtttgaagt gcgtgtgaaa agtaaacaat ttaaagatgg    4080
ggagtggctg taccatataa gtcctaaaac tggcttcatt cctgtttcga taggcggatc    4140 taagaacccct ttcattgaaa aagttatcgc taacgtattt agctacttta agcctaacat   4200
ggacgactac tgcaatagaa acttgttcgt tattgatatt ttctctgatg atgcctacca    4260
ttctcaggag gacagcgtta ccgaacatcg tggcaacaga agattgagtt ttcattcgca    4320
cagaattgaa gaagttccca aaacagggct gggctcctcg gcaggtttag tcacagtttt    4380
aactacagct ttggcctcct tttttgtatc ggacctggaa aataatgtag acaaatatag    4440
agaagttatt cataatttat cacaagttgc tcattgtcaa gctcagggta aaattggaag    4500
cgggtttgat gtagcggcgg cagcatatgg atctatcaga tatagaagat tcccacccgc    4560
attaatctct aatttgccag atattggaag tgctacttac ggcagtaaac tggcgcattt    4620
ggttaatgaa gaagactgga atataacgat taaaagtaac catttacctt cgggattaac    4680
tttatggatg ggcgatatta agaatggttc agaaacagta aaactggtcc agaaggtaaa    4740
aaattggtat gattcgcata tgccggaaag cttgaaaata tatacagaac tcgatcatgc    4800
aaattctaga tttatggatg gactatctaa actagatcgc ttacacgaga ctcatgacga    4860
ttacagcgat cagatatttg agtctcttga gaggaatgac tgtacctgtc aaaagtatcc    4920
tgagatcaca gaagttagag atgcagttgc cacaattaga cgttccttta gaaaaataac    4980
taaagaatct ggtgccgata tcgaacctcc cgtacaaact agcttattgg atgattgcca    5040
gaccttaaaa ggagttctta cttgcttaat acctggtgct ggtggttatg acgccattgc    5100
```

-continued

| | |
|---|---|
| agtgattgct aagcaagatg ttgatcttag ggctcaaacc gctgatgaca aaagattttc | 5160 |
| taaggttcaa tggctggatg taactcaggc tgactggggt gttaggaaag aaaaagatcc | 5220 |
| ggaaacttat cttgataaat aacttaaggt agataatagt ggtccatgtg acatctttat | 5280 |
| aaatgtgaag tttgaagtga ccgcgcttaa catctaacca ttcatcttcc gatagtactt | 5340 |
| gaaattgttc ctttcggcgg catgataaaa ttcttttaat gggtacaagc tacccgggaa | 5400 |
| agattctctt tttttatgat atttgtacat aaactttata aatgaaattc ataatagaaa | 5460 |
| cgacacgaaa ttacaaaatg gaatatgttc atagggtaga cgaaactata tacgcaatct | 5520 |
| acatacattt atcaagaagg agaaaaagga ggatgtaaag gaatacaggt aagcaaattg | 5580 |
| atactaatgg ctcaacgtga taaggaaaaa gaattgcact ttaacattaa tattgacaag | 5640 |
| gaggagggca ccacacaaaa agttaggtgt aacagaaaat catgaaacta tgattcctaa | 5700 |
| tttatatatt ggaggatttt ctctaaaaaa aaaaaatac aacaaataaa aaacactcaa | 5760 |
| tgacctgacc atttgatgga gtttaagtca ataccttctt gaaccatttc ccataatggt | 5820 |
| gaaagttccc tcaagaattt tactctgtca gaaacggcct taacgacgta gtcgacctcc | 5880 |
| tcttcagtac taaatctacc aataccaaat ctgatggaag aatgggctaa tgcatcatcc | 5940 |
| ttacccagcg catgtaaaac ataagaaggt tctagggaag cagatgtaca ggctgaaccc | 6000 |
| gaggataatg cgatatccct tagtgccatc aataaagatt ctccttccac gtaggcgaaa | 6060 |
| gaaacgttaa cacgtttaaa c | 6081 |

<210> SEQ ID NO 52
<211> LENGTH: 4933
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

| | |
|---|---|
| gtttaaacta ctcagtatat taagtttcga attgaagggc gaactcttat tcgaagtcgg | 60 |
| agtcaccaca acacttccgc ccatactctc cgaatcctcg tttcctaaag taagtttact | 120 |
| tccacttgta ggcctattat taatgatatc tgaataatcc tctattaggg ttggatcatt | 180 |
| cagtagcgcg tgcgattgaa aggagtccat gcccgacgtc gacgtgatta gcgaaggcgc | 240 |
| gtaaccattg tcatgtctag cagctataga actaacctcc ttgacaccac ttgcggaagt | 300 |
| ctcatcaaca tgctcttcct tattactcat tctcttacca agcagagaat gttatctaaa | 360 |
| aactacgtgt atttcacctc tttctcgact tgaacacgtc caactcctta agtactacca | 420 |
| cagccaggaa agaatggatc cagttctaca cgatagcaaa gcagaaaaca caaccagcgt | 480 |
| acccctgtag aagcttcttt gtttacagca cttgatccat gtagccatac tcgaaatttc | 540 |
| aactcatctg aaacttttcc tgaaggttga aaaagaatgc ataagggtc acccgaagct | 600 |
| tattcacgcc cgggagttat gacaattaca acaacagaat tctttctata tatgcacgaa | 660 |
| cttgtaatat ggaagaaatt atgacgtaca aactataaag taaatatttt acgtaacaca | 720 |
| tggtgctgtt gtgcttcttt ttcaagagaa taccaatgac gtatgactaa gtttaggatt | 780 |
| taatgcaggt gacggaccca tctttcaaac gatttatatc agtggcgtcc aaattgttag | 840 |
| gttttgttgg ttcagcaggt ttcctgttgt gggtcatatg actttgaacc aaatggccgg | 900 |
| ctgctagggc agcacataag gataattcac ctgccaagac ggcacaggca actattcttg | 960 |
| ctaattgacg tgcgttggta ccaggagcgg tagcatgtgg gcctcttaca cctaataagt | 1020 |

```
ccaacatggc accttgtggt tctagaacag taccaccacc gatggtacct acttcgatgg    1080
atggcatgga tacggaaatt ctcaaatcac cgtccacttc tttcatcaat gttatacagt    1140
tggaactttc gacattttgt gcaggatctt gtcctaatgc caagaaaaca gctgtcacta    1200
aattagctgc atgtgcgtta atccaccaa cagacccagc cattgcagat ccaaccaaat     1260
tcttagcaat gttcaactca accaatgcgg aaacatcact ttttaacact tttctgacaa    1320
catcaccagg aatagtagct tctgcgacga cactcttacc acgaccttcg atccagttga    1380
tggcagctgg tttttttgtcg gtacagtagt taccagaaac ggagacaacc tccatatctt   1440
cccagccata ctcttctacc atttgcttta atgagtattc gacaccctta gaaatcatat    1500
tcatacccat tgcgtcacca gtagttgttc taaatctcat gaagagtaaa tctcctgcta    1560
gacaagtttg aatatgttgc agacgtgcaa atcttgatgt agagttaaaa gcttttttaa    1620
ttgcgttttg tccctcttct gagtctaacc atatcttaca ggaccagat cttttcaaag     1680
ttgggaaacg gactactggg cctcttgtca taccatcctt agttaaaaca gttgttgcac    1740
caccgccagc attgattgcc ttacagccac gcatggcaga agctaccaaa caaccctctg    1800
tagttgccat tggtatatga aagatgtac catcgataac caaggggcct ataacaccaa     1860
cgggcaaagg catgtaacct ataacatttt cacaacaagc gccaaatacg cggtcgtagt    1920
cataatttt atatggtaaa cgatcagatg ctaatacagg agcttctgcc aaaattgaaa     1980
gagccttcct acgtaccgca accgctctcg tagtatcacc taatttttc tccaaagcgt     2040
acaaggtaa cttaccgtga ataaccaagg cagcgacctc tttgttcttc aattgttttg     2100
tatttccact acttaataat gcttctaatt cttctaaagg acgtattttc ttatccaagc    2160
tttcaatatc gcgggaatca tcttcctcac tagatgatga aggtcctgat gagctcgatt    2220
gcgcagatga taaacttttg actttcgatc cagaaatgac tgttttattg gttaaaactg    2280
gtgtagaagc cttttgtaca ggagcagtaa aagacttctt ggtgacttca gtcttccacca   2340
attggtctgc agccattata gttttttctc cttgacgtta aagtatagag gtatattaac    2400
aatttttgt tgatacttt atgacatttg aataagaagt aatacaaacc gaaaatgttg      2460
aaagtattag ttaaagtggt tatgcagctt ttgcatttat atatctgtta atagatcaaa    2520
aatcatcgct tcgctgatta attacccag aaataaggct aaaaaactaa tcgcattatt     2580
atcctatggt tgttaatttg attcgttgat ttgaaggttt gtggggccag ttactgcca     2640
attttttcctc ttcataacca taaaagctag tattgtagaa tctttattgt tcggagcagt   2700
gcggcgcgag gcacatctgc gtttcaggaa cgcgaccggt gaagaccagg acgcacggag    2760
gagagtcttc cgtcggaggg ctgtcgcccg ctcggcggct tctaatccgt acttcaatat    2820
agcaatgagc agttaagcgt attactgaaa gttccaagaa gaaggttttt ttaggctaag    2880
ataatgggggc tctttacatt tccacaacat ataagtaaga ttagatatgg atatgtatat   2940
ggtggtattg ccatgtaata tgattattaa acttctttgc gtccatccaa aaaaaaagta    3000
agaattttttg aaaattcaat ataaatgact gccgacaaca atagtatgcc ccatggtgca   3060
gtatctagtt acgccaaatt agtgcaaaac caaacacctg aagacatttt ggaagagttt    3120
cctgaaatta ttccattaca acaaagacct aatacccgat ctagtgagac gtcaaatgac    3180
gaaagcggag aaacatgttt ttctggtcat gatgaggagc aaattaagtt aatgaatgaa    3240
aattgtattg ttttggattg ggacgataat gctattggtg ccggtaccaa gaaagtttgt    3300
catttaatgg aaaatattga aaagggttta ctacatcgtg cattctccgt ctttattttc    3360
```

| | |
|---|---|
| aatgaacaag gtgaattact tttacaacaa agagccactg aaaaaataac tttccctgat | 3420 |
| ctttggacta acacatgctg ctctcatcca ctatgtattg atgacgaatt aggtttgaag | 3480 |
| ggtaagctag acgataagat taagggcgct attactgcgg cggtgagaaa actagatcat | 3540 |
| gaattaggta ttccagaaga tgaaactaag acaaggggta agtttcactt tttaaacaga | 3600 |
| atccattaca tggcaccaag caatgaacca tggggtgaac atgaaattga ttacatccta | 3660 |
| ttttataaga tcaacgctaa agaaaacttg actgtcaacc caaacgtcaa tgaagttaga | 3720 |
| gacttcaaat gggtttcacc aaatgatttg aaaactatgt tgctgaccc aagttacaag | 3780 |
| tttacgcctt ggtttaagat tatttgcgag aattacttat tcaactggtg ggagcaatta | 3840 |
| gatgaccttt ctgaagtgga aaatgacagg caaattcata gaatgctata acaacgcgtc | 3900 |
| aataatatag gctacataaa aatcataata actttgttat catagcaaaa tgtgatataa | 3960 |
| aacgtttcat ttcacctgaa aaatagtaaa aataggcgac aaaaatcctt agtaatatgt | 4020 |
| aaactttatt ttctttattt acccgggagt cagtctgact cttgcgagag atgaggatgt | 4080 |
| aataatacta atctcgaaga tgccatctaa tacatataga catacatata tatatatata | 4140 |
| cattctatat attcttaccc agattctttg aggtaagacg gttgggtttt atcttttgca | 4200 |
| gttggtacta ttaagaacaa tcgaatcata agcattgctt acaaagaata cacatacgaa | 4260 |
| atattaacga taatgtcaat tacgaagact gaactggacg gtatattgcc attggtggcc | 4320 |
| agaggtaaag ttagagacat atatgaggta gacgctggta cgttgctgtt tgttgctacg | 4380 |
| gatcgtatct ctgcatatga cgttattatg gaaaacagca ttcctgaaaa ggggatccta | 4440 |
| ttgaccaaac tgtcagagtt ctggttcaag ttcctgtcca acgatgttcg taatcatttg | 4500 |
| gtcgacatcg ccccaggtaa gactattttc gattatctac ctgcaaaatt gagcgaacca | 4560 |
| aagtacaaaa cgcaactaga agaccgctct ctattggttc acaaacataa actaattcca | 4620 |
| ttggaagtaa ttgtcagagg ctacatcacc ggatctgctt ggaaagagta cgtaaaaaca | 4680 |
| ggtactgtgc atggtttgaa acaacctcaa ggacttaaag aatctcaaga gttcccagaa | 4740 |
| ccaatcttca ccccatcgac caaggctgaa caaggtgaac atgacgaaaa catctctcct | 4800 |
| gcccaggccg ctgagctggt gggtgaagat ttgtcacgta gagtggcaga actggctgta | 4860 |
| aaactgtact ccaagtgcaa agattatgct aaggagaagg gcatcatcat cgcagacact | 4920 |
| aaaattgttta aac | 4933 |

<210> SEQ ID NO 53
<211> LENGTH: 8425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatcga ctacgtcgta aggccgtttc tgacagagta aaattcttga gggaactttc | 240 |
| accattatgg gaaatgcttc aagaaggtat tgacttaaac tccatcaaat ggtcaggtca | 300 |
| ttgagtgttt tttatttgtt gtattttttt tttttagag aaaatcctcc aatatcaaat | 360 |
| taggaatcgt agtttcatga ttttctgtta cacctaactt tttgtgtggt gccctcctcc | 420 |

```
ttgtcaatat taatgttaaa gtgcaattct ttttccttat cacgttgagc cattagtatc    480
aatttgctta cctgtattcc tttactatcc tccttttttct ccttcttgat aaatgtatgt    540
agattgcgta tatagtttcg tctaccctat gaacatattc cattttgtaa tttcgtgtcg    600
tttctattat gaatttcatt tataaagttt atgtacaaat atcataaaaa aagagaatct    660
ttttaagcaa ggattttctt aacttcttcg gcgacagcat caccgacttc ggtggtactg    720
ttggaaccac ctaaatcacc agttctgata cctgcatcca aaacctttttt aactgcatct    780 tcaatggcct taccttcttc aggcaagttc aatgacaatt tcaacatcat tgcagcagac    840
aagatagtgg cgatagggtc aaccttattc tttggcaaat ctggagcaga accgtggcat    900
ggttcgtaca aaccaaatgc ggtgttcttg tctggcaaag aggccaagga cgcagatggc    960
aacaaaccca aggaacctgg gataacggag gcttcatcgg agatgatatc accaaacatg   1020
ttgctggtga ttataatacc atttaggtgg gttgggttct taactaggat catggcggca   1080
gaatcaatca attgatgttg aaccttcaat gtagggaatt cgttcttgat ggtttcctcc   1140 acagttttc tccataatct tgaagaggcc aaaagattag ctttatccaa ggaccaaata   1200
ggcaatggtg gctcatgttg tagggccatg aaagcggcca ttcttgtgat tctttgcact   1260
tctggaacgg tgtattgttc actatcccaa gcgacaccat caccatcgtc ttcctttctc   1320
ttaccaaagt aaatacctcc cactaattct ctgacaacaa cgaagtcagt acctttagca   1380
aattgtggct tgattggaga taagtctaaa agagagtcgg atgcaaagtt acatggtctt   1440
aagttggcgt acaattgaag ttcttttacgg attttttagta aaccttgttc aggtctaaca   1500
ctaccggtac cccatttagg accagccaca gcacctaaca aaacggcatc aaccttcttg   1560
gaggcttcca gcgcctcatc tggaagtggg acacctgtag catcgatagc agcaccacca   1620
attaaatgat tttcgaaatc gaacttgaca ttggaacgaa catcagaaat agctttaaga   1680
accttaatgg cttcggctgt gatttcttga ccaacgtggt cacctggcaa aacgacgatc   1740
ttcttagggg cagacattac aatggtatat ccttgaaata tatataaaaa aaggcgcctt   1800
agaccgctcg gccaaacaac caattacttg ttgagaaata gagtataatt atcctataaa   1860
tataacgttt ttgaacacac atgaacaagg aagtacagga caattgattt tgaagagaat   1920
gtggattttg atgtaattgt tgggattcca ttttttaataa ggcaataata ttaggtatgt   1980
ggatatacta gaagttctcc tcgaccgtcg atatgcggtg tgaaataccg cacagatgcg   2040
taaggagaaa ataccgcatc aggaaattgt aaacgttaat attttgttaa aattcgcgtt   2100 aaattttgt taaatcagct cattttttaa ccaataggcc gaaatcggca aaatccctta   2160
taaatcaaaa gaatagaccg agatagggtt gagtgttgtt ccagtttgga acaagagtcc   2220
actattaaag aacgtggact ccaacgtcaa agggcgaaaa accgtctatc agggcgatgg   2280
cccactacgt ggaagatccg aggcctagct ttaacgaacg cagaattttc gagttattaa   2340
acttaaaata cgctgaaccc gaacatagaa atatcgaatg gaaaaaaaa actgcataaa   2400 ggcattaaaa gaggagcgaa ttttttttta ataaaaatct taataatcat taaaagataa   2460
ataatagtct atatatacgt atataaataa aaaatattca aaaaataaaa taaactatta   2520
ttttagcgta aaggatgggg aaagagaaaa gaaaaaaatt gatctatcga tttcaattca   2580
attcaattta tttcttttcg gataagaaag caacacctgg caattcctta ccttccaata   2640
attccaaaga agcaccacca ccagtagaga catgggagac ccgggccatg gttagataga   2700
catagggtaa actagcaatg atttgatcaa atgcttgtat tcatctccca ttctcgtaaa   2760
attgtcttta cctgcatatt ggacctctaa aaattggcaa agatatataa cagccataag   2820
```

```
taaaggtctt gggatattct tgttgttaa atactctctg tttatgtctt tccaaacgtc    2880
ctccacttcc ttataaatca gtgtctgagc atattcttcg ttgacattgt attccttcat    2940
gtaagattct aaagagcttg aactatgttt tctctcctgt tccgctttat gagtcatcag    3000
gtcatttaat ctcctaccca gaataccact gtaacggaat aaaggcggag cagatacagc    3060
ccactcaact gattccttag tgaaaatatc gctcattcct agataacagg tagttgttag    3120
caagtttgca ccaccagtga taataactac gggatcgtgc tcttcagttg tcggtatgtg    3180
tccttcatta gcccatttcg cttctaccat tagattcctt acgaattctt taacgaactc    3240
cttcccacag ttgaataaat cagttctacc ttctttggcc agaaactcct ccatttctgt    3300
gtaggtatcc atgaataatt tgtaaatagg cttcatgtat tccggcaacg tgtctaagca    3360
ggtgatcgac catctttcca cggcttcagt gaaaatcttt aactcctcgt aagttccata    3420
tgcgtcatac gtgtcatcaa taagtgttat cacagcaact gccttagtga aaaaaactct    3480
agctcttgaa tactggggtt cgtaaccaga acctaaaccc caaaaatagc attcaacgat    3540
acgatctctc agacatgggg cattttttctt aatatcaaat gccttccacc acttgcatac    3600
gtgactcaac tcttccttat gtaggctctg caatagattg aactccagtt tagctaactt    3660
tagcagagtt ttattatggg agtcttgttg ctgatagaag ggtatgtact gggcggcctc    3720
gatccttggc aatctcttcc acaatggttg ctttaaagct ctctggatttt cagtgaataa    3780 agcggggttt gtactaaacg cgtcctttgt cataatcgat agccttgatc ttgtgaatcc    3840
cagggcatct tcaagaatta tttcgcccgg aactctcatg gacgtagcct catataattc    3900
caacaatcct tcaacatcat cgctaacga ttgtttaaaa gcaccattct tgtctttata    3960
gttattaaac acatcacacg tgacatagta tccttgttta cgcatcagcc taaaccataa    4020
gctagacctg tcgccattcc aattatcacc ataggtctcg taaatacatt gcaatgcatg    4080
atcaatttca cgttcaaaat gatacggaat acctaaacgt tgaatctcgt caatcagctt    4140
caacaaattt gcatgtttca taggaatatc caatgcttcc tttaacaact gtcttacttc    4200
cttctttaga tcgtttacta tttgctccac accctgttca acttgtttct cataaatcaa    4260
aaattgatcg ccccaaatag aaggtgggaa atttgcaatt ggccttatag gtttctcttc    4320
agtcaaggcc attgttttct gcagatccgg ggttttttct ccttgacgtt aaagtataga    4380
ggtatattaa caattttttg ttgatacttt tattacattt gaataagaag taatacaaac    4440
cgaaaatgtt gaaagtatta gttaaagtgg ttatgcagtt tttgcattta tatatctgtt    4500
aatagatcaa aaatcatcgc ttcgctgatt aattacccca gaataaggc taaaaaacta    4560 atcgcattat catcctatgg ttgttaattt gattcgttca tttgaaggtt tgtggggcca    4620
ggttactgcc aatttttcct cttcataacc ataaaagcta gtattgtaga atctttattg    4680
ttcggagcag tgcggcgcga ggcacatctg cgtttcagga acgcgaccgg tgaagacgag    4740
gacgcacgga ggagagtctt ccttcggagg gctgtcaccc gctcggcggc ttctaatccg    4800
tactaagatc tgctttaatt tggccggcga acgtggcgag aaaggaaggg aagaaagcga    4860
aaggagcggg cgctagggcg ctggcaagtg tagcggtcac gctgcgcgta accaccacac    4920
ccgccgcgct taatgcgccg ctacagggcg cgtcgcgcca ttcgccattc aggctgcgca    4980
actgttggga agggcgatcg gtgcgggcct cttcgctatt acgccagctg cattaatgaa    5040
tcggccaacg cgcggggaga ggcggtttgc gtattgggcg ctcttccgct tcctcgctca    5100
ctgactcgct gcgctcggtc gttcggctgc ggcgagcggt atcagctcac tcaaaggcgg    5160
```

```
taatacggtt atccacagaa tcagggata acgcaggaaa gaacatgtga gcaaaaggcc    5220
agcaaaaggc caggaaccgt aaaaaggccg cgttgctggc gttttttccat aggctccgcc   5280 cccctgacga gcatcacaaa aatcgacgct caagtcagag gtggcgaaac ccgacaggac    5340
tataaagata ccaggcgttt ccccctggaa gctccctcgt gcgctctcct gttccgaccc    5400
tgccgcttac cggatacctg tccgcctttc tcccttcggg aagcgtggcg ctttctcata    5460
gctcacgctg taggtatctc agttcggtgt aggtcgttcg ctccaagctg gctgtgtgc    5520 acgaaccccc cgttcagccc gaccgctgcg ccttatccgg taactatcgt cttgagtcca    5580
acccggtaag acacgactta tcgccactgg cagcagccac tggtaacagg attagcagag    5640
cgaggtatgt aggcggtgct acagagttct tgaagtggtg gcctaactac ggctacacta    5700
gaaggacagt atttggtatc tgcgctctgc tgaagccagt taccttcgga aaaagagttg    5760
gtagctcttg atccggcaaa caaaccaccg ctggtagcgg tggttttttt gtttgcaagc    5820
agcagattac gcgcagaaaa aaaggatctc aagaagatcc tttgatcttt tctacggggt    5880
ctgacgctca gtggaacgaa aactcacgtt aagggatttt ggtcatgaga ttatcaaaaa    5940
ggatcttcac ctagatcctt ttaaattaaa aatgaagttt taaatcaatc taagtatat    6000 atgagtaaac ttggtctgac agttaccaat gcttaatcag tgaggcacct atctcagcga    6060
tctgtctatt tcgttcatcc atagttgcct gactccccgt cgtgtagata actacgatac    6120
gggagggctt accatctggc cccagtgctg caatgatacc gcgagaccca cgctcaccgg    6180
ctccagattt atcagcaata aaccagccag ccggaagggc cgagcgcaga agtggtcctg    6240
caactttatc cgcctccatc cagtctatta attgttgccg ggaagctaga gtaagtagtt    6300
cgccagttaa tagtttgcgc aacgttgttg ccattgctac aggcatcgtg gtgtcacgct    6360
cgtcgtttgg tatggcttca ttcagctccg gttcccaacg atcaaggcga gttacatgat    6420
cccccatgtt gtgcaaaaaa gcggttagct ccttcggtcc tccgatcgtt gtcagaagta    6480
agttggccgc agtgttatca ctcatggtta tggcagcact gcataattct cttactgtca    6540
tgccatccgt aagatgcttt tctgtgactg gtgagtactc aaccaagtca ttctgagaat    6600
agtgtatgcg gcgaccgagt tgctcttgcc cggcgtcaat acgggataat accgcgccac    6660
atagcagaac tttaaaagtg ctcatcattg gaaaacgttc ttcggggcga aaactctcaa    6720
ggatcttacc gctgttgaga tccagttcga tgtaacccac tcgtgcaccc aactgatctt    6780
cagcatcttt tactttcacc agcgtttctg ggtgagcaaa aacaggaagg caaaatgccg    6840
caaaaaaggg aataagggcg acacggaaat gttgaatact catactcttc cttttttcaat   6900 attattgaag catttatcag ggttattgtc tcatgagcgg atacatattt gaatgtattt    6960
agaaaaataa acaaataggg gttccgcgca catttccccg aaaagtgcca cctgaacgaa    7020
gcatctgtgc ttcattttgt agaacaaaaa tgcaacgcga gagcgctaat ttttcaaaca    7080
aagaatctga gctgcatttt tacagaacag aaatgcaacg cgaaagcgct attttaccaa    7140
cgaagaatct gtgcttcatt tttgtaaaac aaaaatgcaa cgcgagagcg ctaattttc    7200 aaacaaagaa tctgagctgc atttttacag aacagaaatg caacgcgaga gcgctatttt    7260
accaacaaag aatctatact ctttttttgt tctacaaaaa tgcatcccga gagcgctatt    7320
tttctaacaa agcatcttag attactttt ttctcctttg tgcgctctat aatgcagtct    7380
cttgataact ttttgcactg taggtccgtt aaggttagaa gaaggctact ttggtgtcta    7440
ttttctcttc cataaaaaaa gcctgactcc acttcccgcg tttactgatt actagcgaag   7500
ctgcgggtgc attttttcaa gataaaggca tccccgatta tattctatac cgatgtggat    7560
```

```
tgcgcatact ttgtgaacag aaagtgatag cgttgatgat tcttcattgg tcagaaaatt      7620
atgaacggtt tcttctattt tgtctctata tactacgtat aggaaatgtt tacattttcg      7680
tattgttttc gattcactct atgaatagtt cttactacaa ttttttttgtc taaagagtaa     7740 tactagagat aaacataaaa aatgtagagg tcgagtttag atgcaagttc aaggagcgaa      7800
aggtggatgg gtaggttata tagggatata gcacagagat atatagcaaa gagatacttt      7860
tgagcaatgt ttgtggaagc ggtattcgca atattttagt agctcgttac agtccggtgc      7920 gttttttggtt ttttgaaagt gcgtcttcag agcgcttttg gttttcaaaa gcgctctgaa     7980
gttcctatac tttctagaga ataggaactt cggaatagga acttcaaagc gtttccgaaa      8040
acgagcgctt ccgaaaatgc aacgcgagct gcgcacatac agctcactgt tcacgtcgca      8100
cctatatctg cgtgttgcct gtatatatat atacatgaga agaacggcat agtgcgtgtt      8160
tatgcttaaa tgcgtactta tatgcgtcta tttatgtagg atgaaaggta gtctagtacc      8220
tcctgtgata ttatcccatt ccatgcgggg tatcgtatgc ttccttcagc actaccctt      8280 agctgttcta tatgctgcca ctcctcaatt ggattagtct catccttcaa tgctatcatt     8340
tcctttgata ttggatcata ctaagaaacc attattatca tgacattaac ctataaaaat     8400
aggcgtatca cgaggcccttt tcgtc                                           8425

<210> SEQ ID NO 54
<211> LENGTH: 13280
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
tcgcgcgttt cggtgatgac ggtgaaaacc tctgacacat gcagctcccg gagacggtca        60
cagcttgtct gtaagcggat gccggagca gacaagcccg tcagggcgcg tcagcgggtg       120
ttggcgggtg tcggggctgg cttaactatg cggcatcaga gcagattgta ctgagagtgc      180
accatatcga ctacgtcgta aggccgtttc tgacagagta aaattcttga gggaactttc      240
accattatgg gaaatgcttc aagaaggtat tgacttaaac tccatcaaat ggtcaggtca      300
ttgagtgttt tttatttgtt gtatttttt ttttttagag aaaatcctcc aatatcaaat       360
taggaatcgt agtttcatga ttttctgtta caccttaactt tttgtgtggt gccctcctcc     420
ttgtcaatat taatgttaaa gtgcaattct ttttccttat cacgttgagc cattagtatc      480
aatttgctta cctgtattcc tttactatcc tccttttct ccttcttgat aaatgtatgt       540
agattgcgta tatagtttcg tctaccctat gaacatattc cattttgtaa tttcgtgtcg      600
tttctattat gaatttcatt ataaagtttt atgtacaaat atcataaaaa aagagaatct      660
ttttaagcaa ggattttctt aacttcttcg gcgacagcat caccgacttc ggtggtactg      720
ttggaaccac ctaaatcacc agttctgata cctgcatcca aaccttttt aactgcatct       780 tcaatggcct taccttcttc aggcaagttc aatgacaatt tcaacatcat tgcagcagac      840
aagatagtgg cgatagggtc aaccttattc tttggcaaat ctggagcaga accgtggcat      900
ggttcgtaca aaccaaatgc ggtgttcttg tctggcaaag aggccaagga cgcagatggc      960
aacaaaccca aggaacctgg gataacggag gcttcatcgg agatgatatc accaaacatg     1020
ttgctggtga ttataatacc atttaggtgg gttgggttct taactaggat catggcggca     1080
gaatcaatca attgatgttg aaccttcaat gtagggaatt cgttcttgat ggtttcctcc     1140
```

```
acagtttttc tccataatct tgaagaggcc aaaagattag ctttatccaa ggaccaaata    1200
ggcaatggtg gctcatgttg tagggccatg aaagcggcca ttcttgtgat tctttgcact    1260
tctggaacgg tgtattgttc actatcccaa gcgacaccat caccatcgtc ttcctttctc    1320
ttaccaaagt aaatacctcc cactaattct ctgacaacaa cgaagtcagt acctttagca    1380
aattgtggct tgattggaga taagtctaaa agagagtcgg atgcaaagtt acatggtctt    1440
aagttggcgt acaattgaag ttcttttacgg attttttagta aaccttgttc aggtctaaca    1500
ctaccggtac cccatttagg accagccaca gcacctaaca aaacggcatc aaccttcttg    1560
gaggcttcca gcgcctcatc tggaagtggg acacctgtag catcgatagc agcaccacca    1620
attaaatgat tttcgaaatc gaacttgaca ttggaacgaa catcagaaat agctttaaga    1680
accttaatgg cttcggctgt gatttcttga ccaacgtggt cacctggcaa aacgacgatc    1740
ttcttagggg cagacattac aatggtatat ccttgaaata tatataaaaa aaggcgcctt    1800
agaccgctcg gccaaacaac caattacttg ttgagaaata gagtataatt atcctataaa    1860
tataacgttt ttgaacacac atgaacaagg aagtacagga caattgattt tgaagagaat    1920
gtggattttg atgtaattgt tgggattcca ttttttaataa ggcaataata ttaggtatgt    1980
ggatatacta gaagttctcc tcgaccgtcg atatgcggtg tgaaataccg cacagatgcg    2040
taaggagaaa ataccgcatc aggaaaattgt aaacgttaat attttgttaa aattcgcgtt    2100
aaattttttgt taaatcagct cattttttaa ccaataggcc gaaatcggca aaatccctta    2160
taaatcaaaa gaatagaccg agataggggtt gagtgttgtt ccagtttgga acaagagtcc    2220
actattaaag aacgtggact ccaacgtcaa agggcgaaaa accgtctatc agggcgatgg    2280
cccactacgt ggaagatccg aggcctagct ttaacgaacg cagaattttc gagttattaa    2340
acttaaaata cgctgaaccc gaacatagaa atatcgaatg ggaaaaaaaa actgcataaa    2400
ggcattaaaa gaggagcgaa ttttttttta ataaaaatct taataatcat taaaagataa    2460
ataatagtct atatatacgt atataaataa aaaatattca aaaaataaaa taaactatta    2520
ttttagcgta aaggatgggg aaagagaaaa gaaaaaaatt gatctatcga tttcaattca    2580
attcaattta tttcttttcg gataagaaag caacacctgg caattcctta ccttccaata    2640
attccaaaga agcaccacca ccagtagaga catgggagac ccgggccatg ttagatagaa    2700
cataggggtaa actagcaatg atttgatcaa atgcttgtat tcatctccca ttctcgtaaa    2760
attgtctttta cctgcatatt ggacctctaa aaattggcaa agatatataa cagccataag    2820
taaaggtctt gggatattct ttgttgttaa atactctctg tttatgtctt tccaaacgtc    2880
ctccacttcc ttataaatca gtgtctgagc atattcttcg ttgacattgt attccttcat    2940
gtaagattct aaagagcttg aactatgttt tctctcctgt tccgctttat gagtcatcag    3000
gtcatttaat ctcctaccca gaataccact gtaacgaat aaaggcggag cagatacagc    3060
ccactcaact gattccttag tgaaaatatc gctcattcct agataacagg tagttgttag    3120
caagtttgca ccaccagtga taataactac gggatcgtgc tcttcagttg tcggtatgtg    3180
tccttcatta gcccatttcg cttctaccat tagattcctt acgaattctt taacgaactc    3240
cttcccacag ttgaataaat cagttctacc ttctttggcc agaaactcct ccatttctgt    3300
gtaggtatcc atgaataatt tgtaaatagg cttcatgtat tccggcaacg tgtctaagca    3360
ggtgatcgac catctttcca cggcttcagt gaaaatcttt aactcctcgt aagttccata    3420
tgcgtcatac gtgtcatcaa taagtgttat cacagcaact gccttagtga aaaaaactct    3480
```

```
agctcttgaa tactggggtt cgtaaccaga acctaaaccc caaaaatagc attcaacgat    3540
acgatctctc agacatgggg cattttttctt aatatcaaat gccttccacc acttgcatac   3600
gtgactcaac tcttccttat gtaggctctg caatagattg aactccagtt tagctaactt    3660
tagcagagtt ttattatggg agtcttgttg ctgatagaag ggtatgtact gggcggcctc    3720
gatccttggc aatctcttcc acaatggttg ctttaaagct ctctggattt cagtgaataa    3780
agcggggttt gtactaaacg cgtcctttgt cataatcgat agccttgatc ttgtgaatcc    3840
cagggcatct tcaagaatta tttcgcccgg aactctcatg gacgtagcct catataattc    3900
caacaatcct tcaacatcat tcgctaacga ttgtttaaaa gcaccattct tgtctttata    3960
gttattaaac acatcacacg tgacatagta tccttgttta cgcatcagcc taaaccataa    4020
gctagacctg tcgccattcc aattatcacc ataggtctcg taaatacatt gcaatgcatg    4080
atcaatttca cgttcaaaat gatacggaat acctaaacgt tgaatctcgt caatcagctt    4140
caacaaattt gcatgtttca taggaatatc caatgcttcc tttaacaact gtcttacttc    4200
cttctttaga tcgtttacta tttgctccac accctgttca acttgttttct cataaatcaa    4260
aaattgatcg ccccaaatag aaggtgggaa atttgcaatt ggccttatag gtttctcttc    4320
agtcaaggcc attgttttct gcagatccgg ggttttttct ccttgacgtt aaagtataga    4380
ggtatattaa caatttttg ttgatacttt tattacattt gaataagaag taatacaaac    4440
cgaaaatgtt gaaagtatta gttaaagtgg ttatgcagtt tttgcattta tatatctgtt    4500
aatagatcaa aaatcatcgc ttcgctgatt aattacccca gaaataaggc taaaaaacta    4560
atcgcattat catcctatgg ttgttaattt gattcgttca tttgaaggtt tgtggggcca    4620
ggttactgcc aatttttcct cttcataacc ataaaagcta gtattgtaga atctttattg    4680
ttcggagcag tgcggcgcga ggcacatctg cgtttcagga acgcgaccgg tgaagacgag    4740
gacgcacgga ggagagtctt ccttcggagg gctgtcaccc gctcggcggc ttctaatccg    4800
tactaagatc tgctttaatt tggccggcga acgtggcgag aaaggaaggg aagaaagcga    4860
aaggagcggg cgctagggcg ctggcaagtg tagcggtcac gctgcgcgta accaccacac    4920
ccgccgcgct taatgcgccg ctacagggcg cgtcgcgcca ttcgccattc aggctgcgca    4980
actgttggga agggcgatcg gtgcgggcct cttcgctatt acgccagctg aattggagcg    5040
acctcatgct atacctgaga agcaacctg acctacagga aagagttact caagaataag    5100
aattttcgtt ttaaaaccta agagtcactt taaaatttgt atacacttat ttttttata    5160
acttatttaa taataaaaat cataaatcat aagaaattcg cttatttaga agtgtcaaca    5220
acgtatctac caacgatttg acccttttcc atcttttcgt aaatttctgg caaggtagac    5280
aagccgacaa ccttgattgg agacttgacc aaacctctgg cgaagaattg ttaattaaga    5340
gtcagtcgac ttaaaaacta gggaccaata gcaattctgt tttacgttgc attgttgcac    5400
ctgaactttc cgtcatgtca atttgatcat atgaaactcc attgggcaac ttccagttga    5460
aatgataaag aatgttggct agtggcagtt gaacattggc caaacctaac gcagcgccag    5520
gacacatacg acgtccagcc ccaaatggta aatattcata ttcggcgccc atcactgttg    5580
ccgaagagtt ttcaaatctt tcaggtataa acgcttctgc atccttccag tattcaggat    5640
ctctattgat cgcaaacaca ttaacgatta atttcgtttt gttagggata ttataaccag    5700
ccaagtttac tggctgacga cattctctag gtagcactaa cggcaagggt gggtgtagtc    5760
taagagtctc tttgatgacc atattcaagt aggacaattc ttgtatatct tcttcatgta    5820
ttttttcttt cccattcaag gccttacgta attcagcctg aacctttcc attgctttcg    5880
```

```
gacattttat tagctcgctt atagcccatt ctatggtaga acttgaagtg tcggtccctg   5940
caccgaacat gtccaaaatt attgctttga tattatccga agtcagagga aactcagcag   6000
aatcctttaa tctaagtaat acatctaata gggtttcgtt ggttttggat gacgtattta   6060
cggtatgttc agctaccaaa ttgtcaatta agttatcaat cttttttacgt aggctagtta   6120 atcttgctct cttaccgctc aagtgatgca agaacttttt agatgggaaa atatcggcaa   6180
catcgaaacc gcctgtttgt ctcagtattt ctttaacaat ttcagtaagt tccttttgat   6240
ctttaattcc cttaccaaac gcagcacggg atagtatagt ggcaattagt ttaaaaacgt   6300
tttcacttaa atttactggt ctaccactac ctgaagcctt tatttcctgg actaaattcc   6360
aacattcttc ttccctcaac gattgaaatg acttaacctt ttttacagac aacaattcaa   6420
gagtacaaat cttccttaat tgtctccagt attccccata tggagcaagg acaacatcag   6480
tgttatgata taaaactatt tccccagtta aagtttcggg tctattagcg aaagtaatat   6540
cgtaggttgt aagaatttcc ttagcccact taggactcga cacgactatt gtgggtacct   6600
ctcccaattg aaggtgcatt agcgaaccat attttctcgc taaatcccct acacccctgt   6660
gtggtgtggt tccgatcaaa tggtgcatgt gaccaatgat gggtagcctc caaggttccg   6720
gcaaggactt tttagttgac ttacttctag tggcaaattt gtacacgaac aacaaaatag   6780
ttgctaaagc aattgatgta gttaaagata gtgccatagc ctttaaaatt gacttcattg   6840
ttttcctagg cctttagtga gggttgaatt cgaattttca aaaattctta ctttttttt   6900 ggatggacgc aaagaagttt aataatcata ttacatggca ttaccaccat atacatatcc   6960
atatacatat ccatatctaa tcttacttat atgttgtgga aatgtaaaga gccccattat   7020
cttagcctaa aaaaccttc tctttggaac tttcagtaat acgcttaact gctcattgct   7080
atattgaagt acggattaga agccgccgag cgggtgacag ccctccgaag gaagactctc   7140
ctccgtgcgt cctcgtcttc accggtcgcg ttcctgaaac gcagatgtgc ctcgcgccgc   7200
actgctccga acaataaaga ttctacaata ctagctttta tggttatgaa gaggaaaaat   7260
tggcagtaac ctggccccac aaaccttcaa atgaacgaat caaattaaca accataggat   7320
gataatgcga ttagtttttt agccttattt ctgggtaat taatcagcga agcgatgatt   7380
tttgatctat taacagatat ataaatgcaa aaactgcata accactttaa ctaatacttt   7440
caacattttc ggtttgtatt acttcttatt caaatgtaat aaaagtatca acaaaaaatt   7500
gttaatatac ctctatactt taacgtcaag gagaaaaaac cccaagcttc ccgggaaaac   7560
aatgcaatcg acaacttccg ttaaactatc acctttcgat cttatgactg ccttgttaaa   7620
tggtaaagtt agtttcgaca cgtccaatac ttccgataca aatataccac tggcggtttt   7680
catggaaaac agggaattgc ttatgatatt aacaaccagt gtggccgttt taattggttg   7740
tgtggttgta ttggtatgga gaagatcatc aagtgccgct aagaaggccg ccgaatcacc   7800
agtcattgtc gtcccaaaga aagtcactga agatgaggtt gatgacggca gaaagaaagt   7860
tactgtattt ttcgggacac aaacggggac tgcggaaggt tttgcgaaag ctctagttga   7920
agaagccaag gcaaggtacg aaaaagcagt attcaaagtt attgatttag atgactacgc   7980
cgcagaagat gatgaatacg aagaaaagct aaagaaagaa tctttggcat tcttcttttt   8040
agctacctat ggtgacggag aaccaacaga taacgccgct agattctata aatggtttac   8100
tgaaggagaa gaaaaggtg agtggttaga taagttacaa tacgctgtct ttggattggg   8160
aaatcgtcaa tatgaacact tcaataagat tgcaaaagtg gtcgatgaaa aattagttga   8220
```

```
gcagggggct aaaaggttag tgcctgtcgg tatgggtgat gacgatcaat gtatcgaaga    8280
tgattttact gcttggaagg aattggtttg gccagaatta gatcagctat tgagggacga    8340
agatgacaca agtgtcgcta ctccgtacac cgccgctgtt ggcgaatatc gtgttgtttt    8400
tcacgataaa cctgaaactt acgatcaaga tcaattgacc aacggacacg cagttcacga    8460
cgcccaacac ccatgcagat cgaacgttgc ggtcaagaaa gaattacaca gtcccttatc    8520
cgataggagt tgtactcatt tagaatttga tatttccaat actggactat cgtatgaaac    8580
tggcgaccat gtcggtgtat atgtggaaaa cctgtctgaa gttgtagatg aagccgaaaa    8640
attgattggg cttcctccac atacatactt ttctgtgcat acagataatg aagatggtac    8700
tccacttggc ggagcctcgt taccacctcc ctttccacca tgtacactta gaaaagctct    8760
tgcatcttat gcagatgtac tttcttcacc aaagaaaagt gcattactag ctctagccgc    8820
ccatgctacc gactctactg aagctgaccg tttgaaattc tttgcttcac ctgctggcaa    8880
agacgagtac gcacagtgga ttgtggcatc tcacagatca ttgctggaag tgatggaagc    8940
cttcccatcg gcaaagccac cattaggcgt gttttcgca tctgttgccc cacgtttaca    9000
gcctagatac tattccatat cttctagccc aaaatttgcc cccaatcgta ttcatgtgac    9060
gtgtgcgctg gtgtatgaac aaactccatc aggaagggta cataaaggtg tctgtagtac    9120
atggatgaaa aacgcggtgc caatgactga atctcaagat tgttcgtggg caccaattta    9180
tgttcgtact tctaattta gactacctag tgaccctaaa gtaccagtga ttatgatcgg    9240
gcctgggaca ggactagcgc cattcagagg tttcttacaa gaaagattgg cccaaaagga    9300
agcaggtacg gaattaggaa ccgcaattct attctttggt tgtcgtaata gaaaagttga    9360
ctttatatac gaagatgagt taaacaactt cgttgaaact ggagcgttat cagaattagt    9420
gacagcattc tctagggaag gtgcaacaaa agaatacgtc caacataaaa tgacccaaaa    9480
ggccagcgat atatggaatt tgctgtccga gggtgcctat ttgtacgttt gtggtgatgc    9540
aaagggaatg gctaaagatg ttcacaggac attgcataca attgttcagg aacaaggttc    9600
cttggattcc tctaaggcag aactttatgt taaaaacctt cagatggctg gtagatattt    9660
gcgtgatgtt tggtgagcta gctaagatcc gctctaaccg aaaaggaagg agttagacaa    9720
cctgaagtct aggtccctat ttattttttt atagttatgt tagtattaag aacgttattt    9780
atatttcaaa ttttttcttt ttttctgtac agacgcgtgt acgcatgtaa cattatactg    9840
aaaaccttgc ttgagaaggt tttgggacgc tcgaagatcc agctgcatta atgaatcggc    9900
caacgcgcgg ggagaggcgg tttgcgtatt gggcgctctt ccgcttcctc gctcactgac    9960
tcgctgcgct cggtcgttcg gctgcggcga gcggtatcag ctcactcaaa ggcggtaata   10020
cggttatcca cagaatcagg ggataacgca ggaaagaaca tgtgagcaaa aggccagcaa   10080
aaggccagga accgtaaaaa ggccgcgttg ctggcgtttt tccataggct ccgcccccct   10140
gacgagcatc acaaaaatcg acgctcaagt cagaggtggc gaaacccgac aggactataa   10200
agataccagg cgtttccccc tggaagctcc ctcgtgcgct ctcctgttcc gaccctgccg   10260
cttaccggat acctgtccgc ctttctccct tcgggaagcg tggcgctttc tcatagctca   10320
cgctgtaggt atctcagttc ggtgtaggtc gttcgctcca agctgggctg tgtgcacgaa   10380
ccccccgttc agcccgaccg ctgcgcctta tccggtaact atcgtcttga gtccaacccg   10440
gtaagacacg acttatcgcc actggcagca gccactggta acaggattag cagagcgagg   10500
tatgtaggcg gtgctacaga gttccttgaa gtggtggccta actacggcta cactagaagg   10560
acagtatttg gtatctgcgc tctgctgaag ccagttacct tcggaaaaag agttggtagc   10620
```

```
tcttgatccg gcaaacaaac caccgctggt agcggtggtt tttttgtttg caagcagcag   10680
attacgcgca gaaaaaaagg atctcaagaa gatcctttga tcttttctac ggggtctgac   10740
gctcagtgga acgaaaactc acgttaaggg attttggtca tgagattatc aaaaaggatc   10800
ttcacctaga tccttttaaa ttaaaaatga agttttaaat caatctaaag tatatatgag   10860
taaacttggt ctgacagtta ccaatgctta atcagtgagg cacctatctc agcgatctgt   10920
ctatttcgtt catccatagt tgcctgactc cccgtcgtgt agataactac gatacgggag   10980
ggcttaccat ctggccccag tgctgcaatg ataccgcgag acccacgctc accggctcca   11040
gatttatcag caataaacca gccagccgga agggccgagc gcagaagtgg tcctgcaact   11100
ttatccgcct ccatccagtc tattaattgt tgccgggaag ctagagtaag tagttcgcca   11160
gttaatagtt tgcgcaacgt tgttgccatt gctacaggca tcgtggtgtc acgctcgtcg   11220
tttggtatgg cttcattcag ctccggttcc caacgatcaa ggcgagttac atgatccccc   11280
atgttgtgca aaaaagcggt tagctccttc ggtcctccga tcgttgtcag aagtaagttg   11340
gccgcagtgt tatcactcat ggttatggca gcactgcata attctcttac tgtcatgcca   11400
tccgtaagat gcttttctgt gactggtgag tactcaacca agtcattctg agaatagtgt   11460
atgcggcgac cgagttgctc ttgcccggcg tcaatacggg ataataccgc gccacatagc   11520
agaactttaa aagtgctcat cattggaaaa cgttcttcgg ggcgaaaact ctcaaggatc   11580
ttaccgctgt tgagatccag ttcgatgtaa cccactcgtg cacccaactg atcttcagca   11640
tcttttactt tcaccagcgt ttctgggtga gcaaaaacag gaaggcaaaa tgccgcaaaa   11700
aagggaataa gggcgacacg gaaatgttga atactcatac tcttcctttt tcaatattat   11760
tgaagcattt atcagggtta ttgtctcatg agcggataca tatttgaatg tatttagaaa   11820
aataaacaaa taggggttcc gcgcacattt ccccgaaaag tgccacctga acgaagcatc   11880
tgtgcttcat tttgtagaac aaaaatgcaa cgcgagagcg ctaattttcc aaacaaagaa   11940
tctgagctgc atttttacag aacagaaatg caacgcgaaa gcgctatttt accaacgaag   12000
aatctgtgct tcatttttgt aaaacaaaaa tgcaacgcga gagcgctaat ttttcaaaca   12060
aagaatctga gctgcatttt tacagaacag aaatgcaacg cgagagcgct attttaccaa   12120
caaagaatct atacttcttt tttgttctac aaaaatgcat cccgagagcg ctatttttct   12180
aacaaagcat cttagattac tttttttctc ctttgtgcgc tctataatgc agtctcttga   12240
taactttttg cactgtaggt ccgttaaggt tagaagaagg ctacttggt gtctatttc   12300 tcttccataa aaaaagcctg actccacttc ccgcgtttac tgattactag cgaagctgcg   12360
ggtgcatttt ttcaagataa aggcatcccc gattatattc tataccgatg tggattgcgc   12420
atactttgtg aacagaaagt gatagcgttg atgattcttc attggtcaga aaattatgaa   12480
cggtttcttc tattttgtct ctatatacta cgtataggaa atgtttacat ttcgtattg   12540 ttttcgattc actctatgaa tagttcttac tacaattttt ttgtctaaag agtaaactaa   12600
gagataaaca taaaaatgt agaggtcgag tttagatgca agttcaagga gcgaaaggtg   12660
gatgggtagg ttatataggg atatagcaca gagatatata gcaaagagat acttttgagc   12720
aatgtttgtg gaagcggtat tcgcaatatt ttagtagctc gttacagtcc ggtgcgtttt   12780
tggttttttg aaagtgcgtc ttcagagcgc ttttggtttt caaaagcgct ctgaagttcc   12840
tatactttct agagaatagg aacttcggaa taggaacttc aaagcgtttc cgaaaacgag   12900
cgcttccgaa aatgcaacgc gagctgcgca catacagctc actgttcacg tcgcacctat   12960
```

-continued

```
atctgcgtgt tgcctgtata tatatataca tgagaagaac ggcatagtgc gtgtttatgc    13020
ttaaatgcgt acttatatgc gtctatttat gtaggatgaa aggtagtcta gtacctcctg    13080
tgatattatc ccattccatg cggggtatcg tatgcttcct tcagcactac cctttagctg    13140
ttctatatgc tgccactcct caattggatt agtctcatcc ttcaatgcta tcatttcctt    13200
tgatattgga tcatactaag aaaccattat tatcatgaca ttaacctata aaaataggcg    13260
tatcacgagg ccctttcgtc                                                 13280
```

PRODUCTION OF ISOPRENOIDS

CROSS-REFERENCE

This application claims priority to U.S. Provisional Application Nos. 60/808,989, filed May 26, 2006 and 60/870,592 filed on Dec. 18, 2006, which are incorporated herein by reference in their entirety.

BACKGROUND OF THE INVENTION

Isoprenoids are ubiquitous in nature. They comprise a diverse family of over 40,000 individual products, many of which are vital to living organisms. Isoprenoids serve to maintain cellular fluidity, electron transport, and other metabolic functions. A vast number of natural and synthetic isoprenoids are useful as pharmaceuticals, cosmetics, perfumes, pigments and colorants, fungicides, antiseptics, nutraceuticals, and fine chemical intermediates.

An isoprenoid product is typically composed of repeating five carbon isopentenyl diphosphate (IPP) units, although irregular isoprenoids and polyterpenes have been reported. In nature, isoprenoids are synthesized by consecutive condensations of their precursor IPP and its isomer dimethylallyl pyrophosphate (DMAPP). Two pathways for these precursors are known. Eukaryotes, with the exception of plants, generally use the mevalonate-dependent (MEV) pathway to convert acetyl coenzyme A (acetyl-CoA) to IPP, which is subsequently isomerized to DMAPP. Prokaryotes, with some exceptions, typically employ only the mevalonate-independent or deoxyxylulose-5-phosphate (DXP) pathway to produce IPP and DMAPP. Plants use both the MEV pathway and the DXP pathway. See Rohmer et al. (1993) *Biochem. J.* 295:517-524; Lange et al. (2000) *Proc. Natl. Acad. Sci. USA* 97(24):13172-13177; Rohdich et al. (2002) *Proc. Natl. Acad. Sci. USA* 99:1158-1163.

Traditionally, isoprenoids have been manufactured by extraction from natural sources such as plants, microbes, and animals. However, the yield by way of extraction is usually very low due to a number of profound limitations. First, most isoprenoids accumulate in nature in only small amounts. Second, the source organisms in general are not amenable to the large-scale cultivation that is necessary to produce commercially viable quantities of a desired isoprenoid. Third, the requirement of certain toxic solvents for isoprenoid extraction necessitates special handling and disposal procedures, and thus complicating the commercial production of isoprenoids.

The elucidation of the MEV and DXP metabolic pathways has made biosynthetic production of isoprenoids feasible. For instance, microbes have been engineered to overexpress a part of or the entire mevalonate pathway for production of an isoprenoid named amorpha-4,11-diene (U.S. Pat. Nos. 7,172,886 and 7,192,751) Other efforts have focused on balancing the pool of glyceraldehyde-3-phosphate and pyruvate, or on increasing the expression of 1-deoxy-D-xylulose-5-phosphate synthase (dxs) and IPP isomerase (idi). See Farmer et al. (2001) *Biotechnol. Prog.* 17:57-61; Kajiwara et al. (1997) *Biochem. J.* 324:421-426; and Kim et al. (2001) *Biotechnol. Bioeng.* 72:408-415.

Nevertheless, given the very large quantities of isoprenoid products needed for many commercial applications, there remains a need for expression systems and fermentation procedures that produce even more isoprenoids than available with current technologies. Optimal redirection of microbial metabolism toward isoprenoid production requires that the introduced biosynthetic pathway is properly engineered both to funnel carbon to isoprenoid production efficiently and to prevent build up of toxic levels of metabolic intermediates over a sustained period of time. The present invention addresses this need and provides related advantages as well.

SUMMARY OF THE INVENTION

The present invention provides compositions and methods for a robust production of isoprenoids by the use of isopentenyl pyrophosphate pathway enzymes that are under the control of at least one heterologous regulator or fermentation conditions, either alone or in combination. Non-limiting examples of suitable isoprenoids include: hemiterpenes (derived from 1 isoprene unit) such as isoprene; monoterpenes (derived from 2 isoprene units) such as myrcene; sesquiterpenes (derived from 3 isoprene units) such as amorpha-4,11-diene; diterpenes (derived from four isoprene units) such as taxadiene; triterpenes (derived from 6 isoprene units) such as squalene; tetraterpenes (derived from 8 isoprenoids) such as β-carotene; and polyterpenes (derived from more than 8 isoprene units) such as polyisoprene.

In one aspect, a method of producing an isoprenoid involves the steps of (a) obtaining a plurality of host cells that comprise an enzymatic pathway for making isopentenyl pyrophosphate wherein the all of the pathway enzymes are under control of at least one heterologous transcriptional regulator; and (b) culturing the host cells in a medium under conditions that are suboptimal as compared to conditions that would provide for a maximum specific growth rate for the host cells. In some embodiments, the pathway is the mevalonate pathway. In other embodiments, the pathway is the DXP pathway. In other embodiments, the at least one heterologous transcriptional regulatory sequence is inducible. In other embodiments, the pathway enzymes are under control of a single transcriptional regulator. In other embodiments, the pathway enzymes are under control of multiple heterologous transcriptional regulators.

In some embodiments, the pathway comprises a nucleic acid sequence encoding a mevalonate pathway enzyme from a prokaryote having an endogenous mevalonate pathway. Exemplary prokaryotes having an endogenous mevalonate pathway include but are not limited to the genus *Enterococcus*, the genus *Pseudomonas*, and the genus *Staphylococcus*. In one embodiment, the mevalonate pathway enzyme is selected from acetyl-CoA thiolase, HMG-CoA synthase, HMG-CoA reductase, and mevalonate kinase. In another embodiment, the heterologous nucleic acid sequence encodes a Class II HMG-CoA reductase.

In another embodiment, the host cells are cultured in a medium wherein the nutrient and/or temperature level is maintained at a level below that which would provide for the maximum specific growth rate for the host cells. In another embodiment, the host cells are cultured in a medium where the carbon source is maintained at a level to provide for less than about 90%, 75%, 50%, 25%, 10%, or anywhere between 90% and 10% of the maximum specific growth rate. In another embodiment, the host cells are cultured in a medium where the nitrogen source is maintained at a level to provide for less than about 90%, 75%, 50%, 25%, 10%, or anywhere between 90% and 10% of the maximum specific growth rate. In another embodiment, the host cells are cultured in a medium where the temperature is maintained at a level to provide for less than about 90%, 75%, 50%, 25%, 10% or anywhere between 90% and 10% of the maximum specific growth rate. In another embodiment, the medium temperature is maintained at least about 2° C., 4° C., 5° C., 6° C., 8° C., 10°

C., 15° C., or 20° C. below the temperature that would provide for the maximum specific growth rate.

In yet another embodiment, a method of producing an isoprenoid or isoprenoid precursor comprises the steps of (i) performing a fermentation reaction comprising a fermentation medium and a plurality of genetically modified host cells that produce the isoprenoid under conditions such that (a) the fermentation medium is kept at a temperature lower than that which would provide for a maximum specific growth rate of said host cells; (b) the fermentation medium comprises a carbon source present in an amount that is lower than that which would provide for a maximum specific growth rate of the host cells; and/or (c) the fermentation medium comprises a nitrogen source present in an amount that is lower than that which would provide for a maximum specific growth rate of the host cells; (ii) recovering the isoprenoid produced under one or more conditions set forth in (a) through (c). In one aspect, the isoprenoid is produced under at least two of the conditions set forth in (a) through (c). In another aspect, the isoprenoid is produced under all of the conditions set forth in (a) through (c).

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIGS. 10A-B show the increased volumetric and specific amorpha-4,11-diene productivity of host strains carrying the *Staphylococcus aureus* HMGR and HMGS genes compared to host strains carrying the *Saccharomyces cerevisiae* tHMGR and HMGS genes.

FIG. 11A-B show the effect of lower temperature on amorpha-4,11-diene productivity of an *Escherichia coli* host strain.

FIGS. 12A-D show the effect of reduced glucose levels on amorpha-4,11-diene productivity of an *Escherichia coli* host strain.

FIGS. 13A-B show the combined effects of lower temperature and reduced glucose levels on amorpha-4,11-diene productivity of an *Escherichia coli* host strain.

FIGS. 14A-E and 15A-E show the combined effects of lower temperature and reduced glucose and nitrogen levels on amorpha-4,11-diene productivity of an *Escherichia coli* host strain.

DETAILED DESCRIPTION OF THE INVENTION

Definitions

Figure 1A:
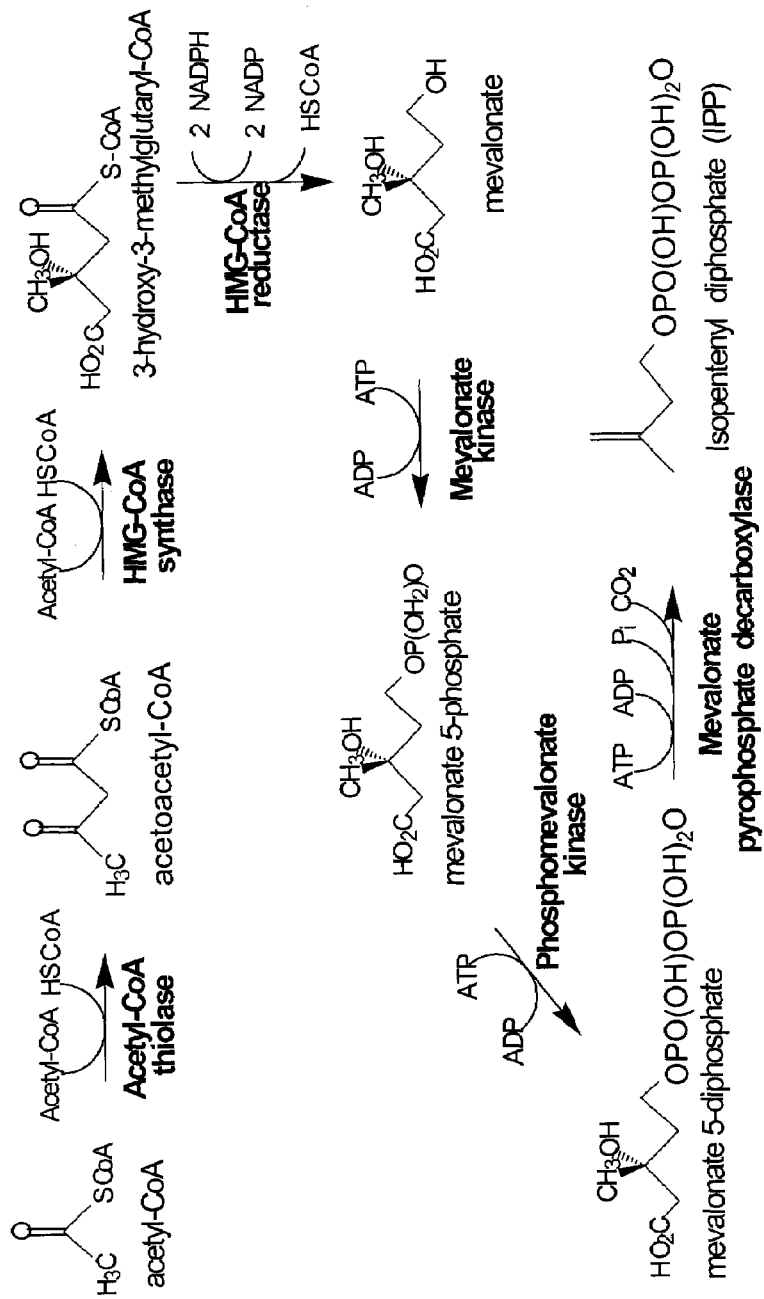
FIG. 1A is a schematic representation of the mevalonate ("MEV") pathway for the production of isopentenyl pyrophosphate ("IPP").

Unless defined otherwise, all technical and scientific terms used herein have the same meaning as commonly understood by one of ordinary skill in the art to which this invention belongs. Reference is made here to a number of terms that shall be defined to have the following meanings:

The term "optional" or "optionally" means that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where the event or circumstance does not occur.

The terms "metabolic pathway" is used herein to refer to a catabolic pathway or an anabolic pathway. Anabolic pathways involve constructing a larger molecule from smaller molecules, a process requiring energy. Catabolic pathways involve breaking down of larger molecules, often releasing energy.

The term "mevalonate pathway" or "MEV pathway" is used herein to refer to the biosynthetic pathway that converts acetyl-CoA to IPP. The MEV pathway is illustrated schematically in FIG. 1A.

The term "deoxyxylulose 5-phosphate pathway" or "DXP pathway" is used herein to refer to the pathway that converts glyceraldehyde-3-phosphate and pyruvate to IPP and DMAPP. The DXP pathway is illustrated schematically in FIG. 1B.

The word "pyrophosphate" is used interchangeably herein with "diphosphate".

The terms "expression vector" or "vector" refer to a nucleic acid that transduces, transforms, or infects a host cell, thereby causing the cell to produce nucleic acids and/or proteins other than those that are native to the cell, or to express nucleic acids and/or proteins in a manner that is not native to the cell.

The term "endogenous" refers to a substance or process that occurs naturally, e.g., in a non-recombinant host cell.

The terms "enzymatic pathway for making isopentenyl pyrophosphate" refers to any pathway capable of producing isopentyl pyrophosphate, including, without limitation, either the mevalonate pathway or the DXP pathway.

The term "nucleic acid" refers to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically, or biochemically modified, non-natural, or derivatized nucleotide bases.

The term "operon" is used to refer to two or more contiguous nucleotide sequences that each encode a gene product such as a RNA or a protein, and the expression of which are coordinately regulated by one or more controlling elements (for example, a promoter).

The term "gene product" refers to RNA encoded by DNA (or vice versa) or protein that is encoded by an RNA or DNA, where a gene will typically comprise one or more nucleotide sequences that encode a protein, and may also include introns and other non-coding nucleotide sequences.

The term "protein" refers to a polymeric form of amino acids of any length, which can include coded and non-coded amino acids, chemically or biochemically modified or derivatized amino acids, and polypeptides having modified peptide backbones.

The term "heterologous nucleic acid" as used herein refers to a nucleic acid wherein at least one of the following is true: (a) the nucleic acid is foreign ("exogenous") to (that is, not naturally found in) a given host cell; (b) the nucleic acid comprises a nucleotide sequence that is naturally found in (that is, is "endogenous to") a given host cell, but the nucleotide sequence is produced in an unnatural (for example, greater than expected or greater than naturally found) amount in the cell; (c) the nucleic acid comprises a nucleotide sequence that differs in sequence from an endogenous nucleotide sequence, but the nucleotide sequence encodes the same protein (having the same or substantially the same amino acid sequence) and is produced in an unnatural (for example, greater than expected or greater than naturally found) amount in the cell; or (d) the nucleic acid comprises two or more nucleotide sequences that are not found in the same relationship to each other in nature (for example, the nucleic acid is recombinant).

A "transgene" refers to a gene that is exogenously introduced into a host cell. It can comprise an endogenous or exogenous, or heterologous nucleic acid.

The term "recombinant host" (also referred to as a "genetically modified host cell" or "genetically modified host microorganism") denotes a host cell that comprises a heterologous nucleic acid of the invention.

The term "exogenous nucleic acid" refers to a nucleic acid that is exogenously introduced into a host cell, and hence is not normally or naturally found in and/or produced by a given cell in nature.

The term "regulatory element" refers to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" refers to a permanent or transient genetic change induced in a cell following introduction of new nucleic acid. Genetic change ("modification") can be accomplished either by incorporation of the new DNA into the genome of the host cell, or by transient or stable maintenance of the new DNA as an episomal element. In eukaryotic cells, a permanent genetic change is generally achieved by introduction of the DNA into the genome of the cell. In prokaryotic cells, a permanent genetic change can be introduced into the chromosome or via extrachromosomal elements such as plasmids and expression vectors, which may contain one or more selectable markers to aid in their maintenance in the recombinant host cell.

The term "operably linked" refers to a juxtaposition wherein the components so described are in a relationship permitting them to function in their intended manner. For instance, a promoter is operably linked to a nucleotide sequence if the promoter affects the transcription or expression of the nucleotide sequence.

The term "host cell" and "host microorganism" are used interchangeably herein to refer to any archae, bacterial, or eukaryotic living cell into which a heterologous nucleic acid can be or has been inserted. The term also relates to the progeny of the original cell, which may not necessarily be completely identical in morphology or in genomic or total DNA complement to the original parent, due to natural, accidental, or deliberate mutation.

The term "synthetic" as used in reference to nucleic acids means the annealing of chemically synthesized oligonucleotide building blocks to form gene segments, which are then enzymatically assembled to construct the entire gene. Synthesis of nucleic acids via "chemical means" means that the component nucleotides were assembled in vitro.

The term "natural" as applied to a nucleic acid, a cell, or an organism, refers to a nucleic acid, cell, or organism that is found in nature. For example, a polypeptide or polynucleotide sequence that is present in a non-pathological (un-diseased) organism that can be isolated from a source in nature and that has not been intentionally modified by a human in the laboratory is natural.

The term "naturally occurring" as applied to a nucleic acid, an enzyme, a cell, or an organism, refers to a nucleic acid, enzyme, cell, or organism that is found in nature. For example, a polypeptide or polynucleotide sequence that is present in an organism that can be isolated from a source in nature and that has not been intentionally modified by a human in the laboratory is naturally occurring.

The term "biologically active fragment" as applied to a protein, polypeptide or enzyme refers to functional portion(s) of the proteins or polypeptide or enzyme. Functionally equivalents may have variant amino acid sequences may arise, e.g., as a consequence of codon redundancy and functional equivalency which are known to occur naturally within nucleic acid sequences and the proteins thus encoded. Functionally equivalent proteins or peptides may alternatively be constructed via the application of recombinant DNA technology, in which changes in the protein structure may be engineered, based on considerations of the properties of the amino acids being exchanged.

The terms "isoprenoid", "isoprenoid compound", "isoprenoid product", "terpene", "terpene compound", "terpenoid", and "terpenoid compound" are used interchangeably herein. They refer to compounds that are capable of being derived from IPP.

The singular forms "a," "and," and "the" include plural referents unless the context clearly dictates otherwise. Thus, for example, reference to "an expression vector" includes a single expression vector as well as a plurality of expression vectors, and reference to "the host cell" includes reference to one or more host cells, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Unless otherwise indicated, this invention is not limited to particular sequences, expression vectors, enzymes, host microorganisms, or processes, as such may vary in accordance with the understanding of those of ordinary skill in the arts to which this invention pertains in view of the teaching herein. Terminology used herein is for purposes of describing particular embodiments only and is not intended to be limiting.

Host Cells

Any suitable host cell may be used in the practice of the present invention. In one embodiment, the host cell is a genetically modified host microorganism in which nucleic acid molecules have been inserted, deleted or modified (i.e., mutated; e.g., by insertion, deletion, substitution, and/or inversion of nucleotides), to either produce the desired isoprenoid compound or isoprenoid derivative, or effect an increased yield of the desired isoprenoid compound or isoprenoid derivative. In another embodiment, the host cell is capable of being grown in liquid growth medium. In contrast, a "control cell" is an alternative subject or sample used in an experiment for comparison purpose, and is typically a parental cell that does not contain the modification(s) made to a corresponding host cell.

Illustrative examples of suitable host cells include any archae, prokaryotic, or eukaryotic cell. Examples of an archae cell include, but are not limited to those belonging to the genera: *Aeropyrum, Archaeglobus, Halobacterium, Methanococcus, Methanobacterium, Pyrococcus, Sulfolobus*, and *Thermoplasma*. Illustrative examples of archae strains include but are not limited to: *Aeropyrum pernix, Archaeoglobus fulgidus, Methanococcus jannaschii, Methanobacterium thermoautotrophicum, Pyrococcus abyssi, Pyrococcus horikoshii, Thermoplasma acidophilum, Thermoplasma volcanium*.

Examples of a procaryotic cell include, but are not limited to those belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus*, and *Zymomonas*.

Illustrative examples of prokaryotic bacterial strains include but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei, Staphylococcus aureus*, and the like.

In general, if a bacterial host cell is used, a non-pathogenic strain is preferred. Illustrative examples of non-pathogenic strains include but are not limited to: *Bacillus subtilis, Escherichia coli, Lactibacillus acidophilus, Lactobacillus helveticus, Pseudomonas aeruginosa, Pseudomonas mevalonii, Pseudomonas pudita, Rhodobacter sphaeroides, Rodobacter capsulatus, Rhodospirillum rubrum*, and the like.

Examples of eukaryotic cells include but are not limited to fungal cells. Examples of fungal cell include, but are not limited to those belonging to the genera: *Aspergillus, Candida, Chrysosporium, Cryotococcus, Fusarium, Kluyveromyces, Neotyphodium, Neurospora, Penicillium, Pichia, Saccharomyces, Trichoderma* and *Xanthophyllomyces* (formerly *Phaffia*).

Illustrative examples of eukaryotic strains include but are not limited to: *Aspergillus nidulans, Aspergillus niger, Aspergillus oryzae, Candida albicans, Chrysosporium lucknowense, Fusarium graminearum, Fusarium venenatum, Kluyveromyces lactis, Neurospora crassa, Pichia angusta, Pichia finlandica, Pichia kodamae, Pichia membranaefaciens, Pichia methanolica, Pichia opuntiae, Pichia pastoris, Pichia pijperi, Pichia quercuum, Pichia salictaria, Pichia thermotolerans, Pichia trehalophila, Pichia stipitis, Streptomyces ambofaciens, Streptomyces aureofaciens, Streptomyces aureus, Saccaromyces bayanus, Saccaromyces boulardi, Saccharomyces cerevisiae, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus, Trichoderma reesei* and *Xanthophyllomyces dendrorhous* (formerly *Phaffia rhodozyma*).

In general, if a eukaryotic cell is used, a non-pathogenic strain is preferred. Illustrative examples of non-pathogenic strains include but are not limited to: *Fusarium graminearum, Fusarium venenatum, Pichia pastoris, Saccaromyces boulardi*, and *Saccaromyces cerevisiae*.

In addition, certain strains have been designated by the Food and Drug Administration as GRAS or Generally Regarded As Safe. These strains include: *Bacillus subtilis, Lactibacillus acidophilus, Lactobacillus helveticus*, and *Saccharomyces cerevisiae*.

IPP Pathways

The host cells of the present invention comprise or utilize the MEV pathway, the DXP pathway or both to synthesize IPP and its isomer, DMAPP. In general, eukaryotes other than plants use the MEV isoprenoid pathway exclusively to convert acetyl-CoA to IPP, which is subsequently isomerized to DMAPP. Prokaryotes, with some exceptions, use the mevalonate-independent or DXP pathway to produce IPP and DMAPP separately through a branch point. In general, plants use both the MEV and DXP pathways for IPP synthesis.

MEV Pathway

A schematic representation of the MEV pathway is described in FIG. 1A. In general, the pathway comprises six steps.

In the first step, two molecules of acetyl-coenzyme A are enzymatically combined to form acetoacetyl-CoA. An enzyme known to catalyze this step is, for example, acetyl-CoA thiolase (also known as acetyl-CoA acetyltransferase). Illustrative examples of nucleotide sequences include but are not limited to the following GenBank accession numbers and the organism from which the sequences derived: (NC_000913 REGION: 2324131 . . . 2325315; *Escherichia coli*), (D49362; *Paracoccus denitrificans*), and (L20428; *Saccharomyces cerevisiae*).

In the second step of the MEV pathway, acetoacetyl-CoA is enzymatically condensed with another molecule of acetyl-CoA to form 3-hydroxy-3-methylglutaryl-CoA (HMG-CoA). An enzyme known to catalyze this step is, for example, HMG-CoA synthase. Illustrative examples of nucleotide sequences include but are not limited to: (NC_001145. complement 19061 . . . 20536; *Saccharomyces cerevisiae*), (X96617; *Saccharomyces cerevisiae*), (X83882; *Arabidopsis*

*thaliana*), (AB037907; *Kitasatospora griseola*), (BT007302; *Homo sapiens*), and (NC_002758, Locus tag SAV2546, GeneID 1122571; *Staphylococcus aureus*).

In the third step, HMG-CoA is enzymatically converted to mevalonate. An enzyme known to catalyze this step is, for example, HMG-CoA reductase. Illustrative examples of nucleotide sequences include but are not limited to: (NM 206548; *Drosophila melanogaster*), (NC_002758, Locus tag SAV2545, GeneID 1122570; *Staphylococcus aureus*), (NM_204485; *Gallus gallus*), (AB015627; *Streptomyces* sp. KO 3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734 . . . 118898; *Saccharomyces cerevisiae*).

In the fourth step, mevalonate is enzymatically phosphorylated to form mevalonate 5-phosphate. An enzyme known to catalyze this step is, for example, mevalonate kinase. Illustrative examples of nucleotide sequences include but are not limited to: (L77688; *Arabidopsis thaliana*), and (X55875; *Saccharomyces cerevisiae*).

In the fifth step, a second phosphate group is enzymatically added to mevalonate 5-phosphate to form mevalonate 5-pyrophosphate. An enzyme known to catalyze this step is, for example, phosphomevalonate kinase. Illustrative examples of nucleotide sequences include but are not limited to: (AF429385; *Hevea brasiliensis*), (NM_006556; *Homo sapiens*), and (NC_001145. complement 712315 . . . 713670; *Saccharomyces cerevisiae*).

In the sixth step, mevalonate 5-pyrophosphate is enzymatically converted into IPP. An enzyme known to catalyze this step is, for example, mevalonate pyrophosphate decarboxylase. Illustrative examples of nucleotide sequences include but are not limited to: (X97557; *Saccharomyces cerevisiae*), (AF290095; *Enterococcus faecium*), and (U49260; *Homo sapiens*).

If IPP is to be converted to DMAPP, then a seventh step is required. An enzyme known to catalyze this step is, for example, IPP isomerase. Illustrative examples of nucleotide sequences include but are not limited to: (NC_000913, 3031087 . . . 3031635; *Escherichia coli*), and (AF082326; *Haematococcus pluvialis*). If the conversion to DMAPP is required, an increased expression of IPP isomerase ensures that the conversion of IPP into DMAPP does not represent a rate-limiting step in the overall pathway.

DXP Pathway

Figure 1B:
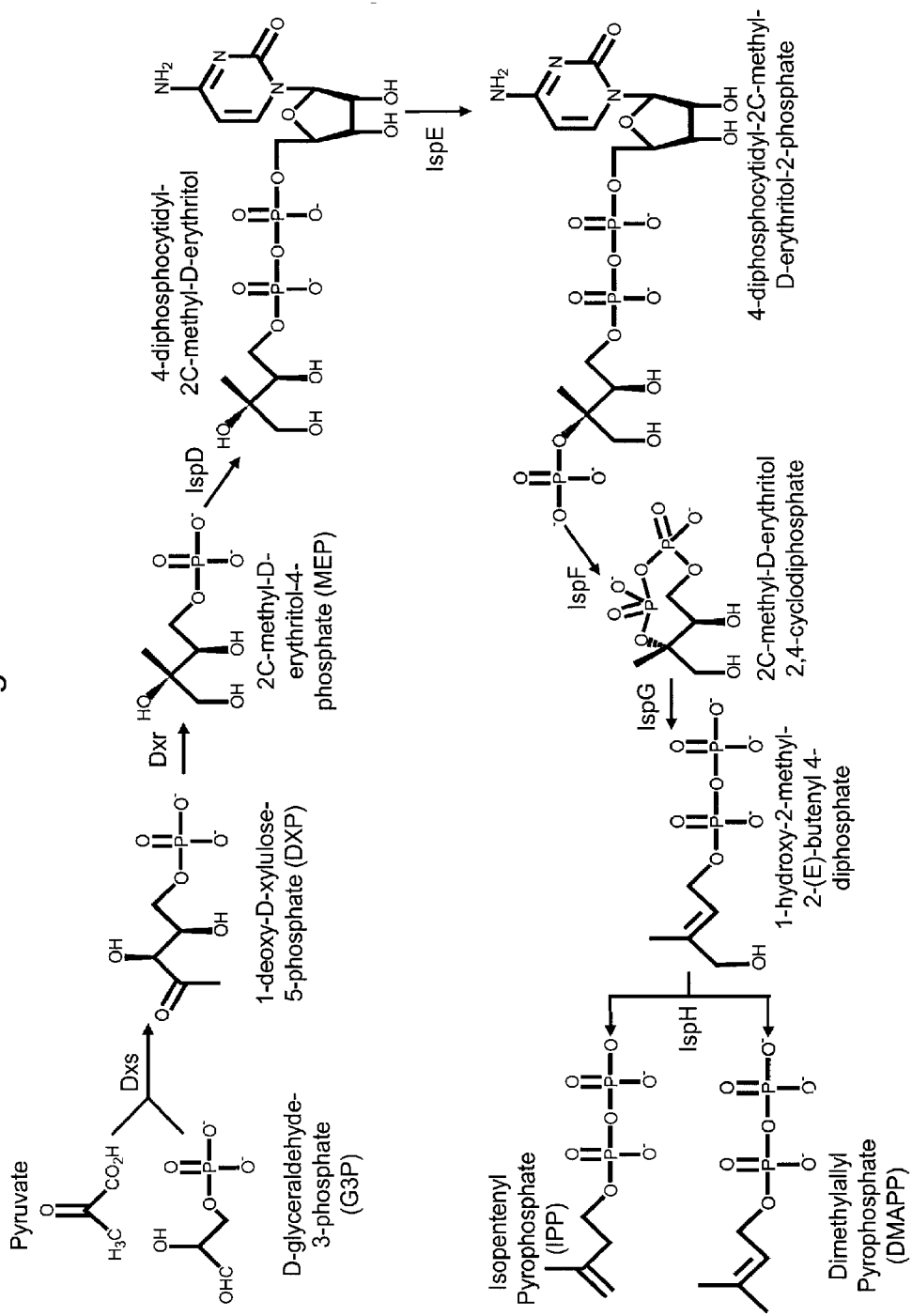
FIG. 1B is a schematic representation of the 1-deoxy-D-xylulose 5-diphosphate ("DXP") pathway for the production of isopentenyl pyrophosphate ("IPP") and dimethylallyl pyrophosphate ("DMAPP"). Dxs is 1-deoxy-D-xylulose-5-phosphate synthase; Dxr is 1-deoxy-D-xylulose-5-phosphate reductoisomerase (also known as IspC); IspD is 4-diphosphocytidyl-2C-methyl-D-erythritol synthase; IspE is 4-diphosphocytidyl-2C-methyl-D-erythritol synthase; IspF is 2C-methyl-D-erythritol 2,4-cyclodiphosphate synthase; IspG is 1-hydroxy-2-methyl-2-(E)-butenyl 4-diphosphate synthase (IspG); and ispH is isopentenyl/dimethylallyl diphosphate synthase.

A schematic representation of the DXP pathway is described in FIG. 1B. In general, the DXP pathway comprises seven steps. In the first step, pyruvate is condensed with D-glyceraldehyde 3-phosphate to make 1-deoxy-D-xylulose-5-phosphate. An enzyme known to catalyze this step is, for example, 1-deoxy-D-xylulose-5-phosphate synthase. Illustrative examples of nucleotide sequences include but are not limited to: (AF035440; *Escherichia coli*), (NC_002947, locus tag PP0527; *Pseudomonas putida* KT2440), (CP000026, locus tag SPA2301; *Salmonella enterica Paratyphi*, see ATCC 9150), (NC_007493, locus tag RSP_0254; *Rhodobacter sphaeroides* 2.4.1), (NC_005296, locus tag RPA0952; *Rhodopseudomonas palustris* CGA009), (NC_004556, locus tag PD1293; *Xylella fastidiosa Temecula*1), and (NC_003076, locus tag AT5G11380; *Arabidopsis thaliana*).

In the second step, 1-deoxy-D-xylulose-5-phosphate is converted to 2C-methyl-D-erythritol-4-phosphate. An enzyme known to catalyze this step is, for example, 1-deoxy-D-xylulose-5-phosphate reductoisomerase. Illustrative examples of nucleotide sequences include but are not limited to: (AB013300; *Escherichia coli*), (AF148852; *Arabidopsis thaliana*), (NC_002947, locus tag PP1597; *Pseudomonas putida* KT2440), (AL939124, locus tag SCO5694; *Streptomyces coelicolor* A3(2)), (NC_007493, locus tag RSP_2709; *Rhodobacter sphaeroides* 2.4.1), and (NC_007492, locus tag Pfl_1107; *Pseudomonas fluorescens* PfO-1).

In the third step, 2C-methyl-D-erythritol-4-phosphate is converted to 4-diphosphocytidyl-2C-methyl-D-erythritol. An enzyme known to catalyze this step is, for example, 4-diphosphocytidyl-2C-methyl-D-erythritol synthase. Illustrative examples of nucleotide sequences include but are not limited to: (AF230736; *Escherichia coli*), (NC_007493, locus_tag RSP_2835; *Rhodobacter sphaeroides* 2.4.1), (NC_003071, locus_tag AT2G02500; *Arabidopsis thaliana*), and (NC_002947, locus_tag PP1614; *Pseudomonas putida* KT2440).

In the fourth step, 4-diphosphocytidyl-2C-methyl-D-erythritol is converted to 4-diphosphocytidyl-2C-methyl-D-erythritol-2-phosphate. An enzyme known to catalyze this step is, for example, 4-diphosphocytidyl-2C-methyl-D-erythritol kinase. Illustrative examples of nucleotide sequences include but are not limited to: (AF216300; *Escherichia coli*) and (NC_007493, locus_tag RSP_1779; *Rhodobacter sphaeroides* 2.4.1).

In the fifth step, 4-diphosphocytidyl-2C-methyl-D-erythritol-2-phosphate is converted to 2C-methyl-D-erythritol 2,4-cyclodiphosphate. An enzyme known to catalyze this step is, for example, 2C-methyl-D-erythritol 2,4-cyclodiphosphate synthase. Illustrative examples of nucleotide sequences include but are not limited to: (AF230738; *Escherichia coli*), (NC_007493, locus_tag RSP_6071; *Rhodobacter sphaeroides* 2.4.1), and (NC_002947, locus_tag PP1618; *Pseudomonas putida* KT2440).

In the sixth step, 2C-methyl-D-erythritol 2,4-cyclodiphosphate is converted to 1-hydroxy-2-methyl-2-(E)-butenyl-4-diphosphate. An enzyme known to catalyze this step is, for example, 1-hydroxy-2-methyl-2-(E)-butenyl-4-diphosphate synthase. Illustrative examples of nucleotide sequences include but are not limited to: (AY033515; *Escherichia coli*), (NC_002947, locus_tag PP0853; *Pseudomonas putida* KT2440), and (NC_007493, locus_tag RSP_2982; *Rhodobacter sphaeroides* 2.4.1).

In the seventh step, 1-hydroxy-2-methyl-2-(E)-butenyl-4-diphosphate is converted into either IPP or its isomer, DMAPP. An enzyme known to catalyze this step is, for example, isopentyl/dimethylallyl diphosphate synthase. Illustrative examples of nucleotide sequences include but are not limited to: (AY062212; *Escherichia coli*) and (NC_002947, locus_tag PP0606; *Pseudomonas putida* KT2440).

In some embodiments, "cross talk" (or interference) between the host cell's own metabolic processes and those processes involved with the production of IPP as provided by the present invention are minimized or eliminated entirely. For example, cross talk is minimized or eliminated entirely when the host microorganism relies exclusively on the DXP pathway for synthesizing IPP, and a MEV pathway is introduced to provide additional IPP. Such a host organisms would not be equipped to alter the expression of the MEV pathway enzymes or process the intermediates associated with the MEV pathway. Organisms that rely exclusively or predominately on the DXP pathway include, for example, *Escherichia coli*.

In some embodiments, the host cell produces IPP via the MEV pathway, either exclusively or in combination with the DXP pathway. In other embodiments, a host's DXP pathway is functionally disabled so that the host cell produces IPP exclusively through a heterologously introduced MEV pathway. The DXP pathway can be functionally disabled by disabling gene expression or inactivating the function of one or more of the DXP pathway enzymes.

$C_5$ Compounds $C_5$ compounds of the invention generally are derived from IPP or DMAPP. These compounds are also known as hemiterpenes because they are derived from a single isoprene unit (IPP or DMAPP).

Isoprene

Isoprene, whose structure is

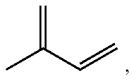

is found in many plants. Isoprene is made from IPP by isoprene synthase. Illustrative examples of suitable nucleotide sequences include but are not limited to: (AB198190; *Populus alba*) and (AJ294819; *Polulus alba×Polulus tremula*).

$C_{10}$ Compounds $C_{10}$ compounds of the invention generally derived from geranyl pyrophosphate (GPP) which is made by the condensation of IPP with DMAPP. An enzyme known to catalyze this step is, for example, geranyl pyrophosphate synthase. These $C_{10}$ compounds are also known as monoterpenes because they are derived from two isoprene units.

Figure 2:
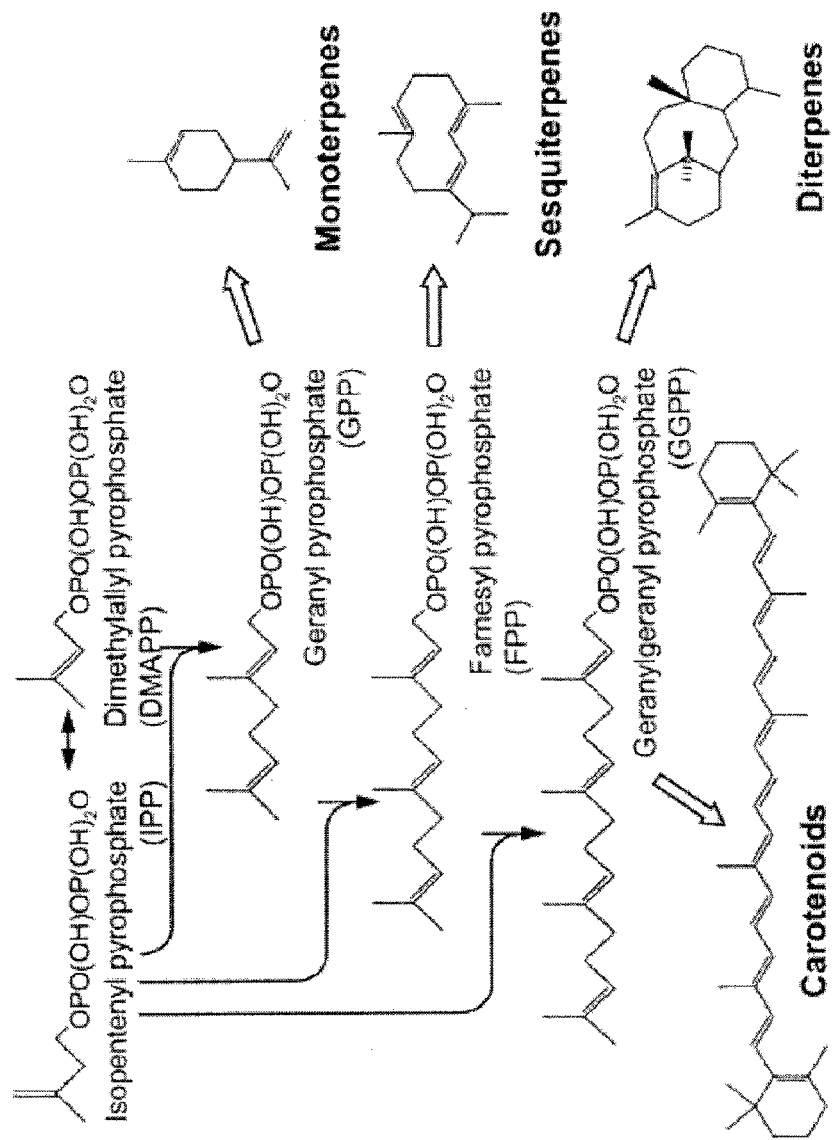
FIG. 2 is a schematic representation of the conversion of isopentenyl pyrophosphate ("IPP") and dimethylallyl pyrophosphate ("DMAPP") to geranyl pyrophosphate ("GPP"), farnesyl pyrophosphate ("FPP"), and geranylgeranyl pyrophosphate ("GGPP"), and the synthesis of various isoprenoids.

FIG. 2 shows schematically how IPP and DMAPP can produce GPP, which can be further processed to a monoterpene.

Illustrative examples of nucleotide sequences for geranyl pyrophosphate synthase include but are not limited to: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus AP11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Menthaxpiperita*), (AF182827; *Menthaxpiperita*), (MP1249453; *Menthaxpiperitax*), (PZE431697, Locus CAD24425; *Paracoccus zeaxanthinifaciens*), (AY866498; *Picrorhiza kurrooa*), (AY351862; *Vitis vinifera*), and (AF203881, Locus AAF12843; *Zymomonas mobilis*).

GPP is then subsequently converted to a variety of $C_{10}$ compounds. Illustrative examples of $C_{10}$ compounds include but are not limited:

Carene

Carene, whose structure is

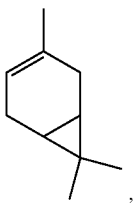

is found in the resin of many trees, particularly pine trees. Carene is made from GPP from carene synthase. Illustrative examples of suitable nucleotide sequences include but are not limited to: (AF461-460, REGION 43 . . . 1926; *Picea abies*) and (AF527416, REGION: 78 . . . 1871; *Salvia stenophylla*).

Geraniol

Geraniol (also known as rhodnol), whose structure is

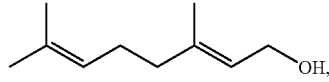

sis the main component of oil-of-rose and palmarosa oil. It also occurs in geranium, lemon, and citronella. Geraniol is made from GPP by geraniol synthase. Illustrative examples of suitable nucleotide sequences include but are not limited to: (AJ457070; *Cinnamomum tenuipilum*), (AY362553; *Ocimum basilicum*), (DQ234300; *Perilla frutescens* strain 1864), (DQ234299; *Perilla citriodora* strain 1861), (DQ234298; *Perilla citriodora* strain 4935), and (DQ088667; *Perilla citriodora*)

Linalool

Linalool, whose structure is

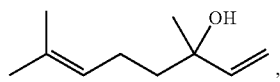

is found in many flowers and spice plants such as coriander seeds. Linalool is made from GPP by linalool synthase. Illustrative examples of a suitable nucleotide sequence include but are not limited to: (AF497-485; *Arabidopsis thaliana*), (AC002294, Locus AAB71482; *Arabidopsis thaliana*), (AY059757; *Arabidopsis thaliana*), (NM_104793; *Arabidopsis thaliana*), (AF154124; *Artemisia annua*), (AF067603; *Clarkia breweri*), (AF067602; *Clarkia concinna*), (AF067601; *Clarkia breweri*), (U58314; *Clarkia breweri*), (AY840091; *Lycopersicon esculentum*), (DQ263741; *Lavandula angustifolia*), (AY083653; *Mentha citrate*), (AY693647; *Ocimum basilicum*), (XM_463918; *Oryza sativa*), (AP004078, Locus BAD07605; *Oryza sativa*), (XM_463918, Locus XP_463918; *Oryza sativa*), (AY917193; *Perilla citriodora*), (AF271259; *Perilla frutescens*), (AY473623; *Picea abies*), (DQ195274; *Picea sitchensis*), and (AF444798; *Perilla frutescens* var. *crispa* cultivar No. 79).

Limonene

Limonene, whose structure is

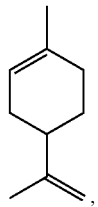

is found in the rind of citrus fruits and peppermint. Limonene is made from GPP by limonene synthase. Illustrative examples of suitable nucleotide sequences include but are not limited to: (+)-limonene synthases (AF514287, REGION: 47 . . . 1867; *Citrus limon*) and (AY055214, REGION: 48 . . . 1889; *Agastache rugosa*) and (−)-limonene synthases (DQ195275, REGION: 1 . . . 1905; *Picea sitchensis*), (AF006193, REGION: 73 . . . 1986; *Abies grandis*), and (MHC4SLSP, REGION: 29 . . . 1828; *Mentha spicata*).

Myrcene

Myrcene, whose structure is

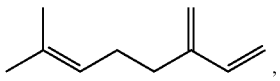

is found in the essential oil in many plants including bay, verbena, and myrcia from which it gets its name. Myrcene is made from GPP by myrcene synthase. Illustrative examples of suitable nucleotide sequences include but are not limited to: (U87908; *Abies grandis*), (AY195609; *Antirrhinum majus*), (AY195608; *Antirrhinum majus*), (NM_127982; *Arabidopsis thaliana* TPS10), (NM_113485; *Arabidopsis thaliana* ATTPS-CIN), (NM_113483; *Arabidopsis thaliana* ATTPS-CIN), (AF271259; *Perilla frutescens*), (AY473626; *Picea abies*), (AF369919; *Picea abies*), and (AJ304839; *Quercus ilex*).

Ocimene

α- and β-Ocimene, whose structures are

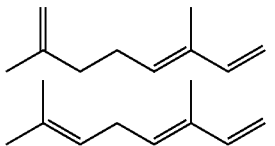

are found in a variety of plants and fruits including *Ocimum basilicum* and is made from GPP by ocimene synthase. Illustrative examples of suitable nucleotide sequences include but are not limited to: (AY195607; *Antirrhinum majus*), (AY195609; *Antirrhinum majus*), (AY195608; *Antirrhinum majus*), (AK221024; *Arabidopsis thaliana*), (NM_113485; *Arabidopsis thaliana* ATTPS-CIN), (NM_113483; *Arabidopsis thaliana* ATTPS-CIN), (NM_117775; *Arabidopsis thaliana* ATTPS03), (NM_001036574; *Arabidopsis thaliana* ATTPS03), (NM_127982; *Arabidopsis thaliana* TPS10), (AB110642; *Citrus unshiu* CitMTSL4), and (AY575970; *Lotus corniculatus* var. *japonicus*).

α-Pinene

α-Pinene, whose structure is

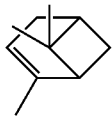

is found in pine trees and eucalyptus. α-Pinene is made from GPP by α-pinene synthase. Illustrative examples of suitable nucleotide sequences include but are not limited to: (+)α-pinene synthase (AF543530, REGION: 1 . . . 1887; *Pinus taeda*), (−)α-pinene synthase (AF543527, REGION: 32 . . . 1921; *Pinus taeda*), and (+)/(−)α-pinene synthase (AGU87909, REGION: 6111892; *Abies grandis*).

β-Pinene

β-Pinene, whose structure is

is found in pine trees, rosemary, parsley, dill, basil, and rose. β-Pinene is made from GPP by β-pinene synthase. Illustrative examples of suitable nucleotide sequences include but are not limited to: (−)β-pinene synthases (AF276072, REGION: 1 . . . 1749; *Artemisia annua*) and (AF514288, REGION: 26 . . . 1834; *Citrus limon*).

Sabinene

Sabinene, whose structure is

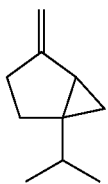

is found in black pepper, carrot seed, sage, and tea trees. Sabinene is made from GPP by sabinene synthase. An illustrative example of a suitable nucleotide sequence includes but is not limited to AF051901, REGION: 26 . . . 1798 from *Salvia officinalis*.

γ-Terpinene

γ-Terpinene, whose structure is

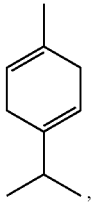

is a constituent of the essential oil from citrus fruits. Biochemically, γ-terpinene is made from GPP by a γ-terpinene synthase. Illustrative examples of suitable nucleotide sequences include: (AF514286, REGION: 30 . . . 1832 from *Citrus limon*) and (AB110640, REGION 1 . . . 1803 from *Citrus unshiu*).

Terpinolene

Terpinolene, whose structure is

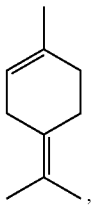

is found in black currant, cypress, guava, lychee, papaya, pine, and tea. Terpinolene is made from GPP by terpinolene synthase. An illustrative example of a suitable nucleotide sequence includes but is not limited to AY906866, REGION: 10 . . . 1887 from *Pseudotsuga menziesii*.

C$_{15}$ Compounds

C$_{15}$ compounds of the invention generally derive from farnesyl pyrophosphate (FPP) which is made by the condensation of two molecules of IPP with one molecule of DMAPP. An enzyme known to catalyze this step is, for example, farnesyl pyrophosphate synthase. These C$_{15}$ compounds are also known as sesquiterpenes because they are derived from three isoprene units.

FIG. 2 shows schematically how IPP and DMAPP can be combined to produce FPP, which can be further processed to a sesquiterpene.

Illustrative examples of nucleotide sequences for farnesyl pyrophosphate synthase include but are not limited to: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *Schizosaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), and (MZEFPS; *Zea mays*).

Alternatively, FPP can also be made by adding IPP to GPP. Illustrative examples of nucleotide sequences encoding for an enzyme capable of this reaction include but are not limited to: (AE000657, Locus AAC06913; *Aquifex aeolicus* VF5), (NM_202836; *Arabidopsis thaliana*), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP_873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; *Leptospira interrogans* serovar *Copenhageni* str. *Fiocruz* L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisae*), (CP000031, Locus AAV93568; *Silicibacter pomeroyi* DSS-3), (AE008481, Locus AAK99890; *Streptococcus pneumoniae* R6), and (NC_004556, Locus NP_779706; *Xylella fastidiosa* Temecula1).

FPP is then subsequently converted to a variety of C$_{15}$ compounds. Illustrative examples of C$_{15}$ compounds include but are not limited to:

Amorphadiene

Amorphadiene, whose structure is

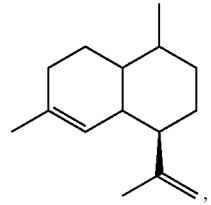

is a precursor to artemisinin which is made by *Artemisia anna*. Amorphadiene is made from FPP by amorphadiene synthase. An illustrative example of a suitable nucleotide sequence is SEQ ID NO. 37 of U.S. Pat. No. 7,192,751.

α-Farnesene

α-Farnesene, whose structure is

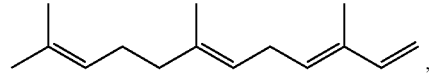

is found in various biological sources including but not limited to the Dufour's gland in ants and in the coating of apple and pear peels. α-Farnesene is made from FPP by α-farnesene synthase. Illustrative examples of suitable nucleotide sequences include but are not limited to DQ309034 from *Pyrus communis* cultivar *d'Anjou* (pear; gene name AFS1) and AY182241 from *Malus domestica* (apple; gene AFS1). Pechouus et al., *Planta* 219(1):84-94 (2004).

β-Farnesene

β-Farnesene, whose structure is

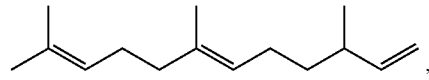

is found in various biological sources including but not limited to aphids and essential oils such as from peppermint. In some plants such as wild potato, β-farnesene is synthesized as a natural insect repellent. β-Farnesene is made from FPP by β-farnesene synthase. Illustrative examples of suitable nucleotide sequences include but is not limited to GenBank accession number AF024615 from *Mentha×piperita* (peppermint; gene Tspa11), and AY835398 from *Artemisia annua*. Picaud et al., *Phytochemistry* 66(9): 961-967 (2005).

Farnesol

Farnesol, whose structure is

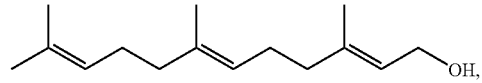

is found in various biological sources including insects and essential oils such as from cintronella, neroli, cyclamen, lemon grass, tuberose, and rose. Farnesol is made from FPP by a hydroxylase such as farnesol synthase. Illustrative examples of suitable nucleotide sequences include but are not limited to GenBank accession number AF529266 from *Zea mays* and YDR481c from *Saccharomyces cerevisiae* (gene Pho8). Song, L., *Applied Biochemistry and Biotechnology* 128:149-158 (2006).

Nerolidol

Nerolidol, whose structure is

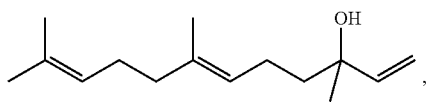

is also known as peruviol, and is found in various biological sources including as essential oils such as from neroli, ginger, jasmine, lavender, tea tree, and lemon grass. Nerolidol is made from FPP by a hydroxylase such as nerolidol synthase. An illustrative example of a suitable nucleotide sequence includes but is not limited to AF529266 from *Zea mays* (maize; gene tps1).

Patchoulol

Patchoulol, whose structure is

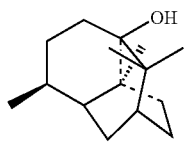

is also known as patchouli alcohol and is a constituent of the essential oil of *Pogostemon patchouli*. Patchouliol is made from FPP by patchouliol synthase. An illustrative example of a suitable nucleotide sequence includes but is not limited to AY508730 REGION: 1 . . . 1659 from *Pogostemon cablin*.

Valencene

Valencene, whose structure is

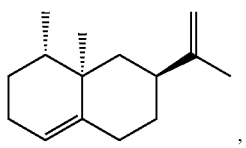

is one of the main chemical components of the smell and flavour of oranges and is found in orange peels. Valencene is made from FPP by nootkatone synthase. Illustrative examples of a suitable nucleotide sequence includes but is not limited to AF441124 REGION: 1 . . . 1647 from *Citrus sinensis* and AY917195 REGION: 1 . . . 1653 from *Perilla frutescens*.

$C_{20}$ Compounds $C_{20}$ compounds of the invention generally derived from geranylgeraniol pyrophosphate (GGPP) which is made by the condensation of three molecules of IPP with one molecule of DMAPP. An enzyme known to catalyze this step is, for example, geranylgeranyl pyrophosphate synthase. These $C_{20}$ compounds are also known as diterpenes because they are derived from four isoprene units.

FIG. 2 shows schematically how IPP and DMAPP can be combined to produce GGPP, which can be further processed to a diterpene, or can be further processed to produce a carotenoid.

Illustrative examples of nucleotide sequences for geranylgeranyl pyrophosphate synthase include but are not limited to: (ATHGERPYRS; *Arabidopsis thaliana*), (BT005328; *Arabidopsis thaliana*), (NM_119845; *Arabidopsis thaliana*), (NZ_AAJM01000380, Locus ZP_00743052; *Bacillus thuringiensis* serovar *israelensis*, ATCC 35646 sq1563), (CRGGPPS; *Catharanthus roseus*), (NZ_AABF02000074, Locus ZP_00144509; *Fusobacterium nucleatum* subsp. *vincentii*, ATCC 49256), (GFGG-PPSGN; *Gibberella fujikuroi*), (AY371321; *Ginkgo biloba*), (AB055496; *Hevea brasiliensis*), (AB017971; *Homo sapiens*), (MC1276129; *Mucor circinelloides* f. *lusitanicus*), (AB016044; *Mus musculus*), (AABX01000298, Locus NCU01427; *Neurospora crassa*), (NCU20940; *Neurospora crassa*), (NZ_AAKL01000008, Locus ZP_00943566; *Ralstonia solanacearum* UW551), (AB118238; *Rattus norvegicus*), (SCU31632; *Saccharomyces cerevisiae*), (AB016095; *Synechococcus elongates*), (SAGGPS; *Sinapis alba*), (SSOGDS; *Sulfolobus acidocaldarius*), (NC_007759, Locus YP_461832; *Syntrophus aciditrophicus* SB), and (NC_006840, Locus YP_204095; *Vibrio fischeri* ES114).

Alternatively, GGPP can also be made by adding IPP to FPP. Illustrative examples of nucleotide sequences encoding an enzyme capable of this reaction include but are not limited to: (NM_112315; *Arabidopsis thaliana*), (ERWCRTE; *Pantoea agglomerans*), (D90087, Locus BAA14124; *Pantoea ananatis*), (X52291, Locus CAA36538; *Rhodobacter capsulatus*), (AF195122, Locus AAF24294; *Rhodobacter sphaeroides*), and (NC_004350, Locus NP_721015; *Streptococcus mutans* UA159).

GGPP is then subsequently converted to a variety of $C_{20}$ isoprenoids. Illustrative examples of $C_{20}$ compounds include but are not limited to:

Geranylgeraniol

Geranylgeraniol, whose structure is

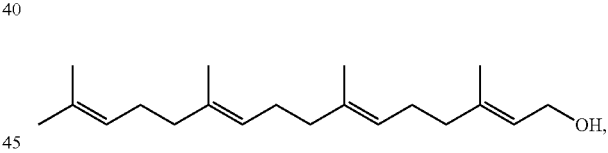

is a constituent of wood oil from *Cedrela toona* and of linseed oil. Geranylgeraniol can be made by e.g., adding to the expression constructs a phosphatase gene after the gene for a GGPP synthase.

Abietadiene

Abietadiene encompasses the following isomers:

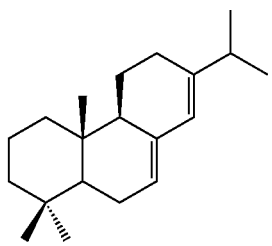

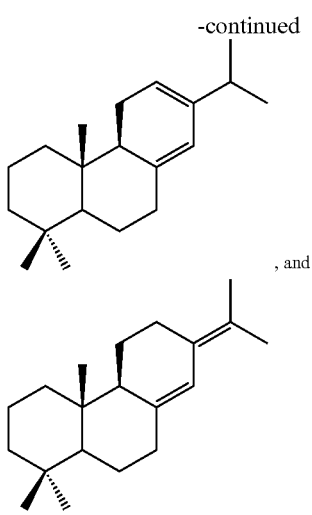
, and and is found in trees such as *Abies grandis*. Abietadiene is made by abietadiene synthase. An illustrative example of a suitable nucleotide sequence includes but are not limited to: (U50768; *Abies grandis*) and (AY473621; *Picea abies*).

$C_{20+}$ Compounds $C_{20+}$ compounds are also within the scope of the present invention. Illustrative examples of such compounds include sesterterpenes ($C_{25}$ compound made from five isoprene units), triterpenes ($C_{30}$ compounds made from six isoprene units), and tetraterpenes ($C_{40}$ compound made from eight isoprene units). These compounds are made by using similar methods described herein and substituting or adding nucleotide sequences for the appropriate synthase(s).

Engineering Pathways

The present invention utilizes an engineered MEV and/or DXP pathway to effect the high-level production of isoprenoids in a host cell. The pathway is typically engineered via recombinant DNA technology by expressing heterologous sequences encoding enzymes in at least one of these pathways.

The subject nucleotide acids can be expressed by a single or multiple vectors. For example, a single expression vector can comprise at least two, three, four, five, or all of the heterologous sequences encoding the entire MEV or DXP pathway enzymes. While the choice of single or multiple vectors may depend on the size of the heterologous sequences and the capacity of the vectors, it will largely dependent on the overall yield of a given isoprenoid that the vector is able to provide when expressed in a selected host cell. The subject vectors can stay replicable episomally, or as an integral part of the host cell genome. Typically, the latter is preferred for a sustained propagation of the host cell.

In certain host cells, the one or more heterologous sequences encoding the MEV or DXP pathway enzymes may be controlled by one or more operons. In some instances, a two or three operon system provides a higher yield of an isoprenoid over a single operon system.

Where desired, the subject nucleic acid sequences can be modified to reflect the codon preference of a selected host cell to effect a higher expression of such sequences in a host cell. For example, the subject nucleotide sequences will in some embodiments be modified for yeast codon preference. See, e.g., Bennetzen and Hall (1982) *J. Biol. Chem.* 257(6): 3026-3031. As another non-limiting example, the nucleotide sequences will in other embodiments be modified for *E. coli* codon preference. See, e.g., Gouy and Gautier (1982) *Nucleic Acids Res.* 10(22):7055-7074; Eyre-Walker (1996) *Mol. Biol. Evol.* 13(6):864-872. See also Nakamura et al. (2000) *Nucleic Acids Res.* 28(1):292. Codon usage tables for many organisms are available, which can be used as a reference in designing sequences of the present invention. The use of prevalent codons of a given host microorganism generally increases the likelihood of translation, and hence the expression level of the desired sequences.

Preparation of the subject nucleic acids can be carried out by a variety of routine recombinant techniques and synthetic procedures. Briefly, the subject nucleic acids can be prepared genomic DNA fragments, cDNAs, and RNAs, all of which can be extracted directly from a cell or recombinantly produced by various amplification processes including but not limited to PCR and rt-PCR.

Direct chemical synthesis of nucleic acids typically involves sequential addition of 3'-blocked and 5'-blocked nucleotide monomers to the terminal 5'-hydroxyl group of a growing nucleotide polymer chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (for example, Matteuci et al. (1980) Tet. Lett. 521:719; U.S. Pat. No. 4,500, 707 to Caruthers et al.; and U.S. Pat. Nos. 5,436,327 and 5,700,637 to Southern et al.).

The level of transcription of a nucleic acid in a host microorganism can be increased in a number of ways. For example, this can be achieved by increasing the copy number of the nucleotide sequence encoding the enzyme (e.g., by using a higher copy number expression vector comprising a nucleotide sequence encoding the enzyme, or by introducing additional copies of a nucleotide sequence encoding the enzyme into the genome of the host microorganism, for example, by recA-mediated recombination, use of "suicide" vectors, recombination using lambda phage recombinase, and/or insertion via a transposon or transposable element). In addition, it can be carried out by changing the order of the coding regions on the polycistronic mRNA of an operon or breaking up an operon into individual genes, each with its own control elements, or increasing the strength of the promoter (transcription initiation or transcription control sequence) to which the enzyme coding region is operably linked (for example, using a consensus arabinose- or lactose-inducible promoter in an *Escherichia coli* host microorganism in place of a modified lactose-inducible promoter, such as the one found in pBluescript and the pBBR1MCS plasmids), or using an inducible promoter and inducing the inducible-promoter by adding a chemical to a growth medium. The level of translation of a nucleotide sequence in a host microorganism can be increased in a number of ways, including, but not limited to, increasing the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence. Determination of preferred codons and rare codon tRNAs can be based on a sequence analysis of genes derived from the host microorganism.

The activity of a MEV, DXP, or prenyltransferase in a host can be altered in a number of ways, including, but not limited to, expressing a modified form of the enzyme that exhibits increased solubility in the host cell, expressing an altered form of the enzyme that lacks a domain through which the activity of the enzyme is inhibited, expressing a modified form of the enzyme that has a higher Kcat or a lower Km for the substrate, or expressing an altered form of the enzyme that is not affected by feed-back or feed-forward regulation by another molecule in the pathway. Such variant enzymes can also be isolated through random mutagenesis of a broader specificity enzyme, as described below, and a nucleotide sequence encoding such variant enzyme can be expressed from an expression vector or from a recombinant gene integrated into the genome of a host microorganism.

The subject vector can be constructed to yield a desired level of copy numbers of the encoded enzyme. In some embodiments, the subject vectors yield at least 10, between 10 to 20, between 20-50, between 50-100, or even higher than 100 copies of the HMG-CoA reductase, mevalonate kinase, or both. Low copy number plasmids generally provide fewer than about 20 plasmid copies per cell; medium copy number plasmids generally provide from about 20 plasmid copies per cell to about 50 plasmid copies per cell, or from about 20 plasmid copies per cell to about 80 plasmid copies per cell; and high copy number plasmids generally provide from about 80 plasmid copies per cell to about 200 plasmid copies per cell, or more.

Suitable low copy expression vectors for *Escherichia coli* include, but are not limited to, pACYC184, pBeloBac11, pBR332, pBAD33, pBBR1MCS and its derivatives, pSC101, SuperCos (cosmid), and pWE15 (cosmid). Suitable medium copy expression vectors for *Escherichia coli* include, but are not limited to pTrc99A, pBAD24, and vectors containing a ColE1 origin of replication and its derivatives. Suitable high copy number expression vectors for *Escherichia coli* include, but are not limited to, pUC, pBluescript, pGEM, and pTZ vectors. Suitable low-copy (centromeric) expression vectors for yeast include, but are not limited to, pRS415 and pRS416 (Sikorski & Hieter (1989) Genetics 122:19-27). Suitable high-copy 2 micron expression vectors in yeast include, but are not limited to, pRS425 and pRS426 (Christainson et al. (1992) Gene 110:119-122). Alternative 2 micron expression vectors include non-selectable variants of the 2 micron vector (Bruschi & Ludwig (1988) Curr. Genet. 15:83-90) or intact 2 micron plasmids bearing an expression cassette (as exemplified in U.S. Pat. Appl. 20050084972) or 2 micron plasmids bearing a defective selection marker such as LEU2d (Erhanrt et al. (1983) J. Bacteriol. 156 (2): 625-635) or URA3d (Okkels (1996) Annals of the New York Academy of Sciences 782(1): 202-207).

Regulatory elements include, for example, promoters and operators can also be engineered to increase the metabolic flux of the MEV or DXP pathways by increasing the expression of one or more genes that play a significant role in determining the overall yield of an isoprenoid produced. A promoter is a sequence of nucleotides that initiates and controls the transcription of a nucleic acid sequence by an RNA polymerase enzyme. An operator is a sequence of nucleotides adjacent to the promoter that functions to control transcription of the desired nucleic acid sequence. The operator contains a protein-binding domain where a specific repressor protein can bind. In the absence of a suitable repressor protein, transcription initiates through the promoter. In the presence of a suitable repressor protein, the repressor protein binds to the operator and thereby inhibits transcription from the promoter. Promotors and operators are also referred to as transcriptional regulators.

In some embodiments of the present invention, promoters used in expression vectors are inducible. In other embodiments, the promoters used in expression vectors are constitutive. In some embodiments, one or more nucleic acid sequences are operably linked to an inducible promoter, and one or more other nucleic acid sequences are operably linked to a constitutive promoter.

Non-limiting examples of suitable promoters for use in prokaryotic host cells include a bacteriophage T7 RNA polymerase promoter; a trp promoter; a lac operon promoter; a hybrid promoter, for example, a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, for example, U.S. Patent Publication No. 20040131637), a pagC promoter (Pulkkinen and Miller, J. Bacteriol. (1991) 173(1):86-93; Alpuche-Aranda et al. (1992) Proc. Natl. Acad. Sci. USA. 89(21): 10079-83), a nirB promoter (Harborne et al. (1992) Mol. Micro. 6:2805-2813), and the like (see, for example, Dunstan et al. (1999). Infect. Immun. 67:5133-5141; McKelvie et al. (2004) Vaccine 22:3243-3255; and Chatfield et al. (1992) Biotechnol. 10:888-892); a sigma70 promoter, for example, a consensus sigma70 promoter (see, for example, GenBank Accession Nos. AX798980, AX798961, and AX798183); a stationary phase promoter, for example, a dps promoter, an spv promoter, and the like; a promoter derived from the pathogenicity island SPI-2 (see, for example, WO96/17951); an actA promoter (see, for example, Shetron-Rama et al. (2002) Infect. Immun. 70:1087-1096); an rpsM promoter (see, for example, Valdivia and Falkow (1996) Mol. Microbiol. 22:367 378); a tet promoter (see, for example, Hillen et al. (1989) In Saenger W. and Heinemann U. (eds) Topics in Molecular and Structural Biology, Protein-Nucleic Acid Interaction. Macmillan, London, UK, Vol. 10, pp. 143-162); an SP6 promoter (see, for example, Melton et al. (1984) Nucl. Acids Res. 12:7035-7056); and the like.

In some embodiment, the total activity of a heterologous MEV or DXP enzyme that plays a larger role in the overall yield of an isoprenoid relative to other enzymes in the respective pathways is increased by expressing the enzyme from a strong promoter. Suitable strong promoters for *Escherichia coli* include, but are not limited to Trc, Tac, T5, T7, and $P_{Lambda}$. In another embodiment of the present invention, the total activity of the one or more MEV pathway enzymes in a host is increased by expressing the enzyme from a strong promoter on a high copy number plasmid. Suitable examples, for *Escherichia coli* include, but are not limited to using Trc, Tac, T5, T7, and $P_{Lambda}$ promoters with pBAD24, pBAD18, pGEM, pBluescript, pUC, and pTZ vectors.

Non-limiting examples of suitable promoters for use in eukaryotic host cells include, but are not limited to, a CMV immediate early promoter, an HSV thymidine kinase promoter, an early or late SV40 promoter, LTRs from retroviruses, and a mouse metallothionein-I promoter.

Non-limiting examples of suitable constitutive promoters for use in prokaryotic host cells include a sigma70 promoter (for example, a consensus sigma70 promoter). Non-limiting examples of suitable inducible promoters for use in bacterial host cells include the pL of bacteriophage λ; Plac; Ptrp; Ptac (Ptrp-lac hybrid promoter); an isopropyl-beta-D44 thiogalactopyranoside (IPTG)-inducible promoter, for example, a lacZ promoter; a tetracycline inducible promoter; an arabinose inducible promoter, for example, PBAD (see, for example, Guzman et al. (1995) J. Bacteriol. 177:4121-4130); a xylose-inducible promoter, for example, Pxyl (see, for example, Kim et al. (1996) Gene 181:71-76); a GAL1 promoter; a tryptophan promoter; a lac promoter; an alcohol-inducible promoter, for example, a methanol-inducible promoter, an ethanol-inducible promoter; a raffinose-inducible promoter; a heat-inducible promoter, for example, heat inducible lambda PL promoter; a promoter controlled by a heat-sensitive repressor (for example, CI857-repressed lambda-based expression vectors; see, for example, Hoffmann et al. (1999) FEMS Microbiol Lett. 177(2):327-34); and the like.

Non-limiting examples of suitable constitutive promoters for use in yeast host cells include an ADH1, an ADH2, a PGK, or a LEU2 promoter. Non-limiting examples of suitable inducible promoters for use in yeast host cells include, but are not limited to, a divergent galactose-inducible promoter such as a GAL 1 or a GAL 10 promoter (West at al. (1984) Mol. Cell. Biol. 4(11):2467-2478), or a CUP1 promoter. Where desired, the subject vector comprise a promoter that is stronger than a native E. Coli Lac promoter.

Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25.).

The genes in the expression vector typically will also encode a ribosome binding site to direct translation (that is, synthesis) of any encoded mRNA gene product. For suitable ribosome binding sites for use in Escherichia coli, see Shine et al. (1975) Nature 254:34, and Steitz, in Biological Regulation and Development: Gene Expression (ed. R. F. Goldberger), vol. 1, p. 349, 1979, Plenum Publishing, N.Y. Insertion of the ribosome binding site encoding nucleotide sequence 5'-AAAACA-3' upstream of a coding sequence facilitates efficient translation in a yeast host microorganism (Looman et al. (1993) Nuc. Ac. Res. 21:4268-4271; Yun et. al. (1996) Mol. Microbiol. 19:1225-1239).

Other regulatory elements that may be used in an expression vector include transcription enhancer elements and transcription terminators. See, for example, Bitter et al. (1987) Methods in Enzymology, 153:516-544.

An expression vector may be suitable for use in particular types of host microorganisms and not others. One of ordinary skill in the art, however, can readily determine through routine experimentation whether a particular expression vector is suited for a given host microorganism. For example, the expression vector can be introduced into the host organism, which is then monitored for viability and expression of any genes contained in the vector.

The expression vector may also contain one or more selectable marker genes that, upon expression, confer one or more phenotypic traits useful for selecting or otherwise identifying host cells that carry the expression vector. Non-limiting examples of suitable selectable markers for eukaryotic cells include dihydrofolate reductase and neomycin resistance. Non-limiting examples of suitable selectable markers for prokaryotic cells include tetracycline, ampicillin, chloramphenicol, carbenicillin, and kanamycin resistance.

For production of isoprenoid at an industrial scale, it may be impractical or too costly to use a selectable marker that requires the addition of an antibiotic to the fermentation media. Accordingly, some embodiments of the present invention employ host cells that do not require the use of an antibiotic resistance conferring selectable marker to ensure plasmid (expression vector) maintenance. In these embodiments of the present invention, the expression vector contains a plasmid maintenance system such as the 60-kb IncP (RK2) plasmid, optionally together with the RK2 plasmid replication and/or segregation system, to effect plasmid retention in the absence of antibiotic selection (see, for example, Sia et al. (1995) J. Bacteriol. 177:2789-97; Pansegrau et al. (1994) J. Mol. Biol. 239:623-63). A suitable plasmid maintenance system for this purpose is encoded by the parDE operon of RK2, which codes for a stable toxin and an unstable antitoxin. The antitoxin can inhibit the lethal action of the toxin by direct protein-protein interaction. Cells that lose the expression vector that harbors the parDE operon are quickly deprived of the unstable antitoxin, resulting in the stable toxin then causing cell death. The RK2 plasmid replication system is encoded by the trfA gene, which codes for a DNA replication protein. The RK2 plasmid segregation system is encoded by the parCBA operon, which codes for proteins that function to resolve plasmid multimers that may arise from DNA replication.

The subject vectors can be introduced into a host cell stably or transiently by variety of established techniques. For example, one method involves a calcium chloride treatment wherein the expression vector is introduced via a calcium precipitate. Other salts, for example calcium phosphate, may also be used following a similar procedure. In addition, electroporation (that is, the application of current to increase the permeability of cells to nucleic acids) may be used. Other transformation methods include microinjection, DEAE dextran mediated transformation, and heat shock in the presence of lithium acetate. Lipid complexes, liposomes, and dendrimers may also be employed to transfect the host microorganism.

Upon transformation, a variety of methods can be practiced to identify the host cells into which the subject vectors have been introduced. One exemplary selection method involves subculturing individual cells to form individual colonies, followed by testing for expression of the desired gene product. Another method entails selecting transformed host cells based upon phenotypic traits conferred through the expression of selectable marker genes contained within the expression vector. Those of ordinary skill can identify genetically modified host cells using these or other methods available in the art.

The introduction of various pathway sequences of the invention into a host cell can be confirmed by methods such as PCR, Southern blot or Northern blot hybridization. For example, nucleic acids can be prepared from the resultant host cells, and the specific sequences of interest can be amplified by PCR using primers specific for the sequences of interest. The amplified product is subjected to agarose gel electrophoresis, polyacrylamide gel electrophoresis or capillary electrophoresis, followed by staining with ethidium bromide, SYBR Green solution or the like, or detection of DNA with a UV detection. Alternatively, nucleic acid probes specific for the sequences of interest can be employed in a hybridization reaction. The expression of a specific gene sequence can be ascertained by detecting the corresponding mRNA via reveres-transcription coupled PCR, Northern blot hybridization, or by immunoassays using antibodies reactive with the encoded gene product. Exemplary immunoassays include but are not limited to ELISA, radioimmunoassays, and sandwich immunoassays.

The enzymatic activity of a given pathway enzyme can be assayed by a variety of methods known in the art. In general, the enzymatic activity can be ascertained by the formation of the product or conversion of a substrate of an enzymatic reaction that is under investigation. The reaction can take place in vitro or in vivo. For example, the relative activity of HMG-CoA reductase and HMG-CoA synthase in a cell can be measured by the steady state level of HMG-CoA in a cell. HMG-CoA can be extracted by Tricholoroacetic Acid (TCA), followed by analyzing the extracted material via Liquid Chromatography/Mass Spectrometry. The activity of mevalonate kinase can be demonstrated by the formation of mevalonate 5-phosphate. The relative activity of mevalonate kinase and HMG-CoA reductase can be measured by the steady state level of mevalonate, which can be determined by Gas Chromatography/Mass spectrometry. See e.g., WO05033287, which is incorporated herein by reference.

The yield of an isoprenoid via one or more metabolic pathways disclosed herein can be augmented by inhibiting reactions that divert intermediates from productive steps towards formation of the isoprenoid product. Inhibition of the unproductive reactions can be achieved by reducing the expression and/or activity of enzymes involved in one or more unproductive reactions. Such reactions include side reactions of the TCA cycle that lead to fatty acid biosynthesis, alanine biosynthesis, the aspartate superpathway, gluconeogenesis, heme biosynthesis, and/or glutamate biosynthesis, at a level that affects the overall yield of an isoprenoid production. Additionally, the conversion of acetyl-CoA to acetate via the action of phosphotransacetylase is another example of unproductive side reaction. Therefore, where desired, "knocking out" or "knocking down" the pta gene that encodes phosphotransacetylase may also be carried in order to increase the yield of isoprenoid production. Depending on the specific isoprenoid of interest, one skilled in the art may choose to target additional unproductive steps. For example, where carotenoid is the isoprenoid of choice, one may opt to "knock out" or "knock down" one or more genes selected from the group consisting of gdhA, aceE, fdhF, yjiD, hnr or yjfP, ackA, appY, aspC, clp, clpP, clpXP, crcB, csdA, cyaA, evgS, fdhA, fdhD, feoB, fumA, glnE, glxR, gntK, hycI, lipB, lysU, modA, moeA, nadA, nuoC, nuoK, pflB, pitA, pst, pstC, pta, p-yjiD, sohA, stpA, yagR, yaiD, ybaS, ycfZ, ydeN, yebB, yedN, yfcC, ygiP, yibD, yjfP, yjhH, or yliE genes, or any other genes alone or in combination, the inhibition of which would result in a higher yield of carotenoid as described in U.S. Patent Application 20060121558, which is incorporated herein by reference.

A variety of methods are available for knocking out or knocking down a gene of interest. For example, a reduced gene expression may be accomplished by deletion, mutation, and/or gene rearrangement. It can also be carried out with the use of antisense RNA, siRNA, miRNA, ribozymes, triple stranded DNA, and transcription and/or translation inhibitors. In addition, transposons can be employed to disrupt gene expression, for example, by inserting it between the promoter and the coding region, or between two adjacent genes to inactivate one or both genes.

High Yields of Isoprenoid Compounds

The present invention provides compositions and methods for a robust production of isoprenoids by the use of isopentenyl pyrophosphate pathway enzymes that are under the control of at least one heterologous regulator or fermentation conditions, either alone or in combination.

In one aspect, a method of producing an isoprenoid involves the steps of (a) obtaining a plurality of host cells that comprise an enzymatic pathway for making isopentenyl pyrophosphate wherein the all of the pathway enzymes are under control of at least one heterologous transcriptional regulator; and (b) culturing the host cells in a medium under conditions that are suboptimal as compared to conditions that would provide for a maximum specific growth rate for the host cells. In some embodiments, the pathway is the mevalonate pathway. In other embodiments, the pathway is the DXP pathway. In other embodiments, the at least one heterologous transcriptional regulatory sequence is inducible. In other embodiments, the pathway enzymes are under control of a single transcriptional regulator. In other embodiments, the pathway enzymes are under control of multiple heterologous transcriptional regulators.

In some embodiments, the pathway comprises a nucleic acid sequence encoding a mevalonate pathway enzyme from a prokaryote having an endogenous mevalonate pathway. Non-limiting examples of suitable prokaryotes include those from the genera: *Actinoplanes, Archaeoglobus; Bdellovibrio; Borrelia, Chloroflexus; Enterococcus, Lactobacillus, Listeria; Oceanobacillus; Paracoccus, Pseudomonas, Staphylococcus, Streptococcus; Streptomyces, Thermoplasma;* and *Vibrio*. Non-limiting examples of specific strains include: *Archaeoglobus fulgidus; Bdellovibrio bacteriovorus; Borrelia burgdorferi, Chloroflexus aurantiacus; Enterococcus faecalis; Enterococcus faecium; Lactobacillus johnsonii; Lactobacillus plantarum; Lactococcus lactis; Listeria innocua; Listeria monocytogenes; Oceanobacillus iheyensis, Paracoccus zeaxanthinifaciens; Pseudomonas mevalonii; Staphylococcus aureus; Staphylococcus epidermidis; Staphylococcus haemolyticus; Streptococcus agalactiae; Streptomyces griseolosporeus; Streptococcus mutans; Streptococcus pneumoniae; Streptococcus pyogenes; Thermoplasma acidophilum, Thermoplasma volcanium; Vibrio cholerae; Vibrio parahaemolyticus;* and *Vibrio vulnificus;*

In another embodiment, the nucleic acid sequence encoding a mevalonate pathway enzyme is selected from acetyl-CoA thiolase, HMG-CoA synthase, HMG-CoA reductase, and mevalonate kinase. In another embodiment, the nucleic acid sequence encoding a mevalonate pathway enzyme is selected from acetyl-CoA thiolase, HMG-CoA synthase, HMG-CoA reductase, and mevalonate kinase and is from a prokaryote belonging to the genus *Enterococcus* or the genus *Pseudomonas* or the genus *Staphylococcus*. In another embodiment, the nucleic acid sequence encoding a mevalonate pathway enzyme is selected from acetyl-CoA thiolase, HMG-CoA synthase, HMG-CoA reductase, and mevalonate kinase and is from *Enterococcus faecalis* or from *Staphylococcus aureus*.

In another embodiment, nucleic acid sequence encoding a mevalonate pathway enzyme is a Class II HMG-CoA reductase. HMG-CoA reductases are generally classified into two classes, which are distinguishable based on sequence homology and/or enzymatic properties (see, for example, Hedl, et al., J. Bacteriology, 1927-1932, 2004, and Bochar, et al., Molec. Genet. Metab., 66, 122-127, 1999).

Class II HMG-CoA reductases can be characterized, in part, by their low sensitivity to statins, including but not limited to Atorvastatin, Cerivastatin, Fluvastatin, Lovastatin, Pravastatin, Simvastatin, in some embodiments, the Class II HMG-CoA reductase exhibits a statin inhibition constant greater than about 1 micromolar, 10 micromolar, or 100 micromolar. In other embodiments, the Class II HMG-CoA reductase has an inhibition constant for Lovastatin greater than that of the Class I HMG-CoA by a factor of at least about 10, 100, 1000, or 10,000. In other embodiments, the Class II HMG-CoA reductase has an inhibition constant for Lovastatin greater than that of the Class I HMG-CoA isolated from a *Homo sapien* by a factor of at least about 10, 100, 1000, or 10,000. In other embodiments, the Class II HMG-CoA reductase is from a prokaryote. In other embodiments, the Class II HMG-CoA reductase is from archae bacteria.

A prototypical Class II HMG-CoA reductase is derived from *Pseudomonas mevalonii*. Also encompassed in the invention are variant Class II HMG-CoA reductases exhibiting at least about 30%, 35%, 40%, 45%, 50%, 55%, 60%, 65%, 70%, 80%, 90%, or 95% identity as compared to the amino acid sequence of *P. mevalonii* HMG-CoA reductase. Further encompassed in the invention are variants having less than about 40%, 35%, 30%, 25%, 20%, or less, identity with an *H. Sapiens* HMG-CoA reductase. The identities of amino acid sequences can be determined by the methods described in Bochar, et al., Molec. Genet. Metab., 66, 122-127, 1999.

Non-limiting exemplary Class II HMG-CoA reductases include those derived from HMG-CoA reductases from: *Archaeoglobus fulgidus* (NC_000917), *Bdellovibrio bacteriovorus* (BX842650); *Borrelia burgdorferi* (AE001169); *Chloroflexus aurantiacus* (AJ299212); *Enterococcus faecalis* (AAO81155); *Enterococcus faecium* (AF290094); *Lactobacillus johnsonii* (AE017204); *Lactobacillus plantarum; Lactococcus lactis* (AE006387); *Listeria innocua* (CAC96053); *Listeria monocytogenes* (AE017324); *Oceanobacillus iheyensis* (NC_000917); *Paracoccus zeaxanthinifaciens* (AJ431696); *Pseudomonas mevalonii* (M24015); *Staphylococcus aureus* (AF290086); *Staphylococcus epidermidis* (AF290090); *Staphylococcus haemolyticus* (AF290088); *Streptococcus agalactiae* (CAD47046); *Streptomyces griseolosporeus* (AB037907); *Streptococcus mutans* (AAN58647); *Streptococcus pneumoniae* (AF290098); *Streptococcus pyogenes* (AF290096); *Thermoplasma acidophilum* (CAC11548), *Thermoplasma volcanium* (AL935253); *Vibrio cholerae* (AAF96622); *Vibrio parahaemolyticus* (BAC62311); and *Vibrio vulnificus* (AA007090).

The fermentation methods described herein relate to modulating the specific growth rate of the host cells. Often represented by the parameter $\mu$, the specific growth rate represents the rate of growth of cells per unit of biomass per unit time. The specific growth rate has the units of reciprocal time (1/t). The maximum specific growth rate for cells in a culture medium relates to the effect of substrate concentration on growth rate. Generally, cells will grow slowly at a low level of the substrate, and as the level of the substrate in the medium increases, so does the rate of cell growth. However, the rate of cell growth does not continue to rise indefinitely, and at high levels of substrate, a given increase in the amount of substrate will produce a smaller and smaller increase in the rate of cell growth. Therefore, the growth rate ultimately reaches a limit, which is often referred to as the maximum specific growth rate. A theoretical treatment of the relationship between growth rate in culture is well known to those skilled in the art, and is referred to as the Monod equation. See, for example, Pirt, Principles of Microbe and Cell Cultivation, Wiley, NY, 1975, pages 4-10. In this theoretical treatment, the maximum specific rate is an asymptotic limit that is never reached until an infinite level of substrate is reached. In practice, however, the maximum specific growth rate can be considered as being obtained when the conditions under investigation (e.g., a substrate level or temperature) support the fastest initial growth rate. For instance, in a fed-batch reactor, the initial condition where the nutrients are supplied in excess is treated as the conditions for the maximum growth rate. See, for example, Lee et al. (1996) *Trends Biotechnol.* 14: 98-105 and Korz et al. (1995) *J Biotechnology* 39:59-65. The conditions where a substrate is added to support the maximum specific growth rate is also sometimes referred to as unlimited growth. In addition, while the Monod equation describes the theoretical rate properties for a substrate that asymptotically approaches the maximum specific rate, for many substrates, rather than approaching the value as more substrate is added, a decrease in rate is seen at higher levels of substrate after a maximum rate is achieved, i.e., the maximum specific growth rate is achieved followed by a decrease in growth rate.

The maximum specific growth rate can also be applied with respect to temperature as well as to substrates. Generally, an organism will grow slowly at low temperatures, and will grow at a faster rate as the temperature increases up to a certain point, after which, the growth rate will decline. There will be a temperature at which the growth rate will be at a maximum level, this is the temperature at which the maximum growth rate is achieved. We have found that the production of isoprenoids can be increased by lowering the temperature below the temperature that supports the maximum specific growth rate.

The maximum specific growth rate can also be applied with respect to other additives to the fermentation than substrates. For instance, with respect to nutrients, vitamins, and minerals, there can be a low rate at low amounts of these components, the rate will get higher as the concentration of the component is increased, then, in some cases, at even higher concentrations of the components, the rate will decrease. The maximum specific growth rate is obtained where the concentration of the component supports the highest rate.

The maximum specific growth rate for a cell in a medium is often determined at the initial stages of the fermentation before inhibition by end product or intermediates, cell crowding, or other factors contribute to slowing down the rate of growth. For example the maximum growth rate is often determined during the exponential phase of growth rather than at the lag phase, deceleration phase, or the stationary phase. The concept of maximum specific growth rate can also be applied at later stages of the fermentation by taking into account the appropriate variables.

Accordingly, in some embodiments, host cells are cultured under conditions such that growth is less than about 90% of the maximum specific growth rate. In other embodiments, the host cells are cultured under conditions such that growth is less than about 80%, 75%, 60%, 50%, 40%, 30%, 25%, 20%, 10%, 5%, or 1%, or less, of the maximum specific growth rate.

In other embodiments, the host cells are cultured at a medium temperature is at least about 2° C., 4° C., 5° C., 6° C., 8° C., 10° C., 15° C., or 20° C. below the temperature that would provide for the maximum specific growth rate. By lowering the temperature growth is reduced, which in turn, reduces the formation of toxic byproducts in the medium and the generation of metabolic heat. Lowering culture temperature also reduces cellular oxygen demand which enables higher cell-densities to be obtained.

The temperature at which at which the maximum specific growth rate of a host cell can be achieved will depend on the type of host cell selected. This can be ascertained by growing the host cells under various temperatures over a defined period of time to derive the relevant growth curves. The temperature that supports the maximum specific growth rate can be determined by comparing the slopes of growth in the respective curves. In the case of *E. Coli*, the temperature for maximum specific growth rate is about 37° C. Accordingly, if *E. Coli* is the host cell to be used for fermentative production of isoprenoid, the fermentation temperature is below 37° C. If *S. cerevisiae* is employed, the temperature for maximum specific growth rate is about 30° C. Accordingly, if *S. cerevisiae* is the host cell to be used for fermentative production of isoprenoid, the fermentation temperature is below 30° C. Typically a desired temperature is about 2° C., 4° C., 5° C., 6, 8, 10° C., 15° C., and 20° C. below the temperature at which the maximum specific growth rate of the host cell can be achieved.

In other embodiments, the host cells are cultured in a fermentation medium comprises a carbon source present in an amount that is lower than that which would provide for a maximum specific growth rate. In certain embodiments, the host cells are cultured in a medium where the carbon source is maintained at a level to provide for less than about 90%, 80%, 75%, 60%, 50%, 40%, 30%, 25%, 20%, 10%, 5%, 1%, or less, of the maximum specific growth rate. Any carbon-containing sources that are digestible by the microorganism can be used. Non-limiting examples include carbohydrates such as monosaccharides, oligosaccharides and polysaccharides, organic acids such as acetic acid, propionic acid; and alcohols such as ethanol and propanol, and polyols such as glycerol.

In some embodiments, the carbon sources comprise primarily monosaccharides or oligosaccharides. In other embodiments, the carbon source consists essentially of monosaccharides and disaccharides. In still other embodiments, the carbon source is essentially free of cellulose.

Monosaccharides are the simple sugars that serve as building blocks for carbohydrates. They are classified based on their backbone of carbon (C) atoms: trioses have three carbon atoms, tetroses four, pentoses five, hexoses six, and heptoses seven. The carbon atoms are bonded to hydrogen atoms (—H), hydroxyl groups (—OH), and carbonyl groups (—C═O), whose combinations, order, and configurations allow a large number of stereoisomers to exist. Pentoses include xylose, found in woody materials; arabinose, found in gums from conifers; ribose, a component of RNA and several vitamins, and deoxyribose, a component of DNA. Exemplary hexoses include glucose, galactose, and fructose. Monosaccharides combine with each other and other groups to form a variety of disaccharides, and oligosaccharides. An oligosaccharide is a saccharide polymer containing a small number (typically three to ten) of simple sugars. They are generally found either O- or N-linked to compatible amino acid side chains in proteins or lipid moieties. A preferred oligosaccharide for use in the present fermentation reaction is disaccharide, including for example, sucrose, or trisaccharide such as raffinose.

Where it is desired to have cellulose, glycan, starch, or other polysaccharides as the ultimate carbon source, these polysaccharides can be first converted into monosaccharides and oligosaccharides by chemical means or by enzymatic methods. For instance, cellulose can be converted into glucose by the enzyme cellulase. Accordingly, if polysaccharides such as cellulose found in the biomass (including e.g., canola, alfalfa, rice, rye, sorghum, sunflower, wheat, soybean, tobacco, potato, peanut, cotton, sweet potato, cassava, coffee, coconut, citrus trees, cocoa, tea, fruits such as, banana, fig, pineapple, guava, mango, oats, barley, vegetables, ornamentals, or conifers) is used as the ultimate carbon source, it can be digested by cellulase to generate simpler sugars for use in conjunction with the fermentation procedure of the present invention. In certain embodiments, after the breakdown of the polysaccharide, the monosaccharide and/or oligosaccharide constitute at least about 50% by weight of the carbon source as determined at the beginning of the fermentation. In other embodiments, the monosaccharide and/or oligosaccharide constitute at least about 80% or even 90% by weight of the carbon source as determined at the beginning of the fermentation, such that the fermentation medium is essentially free of cellulose.

In other embodiments, the host cells are cultured in a fermentation medium comprises a nitrogen source present in an amount that is lower than that which would provide for a maximum specific growth rate. While not being bound by any particular theory, it is known that changing the levels of components such as nitrogen that are available to a cell can change the relative flux through the various chemical pathways within the cell. We have found that by restricting the level of nitrogen available to the microorganism, the amount of isoprenoid such as amorphadiene produced by the microorganism is increased. Exemplary levels of nitrogen of the present invention include in an amount that would support about 90%, 80%, 75%, 60%, 50%, 40%, 30%, 25%, 20%, 10%, 5%, 1%, or less, of the maximum specific growth rate.

The restriction of nitrogen can be implemented in stages. In some embodiments, nitrogen in the form of ammonia is provided in the beginning of the fermentation to support initial growth, but subsequent additions to the fermentation are free of nitrogen, or are free of nitrogen save for that level of ammonia needed to maintain the pH of the fermentation at 7 with an ammonia solution. For the bulk of the fermentation, the level of nitrogen is maintained at a level which is less than the amount which would support the maximum specific growth rate. The amounts can be for example amounts which would support at least about 90%, 80%, 75%, 60%, 50%, 40%, 30%, 25%, 20%, 10%, 5%, or 1%, or less, of the maximum specific growth rate. A fermentation of the present invention could have an initial nitrogen level above 10 mM as measured in the fermentation medium, to support an initial growth, and a subsequent a nitrogen level below 50 mM, 40 mM, 30 nM, 20 mM, 10 mM, or 4 mM in the fermentation medium.

Sources of assimilable nitrogen that can be used in a suitable fermentation reaction mixture include, but are not limited to, simple nitrogen sources, organic nitrogen sources, and complex nitrogen sources. Such nitrogen sources include anhydrous ammonia, ammonium salts of inorganic or organic acids such as ammonium chloride, ammonium sulfate, ammonium acetate, ammonium phosphate, other nitrogen-containing compounds and substances of animal, vegetable, and/or microbial origin. Amino acids can also be used as the nitrogen source, including leucine, isoleucine or valine, or a mixture thereof.

Any known method for providing a substrate to a fermentation reaction may be used to maintain the substrate level below the level which would provide for the maximum specific growth rate. Illustrative examples include the batch method where all the substrate for the fermentation is added in the beginning of the fermentation reaction; the continuous feed method; and the variable feed rate method, where, for instance, an increasing amount of substrate is provided as the fermentation proceeds in order to support the increased concentration of cells in the medium. Combinations of these three methods are often employed. For instance, it is common to have a certain amount of substrate present initially in the fermentation, to allow the microorganisms to deplete this initial amount of substrate, then to subsequently add substrate either continuously or to add it variably after the initial amount of substrate is utilized. It is an aspect of this invention to provide an initial amount of substrate to the cells in the fermentation medium, which may be present at a relatively high level, to allow the host cells to substantially use up the initial substrate, then to subsequently provide substrate to the host cells at a level that is suboptimal as compared to the amount that would support the maximum growth rate by either a continuous or variable feed rate. It will be appreciated by those of skill in the art that since the cells may be growing at an exponential rate, it can be advantageous to vary the feed rate at an exponential rate in order to keep the amount of substrate relative to the level of host cells constant. Thus in certain embodiments, substrates are added in an exponentially increasing manner, but yet at a level which is lower than the level which would provide the maximum specific growth rate.

In some embodiments, the fermentation reaction is given a reduced feed of carbon source relative to the carbon feed which would provide for the maximum specific growth rate. While not being bound by a particular theory, it is known that changing the levels of nutrients available to a cell will change the relative flux through the various chemical pathways within the cell. For example, some enzymes are inducible, and will only be active when certain nutrients are present. We have observed that lowering the carbon source feed rate to a microorganism can improve the amount of isoprenoid produced in the fermentation. In practice, the carbon source can be supplied initially in an amount sufficient to support an initial growth of the host cells until such initial carbon source is substantially depleted, after which the carbons source is added at an exponential rate, but at a rate which is below that which would support the maximum specific growth of the host cells. For example, in a method of the present invention, the carbon source is added in an amount that would support about 90%, 80%, 75%, 60%, 50%, 40%, 30%, 25%, 20%, 15%, 10%, or less, of the maximum specific growth rate.

In other embodiments, the fermentation reaction is given an initial bolus of carbon source sufficient to grow at or near the maximum specific growth rate (unlimited growth) followed by a reduced feed rate at a level below that required to support the maximum specific growth rate, for the remainder of the fermentation. In some cases, the point at which the reduced carbon source feed rate is implemented is the point at which a predetermined feed rate is achieved. In certain embodiments, the microorganism is provided with enough carbon source to grow exponentially to a feed rate of about 15 g/L/hr, after which the feed rate is reduced to 5.7 g/L/hr and held constant at that rate for the remainder of the fermentation.

In certain embodiments, one or more of the heterologous mevalonate or DXP pathway enzymes is inducible and induced after the carbon source feed rate has been reduced to a level below that required for maximum specific growth. For example, where the engineered microorganism has an inducible promoter, the fermentation is first run by adding carbon source to achieve a exponential growth, but at a level which is below that to support maximum specific growth, then the carbon source feed rate is reduced to an even lower level for the remainder of the fermentation, and the inducer added after the carbon source feed rate is reduced. In some embodiments, the microorganisms are induced with isopropylthio-beta-D-galactoside (IPTG) after the reduced carbon source feed is initiated.

In other embodiments, the fermentation reaction is performed in a manner that avoids the build up of toxic substances that decrease cell growth rates. For example, it is known that when too much glucose is added to the medium, toxic products such as acetate can build up in the organism. See, for example, Kortz et al. (1995) *J. Biotechnol* 39: 59-65. Thus by providing a high level of carbon source, at or approaching the amount which would support a maximum growth rate (unlimited growth), the initial growth of the cells may be higher, but the growth becomes arrested due to the accumulation of toxic substances. The level at which the carbon source is added below the level where the toxic products do not accumulate is referred to as the critical level or the inhibitory threshold. Thus in certain embodiments, the fermentation reaction is performed such that the carbon source is kept below the critical level for the build up of toxic substances. Those skilled in the art will appreciate that the critical concentration of substrates will vary with the strain and the medium which is used.

An effective fermentation reaction mixture can contain other compounds such as inorganic salts, vitamins, trace metals, or growth promoters. Such other compounds can also be present in carbon, nitrogen or mineral sources in the effective reaction mixture or can be added specifically to the reaction mixture. One embodiment of the invention involves providing these compounds at levels that are suboptimal as compared to that would support the maximum growth rate of the host cells in order to increase isoprenoid production.

The fermentation reaction mixture can also contain a suitable phosphate source. Such phosphate sources include both inorganic and organic phosphate sources. Non-limiting examples of phosphate sources include, but are not limited to, phosphate salts such as mono or dibasic sodium and potassium phosphates, ammonium phosphate, polyphosphate, and mixtures thereof. A suitable fermentation reaction mixture can also include a source of magnesium. In some embodiments, the magnesium is in the form of a physiologically acceptable salt, such as magnesium sulfate heptahydrate, although other magnesium sources in concentrations that contribute similar amounts of magnesium can be used. Further, in some instances it may be desirable to allow the fermentation reaction mixture to become depleted of a magnesium source during fermentation. In some embodiments, the phosphorous source is provided in an amount that is suboptimal as compared to that would support a maximum specific growth rate.

The fermentation reaction mixture can also include a biologically acceptable chelating agent, such as the dihydrate of trisodium citrate and ethylenediaminetetraacetic acid. The fermentation reaction mixture can also initially include a biologically acceptable acid or base to maintain the desired pH of the fermentation reaction mixture. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof.

The fermentation reaction mixture can also include a biologically acceptable calcium source, including, but not limited to, calcium chloride. The fermentation reaction mixture can also include sodium chloride. The fermentation reaction mixture can also include trace metals. Such trace metals can be added to the fermentation reaction mixture as a stock solution that, for convenience, can be prepared separately from the rest of the fermentation reaction mixture. A suitable trace metals solution can include, but is not limited to sodium selenate; ferrous sulfate; heptahydrate; cupric sulfate, pentahydrate; zinc sulfate, heptahydrate; sodium molybdate, dihydrate; cobaltous chloride; selenium or chromium solution; hexahydrate; and manganous sulfate monohydrate. Hydrochloric acid may be added to the stock solution to keep the trace metal salts in solution.

If a pathway intermediate or a compound that can be converted to a pathway intermediate is added to the fermentation medium, the intermediate or compound is typically present in an excess amount.

Fermentation can be conducted under anaerobic (deficient in oxygen) or aerobic (oxygenated) conditions. Under aerobic conditions, microorganisms can break down sugars to end products such as $CO_2$ and $H_2O$. Under anaerobic conditions, the host cells utilize an alternative pathway to produce $CO_2$ and ethanol. Fermentation can also be used to refer to the bulk growth of microorganisms on a growth medium where no distinction is made between aerobic and anaerobic metabolism. In general, aerobic fermentation is carried out for production of isoprenoids.

The fermentations of the present invention can be carried out in a batch, a fed-batch, or a continuous process. A batch process is typically a closed process where all of the raw materials are added at the beginning of the fermentation. A fed-batch process is typically a closed process where the carbon source and/or other substrates are added in increments throughout the process. A fed-batch process allows for greater control of the medium and the growth of the microorganisms. A continuous process can be considered an open system where medium is continuously added and product is simultaneously removed. Processes in between these types can also be used. For instance, in one embodiment, the fermentation is begun as a fed-batch process, and an organic layer, such as dodecane is placed in contact with the fermentation medium while the fermentation process continues. Isoprenoids, which typically have a higher solubility in the organic medium than in the aqueous fermentation medium are extracted out of the fermentation medium into the organic layer. Where the isoprenoids are produced in excess of the saturation point and form a layer separable from the medium, then simple separation by way of draining or sucking the distinct phase layer can be carried out. This process has characteristics of both a fed-batch process and a continuous process, because of the removal of product from the medium and the fermentation progresses. The fed-batch and continuous processes allow for the control of the addition of fermentation components during the fermentation process. A fed-batch, continuous, or combination of these processes is usually preferred in carrying out the invention. The processes allow for greater control of the rate of addition of feed and other fermentation components as a function of time. The removal of product during fermentation can be beneficial, especially where the accumulated product leads to inhibition of the production pathways.

The amount of microorganism per liter of fermentation, or the density of microorganism, can be measured by measuring the weight of microorganism isolated from a given volume of the fermentation medium. A common measure is the dry weight of cells per liter of fermentation medium. Another method which can be used to monitor the fermentation while it is progressing is by a measurement of the optical density of the medium. A common method is to measure the optical density at a wavelength of 600 nm, referred to the $OD_{600}$, or the OD. The OD can be correlated to a the density of a specific type of organism within a specific medium, but the specific relationship between OD and amount of microorganism per volume will not generally be applicable across all types of organisms in all types of media. A calibration curve can be created by measuring the OD and the dry cell weight over a range of cell densities. In some cases, these correlations can be used in different fermentation of the same or similar microorganisms in the same or similar media.

In another aspect, the present invention provides a method comprising the steps of (i) performing a fermentation reaction comprising a fermentation medium and a plurality of genetically modified host cells that produce the isoprenoid under conditions such that (a) the fermentation medium is kept at a temperature lower than that which would provide for a maximum specific growth rate of said host cells; (b) the fermentation medium comprises a carbon source present in an amount that is lower than that which would provide for a maximum specific growth rate of the host cells; and/or (c) the fermentation medium comprises a nitrogen source present in an amount that is lower than that which would provide for a maximum specific growth rate of the host cells; (ii) recovering the isoprenoid produced under one or more conditions set forth in (a) through (c). In one embodiment, the fermentation reaction is run under condition (a). In another embodiment, the fermentation reaction is run under conditions (a) and (b). In yet another embodiment, the fermentation reaction is run under conditions of (a), (b), and (c), or in any other combinations thereof.

Using the methods described herein, the host cells produce more than about 10 grams of isoprenoid per liter of fermentation reaction mixture (10 g/L). In other embodiments, more than about 15 g/L, more than about 20 g/L, more than 25 g/L is produced, or more than about 30 g/L of isoprenoid is produced.

In another embodiment, the host cells produce more than about 50 milligrams of isoprenoid per gram of dry host cells (50 milligrams per gram dry cell weight) is produced. In other embodiments, more than about 100 milligrams per gram dry cell weight, more than about 150 milligrams per gram dry cell weight, more than about 200 milligrams per gram dry cell weight, more than about 250 milligrams per gram dry cell weight, more than about 500 milligrams per gram dry cell weight, more than about 750 milligrams per gram dry cell weight, or more than about 1000 milligrams per gram dry cell weight of isoprenoid is produced.

In other embodiments, the production level, whether it is in grams per liter or milligrams per gram dry cell weight is achieved in less than about 150 hours, preferably less than about 96 hours, or even less than about 72 hours.

Non-limiting examples of suitable isoprenoids include: hemiterpenes (derived from 1 isoprene unit) such as isoprene; monoterpenes (derived from 2 isoprene units) such as myrcene; sesquiterpenes (derived from 3 isoprene units) such as amorpha-4,11-diene; diterpenes (derived from four isoprene units) such as taxadiene; triterpenes (derived from 6 isoprene units) squalene; tetraterpenes (derived from 8 isoprenoids) β-carotene; and polyterpenes (derived from more than 8 isoprene units) such as polyisoprene. In some embodiments, the isoprenoid is not a carotenoid. In other embodiments, the isoprenoid is a $C_5$-$C_{20}$ isoprenoid.

Although the invention has been described in conjunction with specific embodiments thereof, the foregoing description is intended to illustrate and not limit the scope of the invention. Other aspects, advantages, and modifications within the scope of the invention will be apparent to those skilled in the art to which the invention pertains.

EXAMPLES

The practice of the present invention can employ, unless otherwise indicated, conventional techniques of the biosynthetic industry and the like, which are within the skill of the art. To the extent such techniques are not described fully herein, one can find ample reference to them in the scientific literature.

In the following examples, efforts have been made to ensure accuracy with respect to numbers used (for example, amounts, temperature, and so on), but variation and deviation can be accommodated, and in the event a clerical error in the numbers reported herein exists, one of ordinary skill in the

Example 1

This example describes methods for making expression plasmids that encode for enzymes including enzymes of the MEV pathway from *Saccharomyces cerevisiae* organized in operons.

Expression plasmid pMevT was generated by inserting the MevT operon (SEQ ID NO: 1) into the pBAD33 vector. The MevT operon encodes the set of MEV pathway enzymes that together transform the ubiquitous precursor acetyl-CoA to (R)-mevalonate, namely acetoacetyl-CoA thiolase, HMG-CoA synthase, and HMG-CoA reductase. The MevT operon was generated by PCR amplifying from *Escherichia coli* genomic DNA the coding sequence of the atoB gene (GenBank accession number NC_000913 REGION: 2324131 . . . 2325315) (encodes an acetoacetyl-CoA thiolase), from *Saccharomyces cerevisiae* genomic DNA the coding sequence of the ERG13 gene (GenBank accession number X96617, REGION: 220 . . . 1695) (encodes a HMG-CoA synthase), and from *Saccharomyces cerevisiae* genomic DNA a segment of the coding region of the HMG1 gene (GenBank accession number M22002, REGION: 1660 . . . 3165) (encodes a truncated HMG-CoA reductase (tHMGR)). The upstream PCR primer used for the amplification of the HMG1 gene fragment included an artificial start codon. The amplified fragments were spliced together using overlap extensions (SOEing), during which process ribosome binding sites were introduced after the atoB and the ERG13 coding sequences. After the addition of 3' A overhangs, the MevT operon was ligated into the TA cloning vector pCR4 (Invitrogen, Carlsbad, Calif.), and sequenced to ensure accuracy. The MevT operon was subsequently ligated into the XmaI PstI restriction enzyme site of vector pBAD33 (Guzman et al. (1995) *J. Bacteriol.* 177(14): 4121-4130). To place the operon under the control of the $P_{Lac}$ promoter, the araC-$P_{BAD}$NsiI-XmaI fragment of pBAD33 was replaced with the NsiI-XmaI fragment of pBBR1MCS, yielding expression plasmid pMevT (see U.S. Pat. No. 7,192,751).

Expression plasmid pAM36-MevT66 was generated by inserting the MevT66 operon into the pAM36 vector. Vector pAM36 was generated by inserting an oligonucleotide cassette containing AscI-SfiI-AsiSI-XhoI-PacI-FsII-PmeI restriction enzyme sites into the pACYC184 vector (GenBank accession number XO6403), and by removing the tet resistance gene in pACYC184. The MevT66 operon was synthetically generated using the nucleotide sequence SEQ ID NO: 1 as a template, which comprises the atoB gene from *Escherichia coli* (GenBank accession number NC_000913 REGION: 2324131 . . . 2325315), the ERG13 gene from *Saccharomyces cerevisiae* (GenBank accession number X96617, REGION: 220 . . . 1695), and a truncated version of the HMG1 gene from *Saccharomyces cerevisiae* (GenBank accession number M22002, REGION: 1777 . . . 3285), all three sequences being codon-optimized for expression in *Escherichia coli*. The synthetically generated MevT66 operon was flanked by a 5' EcoRI restriction enzyme site and a 3' Hind III restriction enzyme site, and could thus be cloned into compatible restriction enzyme sites of a cloning vector such as a standard pUC or pACYC origin vector. From this construct, the MevT66 operon was PCR amplified with flanking SfiI and AsiSI restriction enzyme sites, the amplified DNA fragment was digested to completion using SfiI and AsiSI restriction enzymes, the reaction mixture was resolved by gel electrophoresis, the approximately 4.2 kb DNA fragment was gel extracted using a Qiagen gel purification kit (Valencia, Calif.), and the isolated DNA fragment was ligated into the SfiI AsiSI restriction enzyme site of the pAM36 vector, yielding expression plasmid pAM36-MevT66.

Expression plasmid pAM25 was generated by inserting the MevT66 operon into the pAM29 vector. Vector pAM29 was created by assembling the p15A origin of replication and kan resistance gene from pZS24-MCS1 (Lutz and Bujard (1997) *Nucl Acids Res.* 25:1203-1210) with an oligonucleotide-generated lacUV5 promoter. The DNA synthesis construct comprising the MevT66 operon (see above) was digested to completion using EcoRI and Hind III restriction enzymes, the reaction mixture was resolved by gel electrophoresis, the 4.2 kb DNA fragment was gel extracted, and the isolated DNA fragment was ligated into the EcoRI HindIII restriction enzyme site of pAM29, yielding expression plasmid pAM25.

Expression plasmid pMevB-Cm was generated by inserting the MevB operon into the pBBR1MCS-1 vector. The MevB operon encodes the set of enzymes that together convert (R)-mevalonate to IPP, namely mevalonate kinase, phosphomevalonate kinase, and mevalonate pyrophosphate carboxylase. The MevB operon was generated by PCR amplifying from *Saccharomyces cerevisiae* genomic DNA the coding sequences of the ERG12 gene (GenBank accession number X55875, REGION: 580 . . . 1911) (encodes a mevalonate kinase), the ERG8 gene (GenBank accession number Z49939, REGION: 3363 . . . 4718) (encodes a phosphomevalonate kinase), and the MVD1 gene (GenBank accession number X97557, REGION: 544 . . . 1734) (encodes a mevalonate pyrophosphate carboxylase), and by splicing the PCR fragments together using overlap extensions (SOEing). By choosing appropriate primer sequences, the stop codons of ERG12 and ERG8 were changed from TAA to TAG during amplification to introduce ribosome binding sites. After the addition of 3' A overhangs, the MevB operon was ligated into the TA cloning vector pCR4 (Invitrogen, Carlsbad, Calif.). The MevB operon was excised by digesting the cloning construct to completion using PstI restriction enzyme, resolving the reaction mixture by gel electrophoresis, gel extracting the 4.2 kb DNA fragment, and ligating the isolated DNA fragment into the PstI restriction enzyme site of vector pBBR1MCS-1 (Kovach et al., *Gene* 166(1): 175-176 (1995)), yielding expression plasmid pMevB-Cm.

Expression plasmid pMBI was generated by inserting the MBI operon into the pBBR1MCS-3 vector. The MBI operon encodes the same enzymes as the MevB operon, as well as an isopentenyl pyrophosphatase isomerase that catalyzes the conversion of IPP to DMAPP. The MBI operon was generated by PCR amplifying from *Escherichia coli* genomic DNA the coding sequence of the idi gene (GenBank accession number AF119715) using primers that contained an XmaI restriction enzyme site at their 5' ends, digesting the amplified DNA fragment to completion using XmaI restriction enzyme, resolving the reaction mixture by gel electrophoresis, gel extracting the 0.5 kb fragment, and ligating the isolated DNA fragment into the XmaI restriction enzyme site of expression plasmid pMevB-Cm, thereby placing idi at the 3' end of the MevB operon. The MBI operon was subcloned into the SalI and SacI restriction enzyme sites of vector pBBR1MCS-3 (Kovach et al., *Gene* 166(1): 175-176 (1995)), yielding expression plasmid pMBI (see U.S. Pat. No. 7,192,751).

Expression plasmid pMBIS was generated by inserting the ispA gene into pMBI. The ispA gene encodes a farnesyl pyrophosphate synthase that catalyzes the condensation of two molecules of IPP with one molecule of DMAPP to make farnesyl pyrophosphate (FPP). The coding sequence of the ispA gene (GenBank accession number D00694, REGION: 484 . . . 1383) was PCR amplified from *Escherichia coli* genomic DNA using a forward primer with a SacII restriction enzyme site and a reverse primer with a SacI restriction enzyme site. The amplified PCR product was digested to completion with SacII and SacI restriction enzymes, the reaction mixture was resolved by gel electrophoresis, and the 0.9 kb DNA fragment was gel extracted. The isolated DNA fragment was ligated into the SacII SacI restriction enzyme site of pMBI, thereby placing the ispA gene 3' of idi and the MevB operon, and yielding expression plasmid pMBIS (see U.S. Pat. No. 7,192,751).

Figure 3:
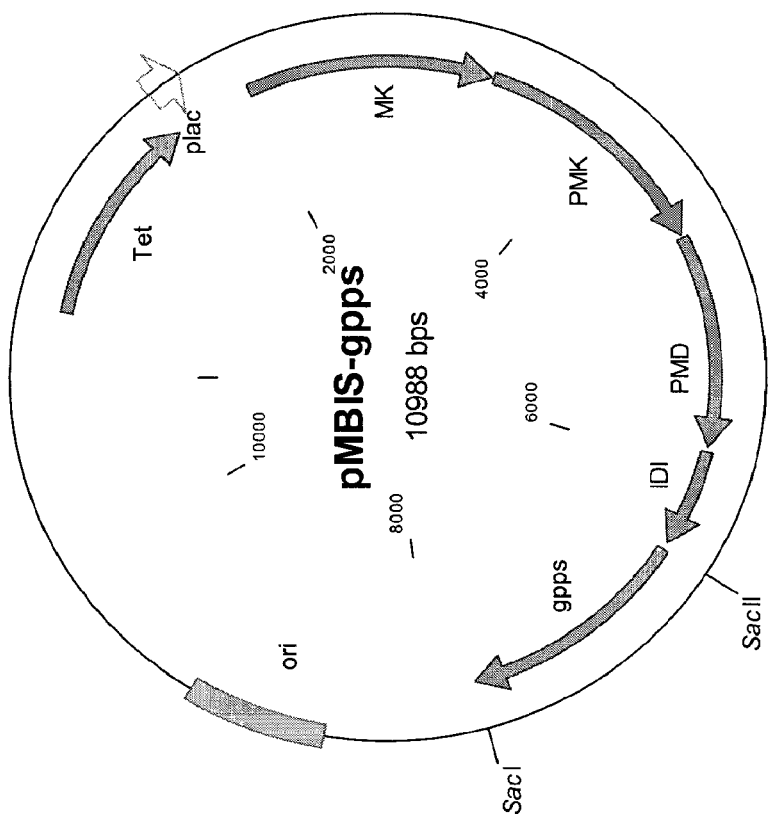
FIG. 3 shows a map of expression plasmid pMBIS-gpps.

Expression plasmid pMBIS-gpps was derived from expression plasmid pMBIS by replacing the ispA coding sequence with a nucleotide sequence encoding a geranyl diphosphate synthase ("gpps"). A DNA fragment comprising a nucleotide sequence encoding the geranyl diphosphate synthase was generated synthetically using the coding sequence of the gpps gene of *Arabidopsis thaliana* (GenBank accession number Y17376, REGION: 52 . . . 1320), codon-optimized for expression in *Escherichia coli*, as a template. The nucleotide sequence was flanked by a leader SacII restriction enzyme site and a terminal SacI restriction enzyme site, and can be cloned into compatible restriction enzyme sites of a cloning vector such as a standard pUC or pACYC origin vector. The synthetically generated geranyl diphosphate synthase sequence was isolated by digesting the DNA synthesis construct to completion using SacII and SacI restriction enzymes, resolving the reaction mixture by gel electrophoresis, gel extracting the approximately 1.3 kb DNA fragment, and ligating the isolated DNA fragment into the SacII SacI restriction enzyme site of expression plasmid pMBIS, yielding expression plasmid pMBIS-gpps (see FIG. 3 for a plasmid map).

Expression plasmid pAM45 was generated by inserting the MBIS operon into pAM36-MevT66 and adding lacUV5 promoters in front of the two operons. The MBIS operon was PCR amplified from pMBIS using primers comprising a 5' XhoI restriction enzyme site and a 3' PacI restriction enzyme site. The amplified PCR product was digested to completion using XhoI and PacI restriction enzymes, the reaction mixture was resolved by gel electrophoresis, the 5.4 kb DNA fragment was gel extracted, and the isolated DNA fragment was ligated into the XhoI PacI restriction enzyme site of pAM36-MevT66, yielding plasmid pAM43. A DNA fragment comprising a nucleotide sequence encoding the lacUV5 promoter was synthesized from oligonucleotides and sub-cloned into the AscI SfiI and AsiSI XhoI restriction enzyme sites of pAM43, yielding expression plasmid pAM45.

Example 2

This example describes methods for making expression vectors encoding enzymes including enzymes of the MEV pathway from *Staphylococcus aureus* organized in operons.

Expression plasmid pAM41 was derived from expression plasmid pAM25 by replacing the coding sequence of the HMG1 gene, which encodes the *Saccharomyces cerevisiae* HMG-CoA reductase, with the coding sequence of the mvaA gene, which encodes the *Staphylococcus aureus* HMG-CoA reductase (GenBank accession number BA000017, REGION: 2688925 . . . 2687648). The coding sequence of the mvaA gene was PCR amplified from *Staphylococcus aureus* subsp. *aureus* (ATCC 70069) genomic DNA using primers 4-49 mvaA SpeI (SEQ ID NO: 2) and 4-49 mvaAR XbaI (SEQ ID NO: 3), the amplified DNA fragment was digested to completion using SpeI restriction enzyme, the reaction mixture was resolved by gel electrophoresis, and the approximately 1.3 kb DNA fragment was gel extracted. The HMG1 coding sequence was removed from pAM25 by digesting the plasmid to completion using HindIII restriction enzyme. The terminal overhangs of the resulting linear DNA fragment were blunted using T4 DNA polymerase. The DNA fragment was then partially digested using SpeI restriction enzyme, the reaction mixture was resolved by gel electrophoresis, and the 4.8 kb DNA fragment was gel extracted. The isolated DNA fragment was ligated with the SpeI-digested mvaA PCR product, yielding expression plasmid pAM41. The nucleotide sequence of the atoB(opt):ERG13(opt):mvaA operon contained in pAM41 is SEQ ID NO: 41.

Expression plasmid pAM52 was derived from expression plasmid pAM41 by replacing the coding sequence of the ERG13 gene, which encodes the *Saccharomyces cerevisiae* HMG-CoA synthase, with the coding sequence of the mvaS gene, which encodes the *Staphylococcus aureus* HMG-CoA synthase (GenBank accession number BA000017, REGION: 2689180 . . . 2690346). ERG13 is also known as HMGS or HMG-CoA synthase. The coding sequence of the mvaS gene was PCR amplified from *Staphylococcus aureus* subsp. *aureus* (ATCC 70069) genomic DNA using primers HMGS 5' Sa mvaS-S (SEQ ID NO: 4) and HMGS 3' Sa mvaS-AS (SEQ ID NO: 5), and the amplified DNA fragment was used as a PCR primer to replace the coding sequence of the HMG1 gene in pAM41 according to the method of Geiser et al. (*BioTechniques* 31:88-92 (2001)), yielding expression plasmid pAM52. The nucleotide sequence of the atoB(opt):mvaS:mvaA operon contained in pAM52 is SEQ ID NO: 42.

Expression plasmid pAM97 was derived from expression plasmid pAM45 by replacing the MevT66 operon with the (atoB(opt):mvaS:mvaA) operon of expression plasmid pAM52. Expression plasmid pAM45 was digested to completion using AsiSI and SfiI restriction enzymes, the reaction mixture was resolved by gel electrophoresis, and the 8.3 kb DNA fragment lacking the MevT66 operon was gel extracted. The (atoB(opt):mvaS:mvaA) operon of pAM52 was PCR amplified using primers 19-25 atoB SfiI-S (SEQ ID NO: 6) and 19-25 mvaA-AsiSI-AS (SEQ ID NO: 7), the PCR product was digested to completion using SfiI and AsiSI restriction enzymes, the reaction mixture was resolved by gel electrophoresis, the 3.7 kb DNA fragment was gel extracted, and the isolated DNA fragment was ligated into the AsiSI SfiI restriction enzyme site of expression plasmid pAM45, yielding expression plasmid pAM97.

Expression plasmid pAM97-MBI was derived from expression plasmid pAM97 and pAM45 by replacing the MBIS operon of pAM97 with the MBI operon of pAM45. The MBI operon was PCR amplified from pAM45 using primers 9-70C (SEQ ID NO: 8) and 26-39B (SEQ ID NO: 9), the reaction mixture was resolved by gel electrophoresis, the 4.5 kb DNA fragment was gel extracted, and the isolated DNA fragment was digested to completion using SacI and XhoI restriction enzymes. Expression plasmid pAM97 was digested to completion using SacI and XhoI restriction enzymes, the reaction mixture was resolved by gel electrophoresis, the 7.6 kb fragment was gel extracted, and the isolated DNA fragment was ligated with the MBI operon PCR product, yielding expression plasmid pAM97-MBI.

Expression plasmid pAM97-MevB was derived from expression plasmid pAM97 and pAM45 by replacing the MBIS operon of pAM97 with the MevB operon of pAM45. The MevB operon was PCR amplified from pAM45 using primers 9-70C (SEQ ID NO: 8) and 26-39A (SEQ ID NO: 10), the reaction mixture was resolved by gel electrophoresis, the 3.9 kb DNA fragment was gel extracted, and the isolated DNA fragment was digested to completion using SacI and XhoI restriction enzymes. Expression plasmid pAM97 was digested to completion using SacI and XhoI restriction enzymes, the reaction mixture was resolved by gel electrophoresis, the 7.6 kb fragment was gel extracted, and the isolated DNA fragment was ligated with the MevB operon PCR product, yielding expression plasmid pAM97-MevB.

Expression plasmid pAM128 was generated by inserting the (atoB(opt):mvaS:mvaA) and MBIS operons of expression plasmid pAM97 into a vector that comprises the RK2 plasmid replication, segregation, and maintenance system, which obviates the continuous need for antibiotic selection of host cell transformants. The RK2 plasmid was digested to completion using PstI restriction enzyme, the reaction mixture was resolved by gel electrophoresis, the approximately 6.3 kb DNA fragment containing the entire par locus was gel extracted, and the isolated DNA fragment was subcloned into the PstI restriction enzyme site of the mini RK2 replicon pRR10 (Roberts et al. (1990) *J Bacteriol.* 172(11): 6204-6216), yielding vector pAM132. Expression plasmid pAM97 was digested to completion using AscI and SacI restriction enzymes, the reaction mixture was resolved by gel electrophoresis, the approximately 9.4 kb DNA fragment was gel extracted, and the isolated DNA fragment was ligated into the MluI SacI restriction enzyme site of pAM132, yielding expression plasmid pAM128.

Example 3

This example describes methods for making expression vectors that encode enzymes including enzymes of the MEV pathway from *Enterococcus faecalis* organized in operons.

Plasmid pAM16 was generated by inserting the coding sequence of the mvaE gene of *Enterococcus faecalis* (GenBank accession number AF290092 REGION: 1479 . . . 3890) (encodes an acetyl-CoA acetyltransferase/HMG-CoA reductase (HMGR)) into the pBlueScripII-KS(+) vector. The coding sequence of the mvaE gene was PCR amplified from *Enterococcus faecalis* genomic DNA (ATCC 700802) using 5' phosphorylated primers 4-40 mvaEF BamHI (SEQ ID NO: 11) and 4-40 mvaERHindIII (SEQ ID NO: 12). (Note that primer 4-40 mvaEF BamHI changes the start codon of the mvaE gene from TTG to ATG in the amplified PCR product.) The resulting PCR product was ligated into the SmaI restriction enzyme site of pBlueScripII-KS(+) (Stratagene, La Jolla, Calif.), yielding expression plasmid pAM16.

Plasmid pAM18 was generated by inserting the coding sequence of the mvaS gene of *Enterococcus faecalis* (GenBank accession number AF290092 REGION: 142 . . . 1293) (encodes a HMG-CoA synthase (HMGS)) into the pBlueScripII-KS(+) vector. The coding sequence of the mvaS gene was PCR amplified from *Enterococcus faecalis* genomic DNA (ATCC 700802) using 5' phosphorylated primers 4-40 mvaSF BglII (SEQ ID NO: 13) and 4-39 mvaSR BamHI (SEQ ID NO: 14), and the PCR product was ligated into the SmaI restriction enzyme site of pBlueScripII-KS(+) (Stratagene, La Jolla, Calif.), yielding expression plasmid pAM18.

Expression plasmid pAM22 was generated by inserting the coding sequence of the mvaE gene of expression plasmid pAM16 into the pZE21-$P_{L-lacO1}$ vector. Vector pZE$^{21}$-$P_{L-lacO1}$ is a derivative of vector pZE21-MCS-1 in which the tet promoter was replaced with the $P_{L-lacO1}$ promoter (Lutz and Bujard (1997) *Nucl Acids Res.* 25:1203-1210). Expression plasmid pAM16 was digested to completion using BamHI and HindIII restriction enzymes, the reaction mixture was resolved by gel electrophoresis, the approximately 2.4 kb DNA fragment containing the mvaE coding sequence was gel extracted, and the isolated DNA fragment was inserted into the BamHI HindIII restriction enzyme site of pZE21-$P_{L-lacO1}$, yielding expression plasmid pAM22.

Expression plasmid pAM33 was generated by inserting the coding sequence of the mvaS gene of expression plasmid pAM18 into expression plasmid pAM22. Expression plasmid pAM18 was digested to completion using BglII and BamHI restriction enzymes, the reaction mixture was resolved by gel electrophoresis, the approximately 1.2 kb DNA fragment containing the coding sequence of the mvaS gene was gel extracted, and the isolated DNA fragment was inserted into the BamHI site of expression plasmid pAM22, yielding expression plasmid pAM33.

Expression plasmid pAM34 was generated by inserting the mvaS-mvaE operon of expression plasmid pAM33 into vector pAM29. The mvaS-mvaE operon was isolated by partially digesting pAM33 using EcoRI restriction enzyme, digesting the resulting linear DNA fragment using MluI restriction enzyme, resolving the reaction mixture by gel electrophoresis, and gel extracting the approximately 3.6 kb DNA fragment. The vector backbone of pAM29 was obtained by digesting to completion expression vector pAM25 using MluI and EcoRI restriction enzymes, resolving the reaction mixture by gel electrophoresis, and gel extracting the approximately 2.1 kb DNA fragment. The two isolated DNA fragments were ligated, yielding expression plasmid pAM34.

Example 4

This example describes methods for making expression plasmids that encode enzymes, including enzymes of the DXP pathway from *Escherichia coli* organized in operons.

Figure 4:
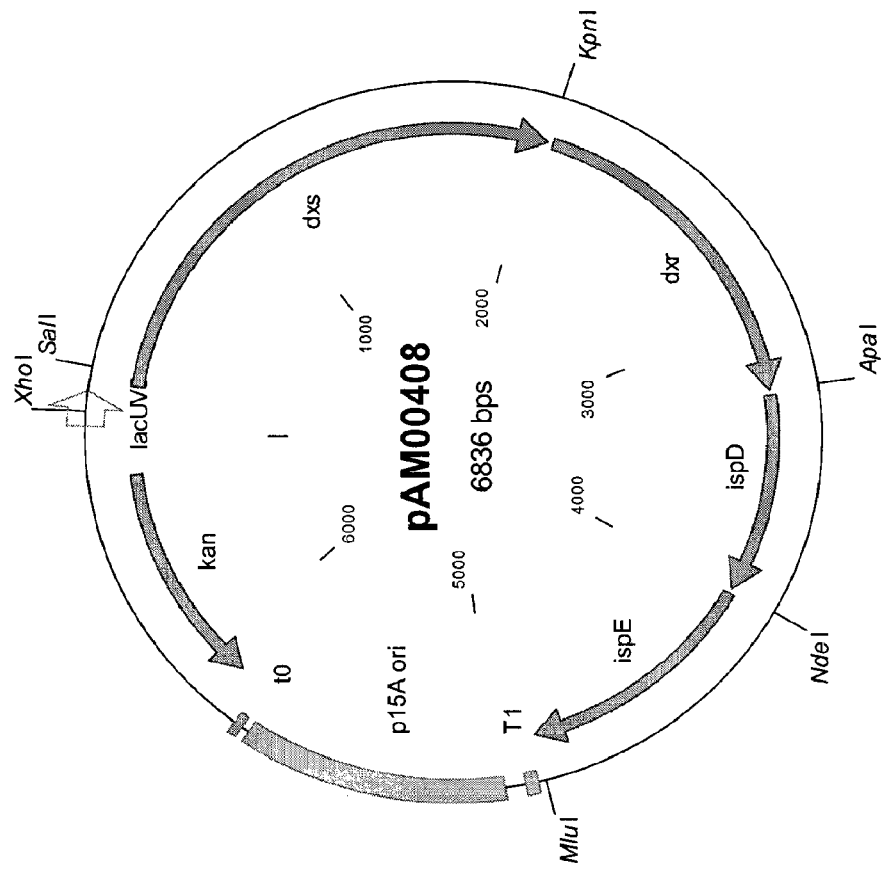
FIG. 4 shows a map of expression plasmid pAM408.

Expression plasmid pAM408 was generated by inserting genes encoding enzymes of the "top" DXP pathway into the pAM29 vector. Enzymes of the "top" DXP pathway include 1-deoxy-D-xylulose-5-phosphate synthase (encoded by the dxs gene of *Escherichia coli*), 1-deoxy-D-xylulose-5-phosphate reductoisomerase (encoded by the dxr gene of *Escherichia coli*), 4-diphosphocytidyl-2C-methyl-D-erythritol synthase (encoded by the ispD gene of *Escherichia coli*), and 4-diphosphocytidyl-2C-methyl-D-erythritol synthase (encoded by the ispE gene of *Escherichia coli*), which together transform pyruvate and D-glyceraldehyde-3-phosphate to 4-diphosphocytidyl-2C-methyl-D-erythritol-2-phosphate. DNA fragments comprising nucleotide sequences that encode enzymes of the "top" DXP pathway were generated by PCR amplifying the coding sequences of the dxs (GenBank accession number U00096 REGION: 437539 . . . 439401), dxr (GenBank accession number U00096 REGION: 193521 . . . 194717), ispD (GenBank accession number U00096 REGION: 2869803 . . . 2870512), and ispE (GenBank accession number U00096 REGION 1261249 . . . 12621100) genes from *Escherichia coli* strain DH1 (ATCC #33849) with added optimal Shine Dalgarno sequences and 5' and 3' restriction enzyme sites using the PCR primers shown in SEQ ID NOS: 15-18. The PCR products were resolved by gel electrophoresis, gel extracted using a Qiagen (Valencia, Calif.) gel purification kit, digested to completion using appropriate restriction enzymes (XhoI and KpnI for the PCR product comprising the dxs gene; KpnI and ApaI for the PCR product comprising the dxr gene; ApaI and NdeI for the PCR product comprising the ispD gene; NdeI and MluI for the PCR product comprising the ispE gene), and purified using a Qiagen (Valencia, Calif.) PCR purification kit. Roughly equimolar amounts of each PCR product were then added to a ligation reaction to assemble the individual genes into an operon. From this ligation reaction, 1 µl of reaction mixture was used to PCR amplify 2 separate gene cassettes, namely the dxs-dxr and the ispD-ispE gene cassettes. The dxs-dxr gene cassette was PCR amplified using primers 67-1A-C (SEQ ID NO: 15) and 67-1D-C (SEQ ID NO: 18), and the ispD-ispE gene cassette was PCR amplified using primers 67-1E-C (SEQ ID NO: 19) and 67-1H-C (SEQ ID NO: 22). The two PCR products were resolved by gel electrophoresis, and gel extracted. The PCR product comprising the dxs-dxr gene cassette was digested to completion using XhoI and ApaI restriction enzymes, and the PCR product comprising the ispD-ispE gene cassette was digested to completion using ApaI and MluI restriction enzymes, and the two PCR products were purified. Vector pAM29 was digested to completion using SalI and MluI restriction enzymes, and the two digested PCR products containing the "top" DXP pathway operon were ligated into the SalI MluI restriction enzyme site of the pAM29 vector, yielding expression plasmid pAM408 (see FIG. 4 for a plasmid map).

Expression plasmid pAM409 was generated by inserting genes encoding enzymes of the "bottom" DXP pathway into the pAM369 vector. Enzymes of the "bottom" DXP pathway include 2C-methyl-D-erythritol 2,4-cyclodiphosphate synthase (encoded by the ispF gene of *Escherichia coli*), 1-hydroxy-2-methyl-2-(E)-butenyl-4-diphosphate synthase (encoded by the ispG gene of *Escherichia coli*), and isopentenyl/dimethylallyl diphosphate synthase (encoded by the ispH gene of *Escherichia coli*), which together transform 4-diphosphocytidyl-2C-methyl-D-erythritol-2-phosphate to IPP and DMAPP. IPP is also converted to DMAPP through the activity of isopentyl diphosphate isomerase (encoded by the idi gene of *Escherichia coli*). DMAPP can be further converted to FPP through the activity of farnesyl diphosphate synthase (encoded by the ispA gene of *Escherichia coli*). An operon encoding enzymes of the "bottom" DXP pathway as well as an isopentyl diphosphate isomerase and a farnesyl diphosphate synthase was generated by PCR amplifying the ispF (GenBank accession number U00096 REGION: 2869323 . . . 2869802), ispG (GenBank accession number U00096 REGION: 2638708 . . . 2639826), ispH (GenBank accession number U00096 REGION: 26277 . . . 27227), idi (GenBank accession number AF119715), and ispA (GenBank accession number D00694 REGION: 484 . . . 1383) genes from *Escherichia coli* strain DH1 (ATCC #33849) with added optimal Shine Dalgarno sequences and 5' and 3' restriction enzyme sites using the appropriate PCR primers. The PCR products were resolved by gel electrophoresis, gel extracted, digested with the appropriate restriction enzymes (BamHI and ApaI for the PCR product comprising the ispF gene; KpnI and ApaI for the PCR product comprising the ispG gene; SalI and KpnI for the PCR product comprising the ispH gene; SalI and HindIII for the PCR product comprising the idi gene; HindIII and NcoI for the PCR product comprising the ispA gene), and purified. Roughly equimolar amounts of each PCR product were then added to a ligation reaction to assemble the individual genes into an operon. From this ligation reaction, 1 µl of reaction mixture was used to PCR amplify 2 separate gene cassettes, namely the ispF-ispG and the ispH-idi-ispA gene cassettes. The ispF-ispG gene cassette was PCR amplified using primers 67-2A-C (SEQ ID NO: 23) and 67-2D-C (SEQ ID NO: 26), and the ispH-idi-ispA gene cassette was PCR amplified using primers 67-2E-C (SEQ ID NO: 27) and 67-2J-C (SEQ ID NO: 32). The two PCR products were resolved by gel electrophoresis, and gel extracted. The PCR product comprising the ispF-ispG gene cassette was digested to completion using BamHI and KpnI restriction enzymes, and the PCR product comprising the ispH-idi-ispA gene cassette was digested to completion using KpnI and NcoI restriction enzymes, and the two PCR products were purified. Vector pAM369 was created by assembling the p15A origin of replication from pAM29 and beta-lactamase gene for ampicillin resistance from pZE12-luc (Lutz and Bujard (1997) *Nucl Acids Res.* 25:1203-1210) with an oligonucleotide-generated lacUV5 promoter. Vector pAM369 was digested to completion using BamHI and NcoI restriction enzymes, and the 2 isolated PCR products containing the "bottom" DXP pathway operon were ligated into the BamHI NcoI restriction enzyme site of the pAM369 vector, yielding expression plasmid pAM409.

Figure 5:
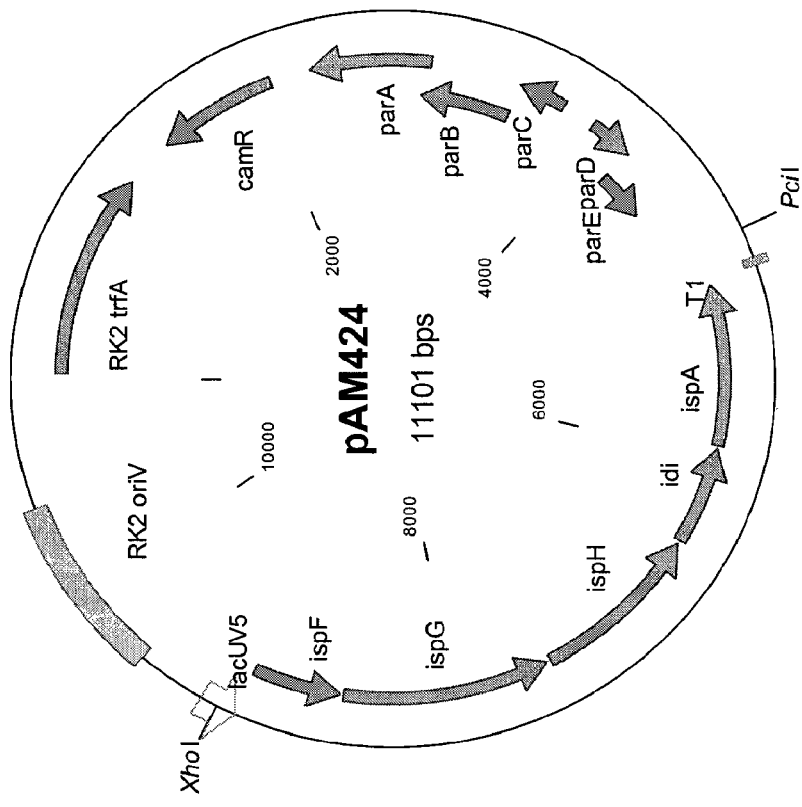
FIG. 5 shows a map of expression plasmid pAM424.

Expression plasmid pAM424, a derivative of expression plasmid pAM409 containing the broad-host range RK2 origin of replication, was generated by transferring the lacUV5 promoter and the ispFGH-idi-ispA operon of pAM409 to the pAM257 vector. Vector pAM257 was generated as follows: the RK2 par locus was PCR-amplified from RK2 plasmid DNA (Meyer et al. (1975) *Science* 190:1226-1228) using primers 9-156A (SEQ ID NO: 33) and 9-156B (SEQ ID NO: 34), the 2.6 kb PCR product was digested to completion using AatII and XhoI restriction enzymes, and the DNA fragment was ligated into a plasmid containing the p15 origin of replication and the chloramphenicol resistance gene from vector pZA31-luc (Lutz and Bujard (1997) *Nucl Acids Res.* 25:1203-1210), yielding plasmid pAM37-par; pAM37-par was digested to completion using restriction enzymes SacI and HindIII, the reaction mixture was resolved by gel electrophoresis, the DNA fragment comprising the RK2 par locus and the chloramphenicol resistance gene was gel extracted, and the isolated DNA fragment was ligated into the SacI HindIII site of the mini-RK2 replicon pRR10 (Roberts et al. (1990) *J Bacteriol.* 172:6204-6216), yielding vector pAM133; pAM133 was digested to completion using BglII and HindIII restriction enzymes, the reaction mixture was resolved by gel electrophoresis, the approximately 6.4 kb DNA fragment lacking the ampicillin resistance gene and oriT conjugative origin was gel extracted, and the isolated DNA fragment was ligated with a synthetically generated DNA fragment comprising a multiple cloning site that contained PciI and XhoI restriction enzyme sites, yielding vector pAM257. Expression plasmid pAM409 was digested to completion using XhoI and PciI restriction enzymes, the reaction mixture was resolved by gel electrophoresis, and the approximately 4.4 kb DNA fragment was gel extracted. Vector pAM257 was digested to completion using restriction enzymes XhoI and PciI, and the isolated DNA fragment containing the lacUV5 promoter and ispFGH-idi-ispA operon was ligated into the XhoI PciI restriction enzyme site of the pAM257 vector, yielding expression plasmid pAM424 (see FIG. 5 for a plasmid map).

Example 5

This example describes methods for making expression plasmids that encode enzymes that convert FPP or GPP.

Figure 6:
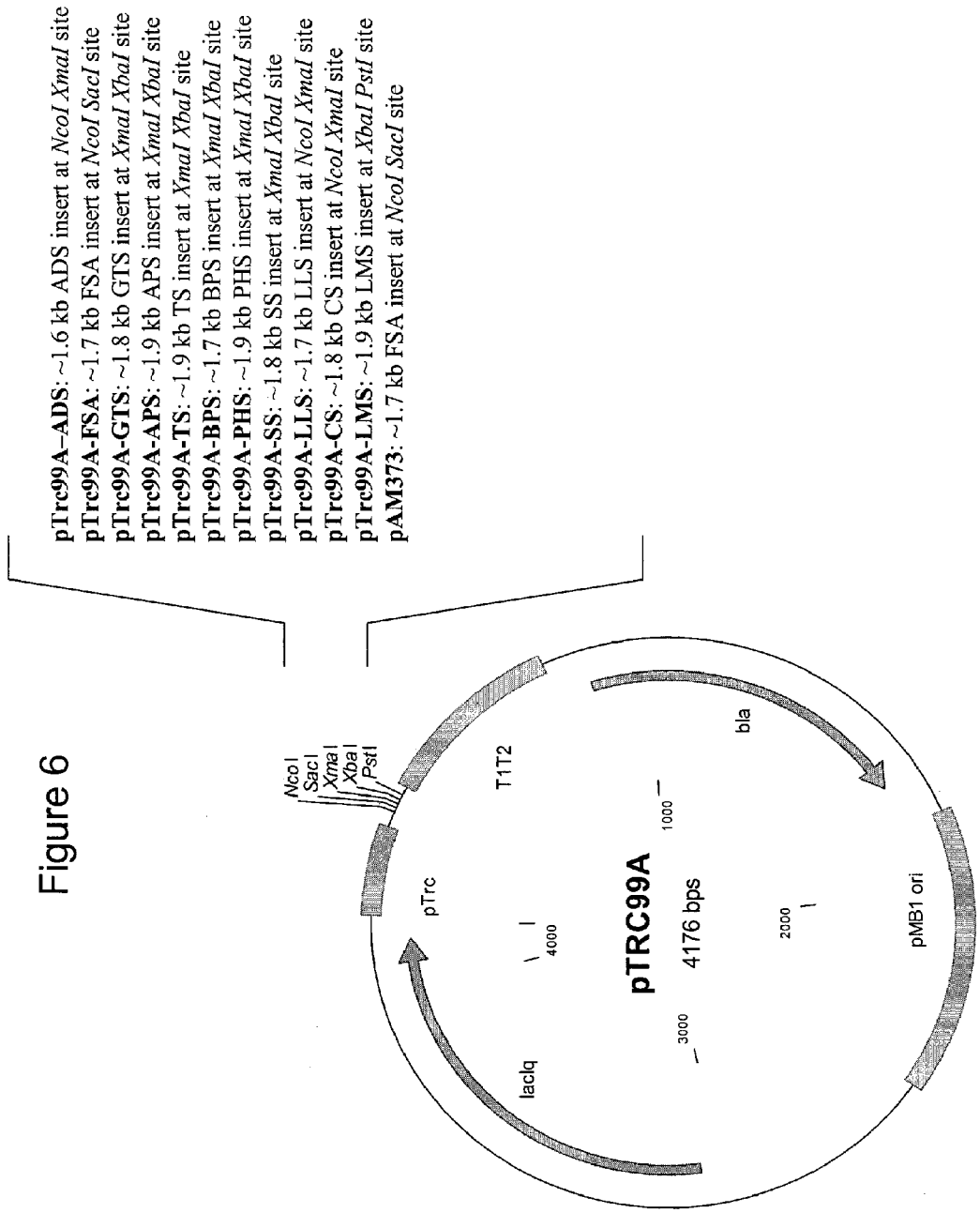
FIG. 6 shows a map of expression plasmids pTrc99A-ADS, pTrc99A-FSA, pTrc99A-LLS, pTrc99A-LMS, pTrc99A-GTS, pTrc99A-APS, pTrc99A-BPS, pTrc99A-PHS, pTrc99A-TS, pTrc99A-CS, pTrc99A-SS, and pAM373.

Expression plasmid pTrc99A-ADS was generated by inserting a nucleotide sequence encoding an amorpha-4,11-diene synthase ("ADS") into vector pTrc99A. The amorpha-4,11-diene synthase sequence was generated synthetically, so that upon translation the amino acid sequence would be identical to that described by Merke et al. (2000) *Ach. Biochem. Biophys.* 381:173-180, so that the nucleotide sequence encoding the amorpha-4,11-diene synthase was optimized for expression in *Escherichia coli*, and so that the nucleotide sequence was flanked by a 5' NcoI and a 3' XmaI restriction enzyme site (see U.S. Pat. No. 7,192,751). The nucleotide sequence was digested to completion using NcoI and XmaI restriction enzymes, the reaction mixture was resolved by gel electrophoresis, the approximately 1.6 kb DNA fragment was gel-extracted, and the isolated DNA fragment was inserted into the NcoI XmaI restriction enzyme site of the pTrc99A vector (Amman et al. (1985) *Gene* 40:183-190), yielding expression plasmid pTrc99A-ADS (see FIG. 6 for a plasmid map).

Expression plasmid pAM113 is a chloramphenicol-resistant derivative of pTrc99A-ADS. It was generated by PCR amplifying the chloramphenicol resistance gene from vector pZA31-luc (Lutz and Bujard (1997) *Nucl Acids Res.* 25:1203-1210) using 5'-phosphorylated primers 19-137 cml-pAM37-AS (SEQ ID NO: 35) and 19-137 cml-pAM37-S (SEQ ID NO: 36), and inserting the 920 bp PCR product into the FspI restriction enzyme site of expression plasmid pTrc99A-ADS, yielding expression plasmid pAM113.

Expression plasmid pC9 was generated by inserting a genomic DNA fragment of *Bacillus subtilis* 6051 comprising the coding sequence of the nudF gene and upstream genomic sequences (GenBank accession number Z99116 REGION: 49364 . . . 48548) into vector pTrc99A (Amann et al. (1988) *Gene* 69:301-315). Expression plasmid pNudF-H was generated by inserting the coding sequence of the *Bacillus subtilis* 6051 nudF gene (GenBank accession number Z99116 REGION: 49105 . . . 48548) into vector pTrc99A. Expression plasmid pyhfR was generated by inserting the coding sequence of the *Bacillus subtilis* 6051 yhjR gene (GenBank accession number Z99109 REGION: 97583 . . . 97002) into vector pTrc99A.

Expression plasmid pAM373 was generated by inserting a nucleotide sequence encoding the β-farnesene synthase ("FSB") of *Artemisia annua* (GenBank accession number AY835398), codon-optimized for expression in *Escherichia coli*, into the pTrc99A vector. The nucleotide sequence encoding the β-farnesene synthase was generated synthetically, and was amplified by PCR from its DNA synthesis construct using the appropriate primers. To create a leader NcoI restriction enzyme site in the PCR product comprising the β-farnesene synthase coding sequence, the codon encoding the second amino acid in the original polypeptide sequence (TCG coding for serine) was replaced by a codon encoding aspartic acid (GAC) in the 5' PCR primer (SEQ ID NO: 37). The resulting PCR product was partially digested using NcoI restriction enzyme, and digested to completion using SacI restriction enzyme, the reaction mixture was resolved by gel electrophoresis, the approximately 1.7 kb DNA fragment comprising the β-farnesene synthase coding sequence was gel extracted, and the isolated DNA fragment was ligated into the NcoI SacI restriction enzyme site of the pTrc99A vector, yielding expression plasmid pAM373 (see FIG. 6 for a plasmid map).

Expression plasmids pTrc99A-FSA, pTrc99A-GTS, pTrc99A-PS, pTrc99A-TS were generated by inserting a DNA fragment comprising a nucleotide sequence encoding an α-farnesene synthase ("FSA"), a γ-terpinene synthase ("GTS"), an α-pinene synthase ("APS"), or a terpinolene synthase ("TS") into the pTrc99A vector. The DNA fragment insert was generated synthetically, using as a template for example the coding sequence of the α-farnesene synthase gene of *Picea abies* (GenBank accession number AY473627, REGION: 24 . . . 1766), the coding sequence of the β-farnesene synthase gene of *Artemisia annua* (GenBank accession number AY835398), the coding sequence of the γ-terpinene synthase gene of *Citrus limon* (GenBank accession number AF514286 REGION: 30 . . . 1832), the coding sequence of the α-pinene synthase gene of *Abies grandis* (GenBank accession number U87909, REGION: 6 . . . 1892) or of *Pinus taeda* (GenBank accession number AF543530 REGION: 1 . . . 1887), or the coding sequence of the terpinolene synthase gene of *Ocimum basilicum* (GenBank accession number AY693650) or of *Pseudotsuga menziesii* (GenBank accession number AY906866 REGION: 10 . . . 1887) or of *Abies grandis* (GenBank accession number AF139206), all nucleotide sequences being codon-optimized for expression in *Escherichia coli*. The DNA fragments for FSA was amplified by PCR from its DNA synthesis construct using the primer sequences SEQ ID NO: 39 and SEQ ID NO: 40. The resulting PCR product was digested to completion using NcoI and SacI restriction enzymes, the reaction mixture was resolved by gel electrophoresis, the approximately 1.7 kb DNA fragment comprising the α-farnesene synthase coding sequence was gel extracted, and the isolated DNA fragment was ligated into the NcoI SacI restriction enzyme site of the pTrc99A vector, yielding expression plasmid pTrc99A-FSA (see FIG. 6 for a plasmid map). The DNA fragments for GTS, APS, and TS were designed to be flanked by a leader XmaI restriction enzyme site and a terminal XbaI restriction enzyme site, and were cloned into compatible restriction enzyme sites of a cloning vector such as a standard pUC or pACYC origin vector, from which they could be liberated again by digesting to completion the DNA synthesis construct using XbaI and XmaI restriction enzymes, resolving the reaction mixture by gel electrophoresis, and gel extracting the 1.7 to 1.9 terpene synthase encoding DNA fragment. The isolated DNA fragments were ligated into the XmaI XbaI restriction enzyme site of vector pTrc99A (Amman et al., *Gene* 40:183-190 (1985)), yielding plasmids pTrc99A-GTS, pTrc99A-APS, or pTrc99A-TS (see FIG. 6 for plasmid maps).

Expression plasmids pRS425-FSA and pRS425-FSB were generated by inserting a nucleotide sequence encoding an α-farnesene synthase ("FSA") or a β-farnesene synthase ("FSB"), respectively, into the pRS425-Gal1 vector (Mumberg et. al. (1994) *Nucl. Acids. Res.* 22(25): 5767-5768). The nucleotide sequence inserts were generated synthetically, using as a template for example the coding sequence of the α-farnesene synthase gene of *Picea abies* (GenBank accession number AY473627, REGION: 24 . . . 1766) or of the β-farnesene synthase gene of *Artemisia annua* (GenBank accession number AY835398), codon-optimized for expression in *Saccharomyces cerevisiae*. The synthetically generated nucleotide sequence was flanked by a 5' BamHI site and a 3' XhoI site, and could thus be cloned into compatible restriction enzyme sites of a cloning vector such as a standard pUC or pACYC origin vector. The synthetically generated nucleotide sequence was isolated by digesting to completion the DNA synthesis construct using BamHI and XhoI restriction enzymes. The reaction mixture was resolved by gel electrophoresis, the approximately 1.7 kb DNA fragment comprising the α-farnesene synthase or β-farnesene synthase coding sequence was gel extracted, and the isolated DNA fragment was ligated into the BamHI XhoI restriction enzyme site of the pRS425-Gal1 vector, yielding expression plasmid pRS425-FSA or pRS425-FSB, respectively.

Expression plasmids pTrc99A-LLS, pTrc99A-LMS, pTrc99A-BPS, pTrc99A-PHS, pTrc99A-CS, and pTrc99A-SS are generated by inserting a nucleotide sequence encoding a linalool synthase ("LLS"), limonene synthase ("LMS"), β-pinene synthase ("BPS"), β-phellandrene ("PHS"), carene synthase ("CS"), or sabinine synthase ("SS") into the pTrc99A vector. The nucleotide sequence inserts are generated synthetically, using as a template for example the coding sequence of the linalool synthase gene of *Artemisia annua* (GenBank accession number AF154124, REGION: 13 . . . 1764), the coding sequence of the limonene synthase gene of *Abies grandis* (GenBank accession number AF006193 REGION: 73 . . . 1986), the coding sequence of the β-pinene synthase of *Artemisia annua* (GenBank accession number AF276072 REGION: 1 . . . 1749), the coding sequence of the β-phellandrene synthase gene of *Abies grandis* (GenBank accession number AF139205 REGION: 34 . . . 1926), the coding sequence of the carene synthase gene of *Salvia stenophylla* (GenBank accession number AF527416 REGION: 78 . . . 1871), or the coding sequence of the sabinene synthase gene of *Salvia officinalis* (GenBank accession number AF051901 REGION: 26 . . . 1798). The nucleotide sequences encoding the β-pinene, sabinine, and β-phellandrene synthases are flanked by a leader XmaI restriction enzyme site and a terminal XbaI restriction enzyme site, the nucleotide sequences encoding the linalool and carene synthases are flanked by a leader NcoI restriction enzyme site and a terminal XmaI restriction enzyme site, and the nucleotide sequence encoding the limonene synthase is flanked by a leader NcoI restriction enzyme site and a terminal PstI restriction enzyme site. The DNA synthesis constructs are digested to completing using XmaI and XbaI (for the β-pinene, sabinine, and β-phellandrene synthase constructs), NcoI and XmaI restriction enzymes (for the linalool and careen synthase constructs), or XbaI and PstI restriction enzymes (for the limonene synthase construct). The reaction mixtures are resolved by gel electrophoresis, the approximately 1.7 to 1.9 kb DNA fragments are gel extracted, and the isolated DNA fragments are ligated into the XmaI XbaI restriction enzyme site (for the β-pinene, sabinine, and β-phellandrene synthase inserts), the NcoI XmaI restriction enzyme site (for the linalool and carene synthase inserts), or the XbaI PstI restriction enzyme site (for the limonene synthase insert) of the pTrc99A vector, yielding expression plasmids pTrc99A-LLS, pTrc99A-LMS, pTrc99A-BPS, pTrc99A-PHS, pTrc99A-CS, and pTrc99A-SS (see FIG. 6 for plasmid maps).

Example 6

This example describes the generation of *Escherichia coli* host strains useful in the invention.

As detailed in Table 1, the host strains were created by transforming chemically competent *Escherichia coli* parent cells with one or more expression plasmids of Example 1 through 5.

TABLE 1

*E. coli* host strains

| Host Strain | *E. coli* Parent Strain | Expression Plasmids | Antibiotic Selection |
|---|---|---|---|
| B32 | DH1 | pMevT | 100 ug/mL carbenicillin |
| B292 | B | pMBIS | 5 ug/mL tetracycline |
| B210 | DP | pTrc99A-ADS | 34 ug/mL chloramphenicol |
| B153 | DH1 | pAM97 | 100 ug/mL carbenicillin |
| B282 | DP | pTrc99A-ADS | 34 ug/mL chloramphenicol |
| B255 | DH1 | pAM128 | 100 ug/mL carbenicillin |
| B256 | DP | pAM113 | 34 ug/mL chloramphenicol |
| B86 | DH1 | pAM52 | 50 ug/mL kanamycin |
|  |  | pMBIS | 100 ug/mL carbenicillin |
|  |  | pTrc99A-ADS | 5 ug/mL tetracycline |
| B61 | DH1 | pAM25 |  |
|  |  | pBBR1MCS-3 |  |
|  |  | pTrc99A |  |
| B62 |  | pAM34 |  |
|  |  | pBBR1MCS-3 |  |
|  |  | pTrc99A |  |
| B003 | DH10B | pTrc99A-ADS | 100 µg/ml carbenicillin |
| B617 |  | pAM408 | 100 ug/mL carbenicillin |
|  |  | pTrc99A-ADS | 50 ug/mL kanamycin |
| B618 |  | pAM424 | 100 ug/mL carbenicillin |
|  |  | pTrc99A-ADS | 35 µg/ml chloramphenicol |
| B619 |  | pAM408 | 100 µg/ml carbenicillin |
|  |  | pAM424 | 50 µg/ml kanamycin |
|  |  | pTrc99A-ADS | 35 µg/ml chloramphenicol |
| B650 | DH10B | pAM373 | 100 µg/ml carbenicillin |
| B651 |  | pAM408 | 100 µg/ml carbenicillin |
|  |  | pAM373 | 50 µg/ml kanamycin |
| B652 |  | pAM424 | 100 µg/ml carbenicillin |
|  |  | pAM373 | 35 µg/ml chloramphenicol |
| B653 |  | pAM408 | 100 µg/ml carbenicillin |
|  |  | pAM424 | 50 µg/ml kanamycin |
|  |  | pAM373 | 35 µg/ml chloramphenicol |
| B286 | DH1 | pAM97-MevB | 100 ug/mL carbenicillin |
|  |  | pC9 | 34 ug/mL chloramphenicol. |
| B287 |  | pAM97-MevB |  |
|  |  | pnudF-H |  |
| B288 |  | pAM97-MevB |  |
|  |  | pyhfR |  |
| B291 |  | pAM97-MBI |  |
|  |  | pyhfR |  |

TABLE 1-continued

E. coli host strains

| Host Strain | E. coli Parent Strain | Expression Plasmids | Antibiotic Selection |
|---|---|---|---|
| B592 | DH1 | pMevT<br>pMBIS<br>pTrc99A-FSA | 100 ug/mL carbenicillin<br>34 ug/mL chloramphenicol |
| B552 | | pMevT<br>pMBIS<br>pAM373 | 5 ug/mL tetracycline |
| Example 21 host cell (production of GTS, APS, TS) | | pMevT<br>pMBIS-gpps<br>pTrc99A-GTS or -APS or -TS | |
| Example 21 host cell (production of LLS, LMS, BPS, PHS, CS, SS) | | pMevT<br>pMBIS-gpps<br>pTrc99A-LLS or -LMS or -BPS or -PHS or -CS or -SS | 100 ug/mL carbenicillin<br>34 ug/mL chloramphenicol<br>5 ug/mL tetracycline |

Host cell transformants were selected on Luria Bertoni (LB) agar containing antibiotics as detailed in Table 1. Single colonies were transferred from LB agar to culture tubes containing 5 mL of LB liquid medium and antibiotics. B003, B617, B618, B619, B650, B651, B652, and B653 host cell transformants were incubated at 30° C. on a rotary shaker at 250 rpm for 30 hours. All other host cell transformants were incubated at 37° C. on a rotary shaker at 250 rpm until growth reached stationary phase. The cells were adapted to minimal media by passaging them through 4 to 5 successive rounds of M9-MOPS media containing 0.8% glucose and antibiotics (see Table 2 for the composition of the M9-MOPS medium). The cells were stored at −80° C. in cryo-vials in 1 mL stock aliquots made up of 400 uL sterile 50% glycerol and 600 uL liquid culture.

TABLE 2

Composition of M9-MOPS Culture Medium

| Component | Quantity (per L) |
|---|---|
| Na2HPO47H2O | 12.8 g |
| KH2PO4 | 3 g |
| NaCl | 0.5 g |
| NH4Cl | 1 g |
| MgSO4 | 2 mmol |
| CaCl2 | 0.1 mmol |
| Thiamine | 0.1 ug |
| MOPS buffer pH 7.4 | 100 mmol |
| (NH3)6Mo7O244H2O | 3.7 ug |
| H3BO4 | 25 ug |
| CoCl2 | 7.1 ug |
| CuSO4 | 2.4 ug |
| MnCl2 | 16 ug |
| ZnSO4 | 2.9 ug |
| FeSO4 | 0.28 mg |

Example 7

This example demonstrates expression plasmid stability in the absence of antibiotics in an *Escherichia coli* host strain that harbors an expression plasmid comprising the RK2 plasmid replication, segregation, and maintenance system.

A seed culture of host strain B255 was established by adding a stock aliquot of the strain to a 125 mL flask containing 40 mL M9-MOPS, 2% glucose, 0.5% yeast extract, and antibiotics as detailed in Table 1, and by growing the culture overnight.

The seed culture was used to inoculate at an initial $OD_{600}$ of approximately 0.05, two 250 mL flasks each containing 40 mL M9-MOPS medium, 2% glucose, and 0.5% yeast extract. Culture #1 also contained 100 ug/mL carbenicillin and 34 ug/1 mL chloramphenicol. Culture #2 did not receive any antibiotics. Both cultures were incubated at 37° C. on a rotary shaker at 250 rpm until they reached an $OD_{600}$ of approximately 0.2, at which point the production of amorpha-4,11-diene in the host cells was induced by adding 40 uL of 1M IPTG to the culture medium. At the time of induction, the cultures were overlain with 8 mL of an organic overlay to capture the amorpha-4,11-diene. Samples were taken periodically for a total of 72 hours. Production of amorpha-4,11-diene by the host strain in the 2 cultures was confirmed by GC/MS as described in Example 10.

To assess plasmid stability in the two cell cultures, a sample of each culture was removed at 72 hours and streaked onto a LB agar plate (no antibiotics). After overnight incubation at 37° C., 50 individual colonies derived from each culture were replica-plated onto a LB agar-plus-antibiotics (34 ug/mL chloramphenicol, 100 ug/mL carbenicillin) plate and a LB agar-minus-antibiotics (no antibiotic) plate. After another overnight incubation at 37° C., the LB agar-plus-antibiotics and the LB agar-minus-antibiotics plate were each found to contain approximately 50 colonies, indicating that plasmid retention both in the presence and in the absence of antibiotics in the culture medium had been approximately 100%.

Example 8

This example demonstrates increased specific activity and stability of the *Enterococcus faecalis* HMGR compared to the *Saccharomyces cerevisiae* tHMGR in an *Escherichia coli* host strain.

Seed cultures of host strains B61 and B62 were established by adding a stock aliquot of each strain to 125 mL flasks containing 20 mL M9-MOPS medium, 0.8% % glucose, and antibiotics as detailed in Table 5, and by growing the cultures to saturation. The seed cultures were diluted 1:100 into 140 mL of fresh medium in a 500 mL flask, and grown again to an $OD_{550}$ of approximately 0.1, at which point production of amorpha-4,11-diene was induced by adding 140 uL 1 M IPTG to each culture. At 4, 12, 20, 28, 36, and 49 hours post-induction, samples were removed from each culture, and cells were pelleted by centrifugation. The cell pellets were snap frozen on dry ice, and then stored at −80° C.

To conduct enzyme assays, cell pellets were thawed on ice, and then lysed using Bugbuster (Novagen, Madison, Wis.) containing protease inhibitor mix #3 (Calbiochem, San Diego, Calif.), benzonase (20 μL oer5 mL bugbuster; Novagen, Madison, Wis.), and lysozyme (30 ug/mL). Enzyme activity of the *Saccharomyces cerevisiae* tHMGR was assayed in 50 mM Tris HCl (pH7.5), 0.2 mM NADPH (Sigma, St. Louis, Mo.), and 0.3 mM DL-3-hydroxy-3-methylglutaryl coenzyme A (HMG-CoA) sodium salt (Sigma, St. Louis, Mo.). The assay was started by adding cell lysate, and the disappearance of NADPH was monitored by absorbance at 340 nM. To account for non-specific disappearance of NADPH, results obtained in a control assay lacking HMG-CoA were subtracted from results obtained in test samples. Enzyme activity of the *Enterococcus faecalis* HMGR was measured similarly except that the assay buffer contained 100 mM potassium phosphate buffer (pH6.5), 0.4 mM NADPH, 1.0 mM EDTA, and 100 mM KCl.

Protein assays were done by the method of Bradford ((1976) *Anal Biochem.* 72:248-254). Specific activities were calculated as Δnmol NADPH/min/mg protein.

Figure 8:
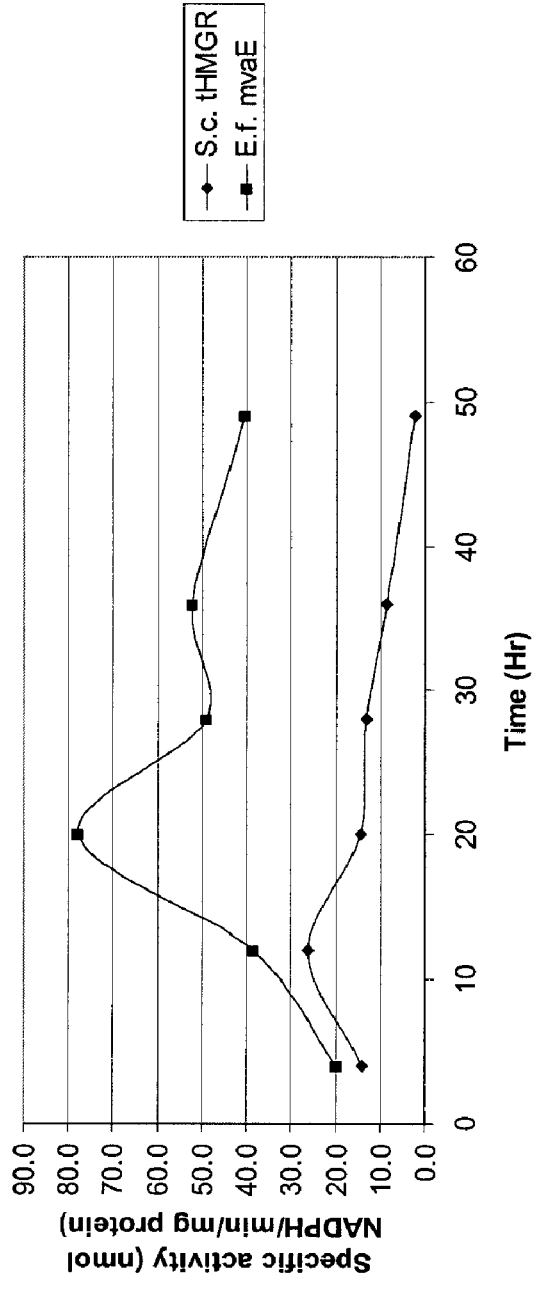
FIG. 8 shows the higher specific activity and increased stability of the *Enterococcus faecalis* HMGR-CoA reductase (HMGR) compared to the *Saccharomyces cerevisiae* truncated HMG-CoA reductase (tHMGR).

As shown in FIG. 8, the *Enterococcus faecalis* HMGR exhibited higher specific activity and increased stability compared to the *Saccharomyces cerevisiae* tHMGR.

Example 9

This example describes the calibration of $OD_{600}$ with dry cell weight ("DCW").

To obtain the relationship between DCW and OD600, a representative strain, B32, was grown in high cell density processes similar to those described in Examples 10-14. Samples were taken throughout the runs, and the $OD_{600}$ and DCW were measured for each sample. To determine the DCW, the cells were pelleted and the supernatant discarded. The cell pellet was washed once with water, and was then dried in an oven at 80° C. for at least 3 days. The tubes containing cell pellets were weighed, the weight of the tube was subtracted from the measured weights, and the remaining weight was divided by the initial volume of each sample (0.0015 L) to obtain the DCW.

Figure 9:
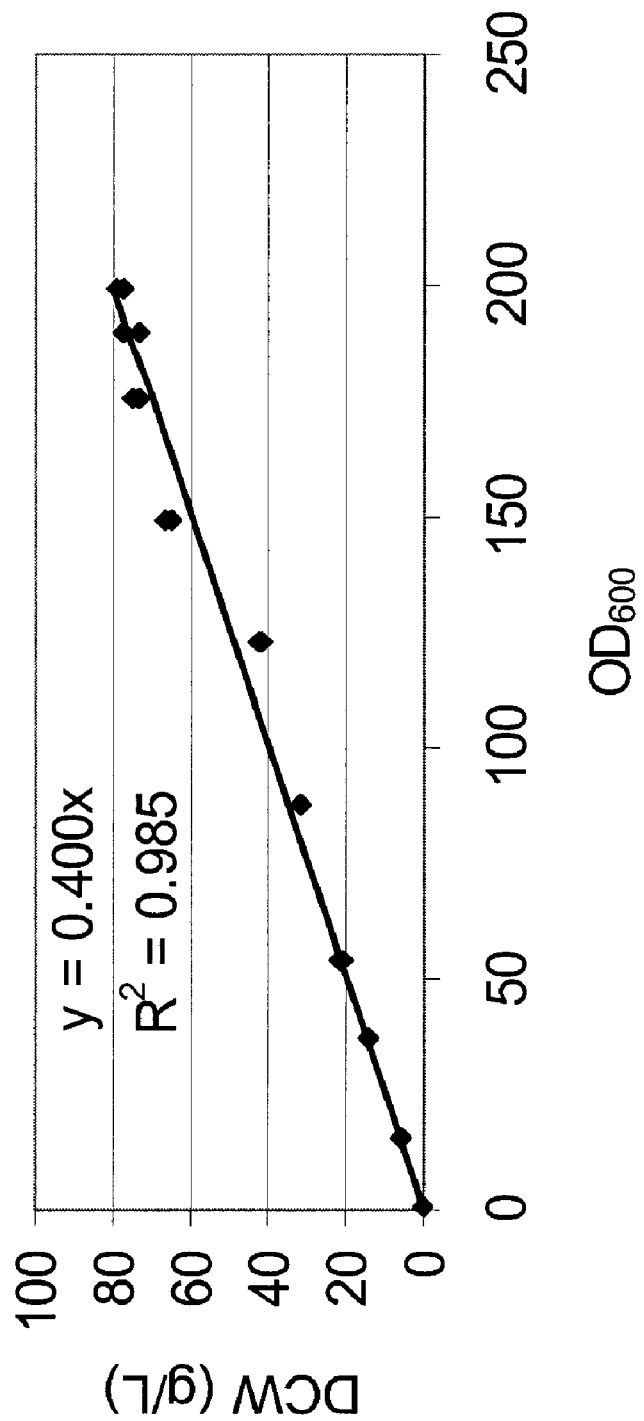
FIG. 9 shows the relationship between dry cell weight ("DCW") per liter and $OD_{600}$.

FIG. 9 shows the relationship between DCW and $OD_{600}$ measured in these experiments.

Example 10

This example demonstrates increased production of amorpha-4,11-diene in *Escherichia coli* host strains expressing the *Staphylococcus aureus* HMGR and HMGS compared to host strains expressing the *Saccharomyces cerevisiae* tHMGR and HMGS.

Seed cultures of host strains B32, B153, B210, B282, B292, B86, B255, and B256 were established by adding a stock aliquot of each strain to separate 125 mL flasks containing 25 mL M9-MOPS medium, 0.8% glucose, and antibiotics as detailed in Table 1, and by growing the cultures overnight.

The seed cultures were used to inoculate at an initial $OD_{600}$ of approximately 0.05 separate 250 mL flasks containing 40 mL M9-MOPS medium, 2% glucose, and antibiotics. The cultures were incubated at 30° C. on a rotary shaker at 250 rpm until they reached an $OD_{600}$ of approximately 0.2, at which point the production of amorpha-4,11-diene in the host cells was induced by adding 40 uL of 1M IPTG to the culture medium. The cultures were overlain with 8 mL of an organic overlay (e.g., dodecane, methyl oleate or isopropyl myristate). Samples of the organic overlay layer and the broth were taken once a day for 72 hours. Broth samples were used to measure the $OD_{600}$. Amorpha-4,11-diene concentration was measured by transferring 5 uL of the organic overlay layer to a clean glass vial containing 500 uL ethyl acetate spiked with beta- or trans-caryophyllene as an internal standard.

The organic overlay/ethyl acetate samples were analyzed on a Hewlett-Packard 6890 gas chromatograph/mass spectrometer (GC/MS) by scanning only for two ions, the molecular ion (204 m/z) and the 189 m/z ion, as described in Martin et al. (2001) *Biotechnol. Bioeng.* 75:497-503. To expedite run times, the temperature program and column matrix was modified to achieve optimal peak resolution and the shortest overall runtime. A 1 uL sample was separated on the GC using a DB-XLB column (available from Agilent Technologies, Inc., Palo Alto, Calif.) and helium carrier gas. The temperature program for the analysis was as follows: 100° C. for 0.75 minutes, increasing temperature at 60° C./minute to a temperature of 300° C., and a hold at 300° C. for 0.5 minutes. The resolved samples were analyzed by a Hewlett-Packard model 5973 mass-selective detector that monitored ions 189 and 204 m/z. Previous mass spectra demonstrated that the amorpha-4,11-diene synthase product was amorpha-4,11-diene, and that amorpha-4,11-diene had a retention time of 3.7 minutes using this GC protocol. Beta- or trans-caryophyllene was used as an internal standard for quantitation. Amorpha-4,11-diene titer was calculated using the ratio of internal standard to amorpha-4,11-diene peak areas based upon a quantitative calibration curve of purified amorpha-4,11-diene (0.63-10 mg/L of KJF17-109-3) in caryophyllene-spiked ethyl acetate.

As shown in FIGS. 10A and 10B, strains B153 and B282, which expressed the *Staphylococcus aureus* HMGR and HMGS, produced elevated levels of amorpha-4,11-diene compared to strains B32, B210, B255, B256, and B292, which expressed the *Saccharomyces cerevisiae* tHMGR and HMGS.

Example 11

This example demonstrates increased production of amorpha-4,11-diene by an *Escherichia coli* host strain grown at suboptimal temperature.

A seed culture of host strain B32 was established by adding 0.5 mL of a stock aliquot of the strain to a 250 mL flask containing 50 mL M9-MOPS medium and antibiotics as detailed in Table 1, and by growing the culture overnight at 37° C. on a rotary shaker at 250 rpm.

The seed culture was used to inoculate at an initial $OD_{600}$ of approximately 0.05 four 250 mL flasks, each containing 40 mL fermentor batch medium (see Table 6 for medium composition), 100 mM MOPS buffer pH7.1, and antibiotics. The cultures were incubated on a rotary shaker at 250 rpm at either 30° C. or 37° C. until they reached an $OD_{600}$ of 0.18 to 0.22, at which point the production of amorpha-4,11-diene in the host cells was induced by adding 40 uL of 1M IPTG to the culture medium. At the time of induction, the cultures were overlain with 8 mL of an organic overlay to capture the amorpha-4,11-diene. Samples were taken once a day, and analyzed as described in Example 10.

As shown in FIGS. 11A and 11B, fermentation at 30° C. did not affect cell growth, but led to an approximately 50% increase in the specific production of amorpha-4,11-diene by the *Escherichia coli* host strain.

Example 12

This example demonstrates increased production of amorpha-4,11-diene by an *Escherichia coli* host strain grown under restricted carbon source conditions.

A seed culture of host strain B32 for fermentation runs 050608-1 and 050629-1 was established by adding 0.25 uL of a stock aliquot of the strain to a 250 mL flask containing 50 mL M9-MOPS medium and antibiotics as detailed in Table 1, and by incubating the culture at 37° C. on a rotary shaker at 250 rpm until it reached an $OD_{600}$ of 1 to 2.

A seed culture of host strain B32 for fermentation run 060403-3 was established by adding a stock aliquot of the strain to a 250 mL flask containing 50 mL M9-MOPS medium and antibiotics as detailed in Table 1, and by incubating the culture overnight at 37° C. on a rotary shaker at 250 rpm. The seed culture was used to inoculate at an initial $OD_{600}$ of approximately 1 a 250 mL flask containing 40 mL M9-MOPS medium and antibiotics, and the culture was again incubated at 37° C. on a rotary shaker at 250 rpm until it reached an $OD_{600}$ of 3 to 5.

For all fermentation processes, the $KH_2PO_4$, $K_2HPO_4 3H_2O$, EDTA, citric acid, and $(NH_4)_2SO_4$ were heat sterilized in the bioreactor (2 L Applikon Bioconsole ADI 1025s with ADI 1010 controllers, Applikon Biotechnology, Foster City, Calif.). The remaining media components were filter sterilized as stock solutions and injected through the headplate. Table 3 shows the final media composition for fermentation runs 050608-1 and 050629-1. Table 4 shows the final media composition for fermentation run 060403-3. The starting volume for run 050608-1 was 0.8 L, the starting volume for 050629-1 was 1.2 L and the starting volume for 060403-3 was 1 L. All runs were inoculated by injecting 50 mL of the seed culture through the headplate.

TABLE 3

Composition of Fermentation Medium of Fermentation Runs 050608-1 and 050629-1

| Component | Batch Medium (per L) | Feed Solution (per L) |
|---|---|---|
| Glucose | 5 g | 590-650 g |
| $KH_2PO_4$ | 4.2 g | — |
| $K_2HPO_4 3H_2O$ | 15.7 g | — |
| Citric acid | 1.7 g | — |
| $(NH_4)_2SO_4$ | 2 g | — |
| $MgSO_4 7H_2O$ | 1.2 g | 12 g |
| EDTA | 8.4 mg | 13 g |
| $CoCl_2 6H_2O$ | 0.25 mg | 0.4 mg |
| $MnCl_2 4H_2O$ | 1.5 mg | 2.35 mg |
| $CuCl_2 2H_2O$ | 0.15 mg | 0.25 mg |
| $H_3BO_4$ | 0.3 mg | 0.5 mg |
| $Na_2MoO_4 2H_2O$ | 0.25 mg | 0.4 mg |
| $Zn(CH_3COO)_2 2H_2O$ | 1.3 mg | 1.6 mg |
| Fe(III)citrate hydrate | 10.0 mg | 4.0 mg |
| Thiamine HCl | 4.5 mg | — |
| Carbenicillin | 100 ug | 100 ug |
| Tetracycline | 5 ug | 5 ug |
| Chloramphenicol | 34 ug | 34 ug |

TABLE 4

Composition of Fermentation Medium of Fermentation Run 060403-3

| Component | Batch medium (per L) | Feed solution (per L) |
|---|---|---|
| Glucose | 15 g | 650 g |
| $KH_2PO_4$ | 4.2 g | — |
| $K_2HPO_4 3H_2O$ | 15.7 g | — |
| Citric acid | 1.7 g | — |
| $(NH_4)2SO_4$ | 2 g | — |
| $MgSO_4 7H_2O$ | 1.2 g | 12 g |
| EDTA | 8.4 mg | 13 mg |
| $CoCl_2 6H_2O$ | 2.5 mg | 4 mg |
| $MnCl_2 4H_2O$ | 15 mg | 23.5 mg |
| $CuCl_2 2H_2O$ | 1.5 mg | 2.5 mg |
| $H_3BO_4$ | 3 mg | 5 mg |
| $Na_2MoO_4 2H_2O$ | 2.5 mg | 4 mg |
| $Zn(CH_3COO)_2 2H_2O$ | 13 mg | 16 mg |
| Fe(III)citrate hydrate | 100 mg | 40 mg |
| Thiamine HCl | 4.5 mg | — |
| Carbenicillin | 100 ug | 100 ug |
| Tetracycline | 5 ug | 5 ug |
| Chloramphenicol | 34 ug | 34 ug |

For fermentation run 050608-1 (excess carbon), the feed was initiated at induction, and feed rates were adjusted manually to provide glucose in the concentrations shown in FIG. 12C. For fermentation run 050629-1 (carbon-restricted), the feed was delivered to the fermentor according to the protocol shown in Table 5. For fermentation run 060403-3 (lowest carbon), the feed was started automatically when the initial glucose bolus (15 g) was exhausted and the dissolved oxygen spiked. Up to a maximum of 27.6 g/hr, the rate of the feed was calculated according to the following equation:

$$m_s(t) = S(t_0) \mu e^{\mu(t-t_0)}$$

$$\mu = 0.12$$

$$S(t_0) = 15 \text{ g}$$

wherein $t_0$ is the time at which the initial glucose was depleted. Upon reaching the maximum rate, the glucose feed was restricted to a rate of 9.5 g/hr, and held constant at this rate for the remainder of the run.

TABLE 5

Feed Protocol for Fermentation Run 050629-1

| Run Time (hours) | Glucose Feed Rate (g/hr) |
|---|---|
| 0 | 0 |
| 7 | 0.37 |
| 10 | 0.74 |
| 12 | 1.11 |
| 14 | 1.48 |
| 16 | 2.22 |
| 18 | 2.96 |
| 20 | 3.69 |
| 22 | 4.80 |
| 24 | 5.91 |
| 31 | 7.39 |
| 33 | 5.54 |
| 47 | 3.69 |

Runs 050608-1 and 050629-1 were carried out at 37° C. Airflow in the bioreactor was set at 1-2 L/min; pH was maintained at 7 using ammonium hydroxide and/or sodium hydroxide; initial agitation was 500-600 rpm; foam was controlled with antifoam B (Sigma-Aldrich, St. Louis, Mo.); the dissolved oxygen levels were maintained above 30% using an agitation cascade. After 5-6 hours of cultivation, production of amorpha-4,11-diene by the host cells was induced by adding 0.8 mL of 1 M IPTG to run 050608-1 and 1.2 mL IPTG to run 050629-1. Upon induction, the culture temperature was reduced to 30° C.

Run 060403-3 was carried out at 30° C. Airflow in the bioreactor was set at 1-2 L/min; pH was maintained at 7 using ammonia hydroxide. Dissolved oxygen was maintained above 30% by an agitation cascade and oxygen enrichment. At an $OD_{600}$ of approximately 28 (19 hours after inoculation), production of amorpha-4,11-diene by the host cells was induced by adding 1 mL 1 M IPTG.

Amorpha-4,11-diene was captured and extracted according to two different protocols. For runs 050608-1 and 050629-1, volatile amorpha-4,11-diene present in the off-gas was captured by venting the off-gas through a gas-washer containing 200 mL heptanol. The heptanol was then diluted into ethyl acetate until the amorpha-4,11-diene concentration in the sample was between 0.63 mg/L and 20 mg/L. For run 060403-3, amorpha-4,11-diene was captured in the bioreactor by adding 200 mL of an organic overlay to the fermentor at the time of induction. Product concentration was measured by combining 25 uL broth plus organic overlay with 975 uL acetonitrile, shaking the sample at maximum speed on a Fisher Vortex Genie 2™ mixer (Scientific Industries, Inc., Bohemia, N.Y.) for at least 3 minutes, removing cells from the sample by centrifugation, and diluting the acetonitrile solution into ethyl acetate until the amorpha-4,11-diene concentration in the sample was between 0.63 and 20 mg/L. The ethyl acetate samples were analyzed by GC/MS as described in Example 10.

As shown in FIGS. 12A and 12B, fermentation run 050608-1 (excess carbon) resulted in low maximum cell densities and low production of amorpha-4,11-diene, respectively, correlating, at least in part, to the relatively rapid increase in acetate levels (FIG. 12D). In comparison, fermentation run 050629-1 (carbon-restricted) resulted in increased production of amorpha-4,11-diene (FIG. 12B), and delayed the onset of acetate production. These results are consistent with the hypothesis that excess glucose feeds lead to rapid acetate production and early cell death.

Further glucose restriction as achieved by fermentation run 060403-3 (lowest carbon) resulted in low acetate production for over 100 hours (FIG. 12D), and significantly higher maximum cell density and amorpha-4,11-diene production (FIGS. 12A and 12B).

Example 13

This example demonstrates increased amorpha-4,11-diene production by an *Escherichia coli* host strain grown under restricted carbon source conditions and at suboptimal temperature.

A seed culture of host strain B153 was established by adding a stock aliquot of the strain to a 250 mL flask containing 50 mL M9-MOPS medium and antibiotics as detailed in Table 1, and growing the culture at 37° C. on a rotary shaker at 250 rpm to an $OD_{600}$ of 3.5 to 4.5.

2 L bioreactors (Biocontroller ADI 1010 with Bioconsole ADI 1025, Applikon Biotechnology, Foster City, Calif.) were set up and run in the same way as described in Example 12 for run 060403-3, except that strain and induction time were varied.

Production of amorpha-4,11-diene in the host cells was induced by adding 1 mL of 1 M IPTG to the culture medium. In the fermentation run shown in FIG. 13A, amorpha-4,11-diene synthesis was induced at an $OD_{600}$ of approximately 2, while the fermentor still contained excess glucose. In the fermentation run shown in FIG. 13B, amorpha-4,11-diene synthesis was induced at an $OD_{600}$ of approximately 33, which was after the glucose-restricted feed had started.

Amorpha-4,11-diene was captured and extracted according to two different protocols. For the fermentation run shown in FIG. 13A, volatile amorpha-4,11-diene present in the off-gas was captured by venting the off-gas through a gas-washer containing 200 mL heptanol. The heptanol was then diluted into ethyl acetate until the amorpha-4,11-diene concentration in the sample was between 0.63 and 20 mg/L. For the fermentation run shown in FIG. 13B, amorpha-4,11-diene was captured by adding 200 mL of an organic overlay to the fermentor at the time of induction.

Amorpha-4,11-diene was extracted from the culture medium by combining 25 uL broth with 975 uL acetonitrile, shaking the sample at maximum speed on a Fisher Vortex Genie 2™ mixer (Scientific Industries, Inc., Bohemia, N.Y.) for at least 3 minutes, removing cells from the sample by centrifugation, and diluting the acetonitrile solution into ethyl acetate until the amorpha-4,11-diene concentration in the sample was between 0.63 and 20 mg/L. The ethyl acetate samples were analyzed by GC/MS as described in Example 10. For the fermentation run shown in FIG. 13A, the total amount of amorpha-4,11-dien was derived by combining the amounts present in the off-gas and in the culture medium, and dividing the total by the fermentor volume.

The fermentation shown in FIG. 13A reached a maximal $OD_{600}$ of 93 and a maximal amorpha-4,11-diene concentration of 3.2 g/L. In contrast, the fermentation shown in FIG. 13B reached a maximal $OD_{600}$ of 245 and a maximal amorpha-4,11-diene concentration of 15 g/L. A likely explanation for the differences in culture growth and amorpha-4,11-diene production levels observed in the two cultures is that in the fermentation run shown in FIG. 13A amorpha-4,11-diene production was induced before the excess glucose was consumed, and that the unrestricted availability of glucose caused cell death by enabling the build-up of toxic levels of intermediates of the mevalonate pathway. In the fermentation run shown in FIG. 13B, induction occurred after glucose delivery was restricted, which prevented the build-up of pathway intermediates, leading to higher cell density and amorpha-4,11-diene production levels.

Example 14

This example demonstrates increased amorpha-4,11-diene production by an *Escherichia coli* host strain grown under restricted carbon and nitrogen source conditions and at suboptimal temperature.

A seed culture of host strain B86 was established by adding a stock aliquot of the strain to a 250 mL flask containing 50 mL M9-MOPS medium and antibiotics as detailed in Table 1. The culture was grown overnight at 37° C. on a rotary shaker at 250 rpm, sub-cultured the following morning into the same medium at an $OD_{600}$ of approximately 1, and grown again at 37° C. and 250 rpm to an $OD_{600}$ of 3 to 5.

Four 2 L bioreactors (Biocontroller ADI 1010 with Bioconsole ADI 1025, Applikon Biotechnology, Foster City, Calif.) were set up and run in the same way as described in Example 12 for run 060403-3, except that the nitrogen restricted runs did not contain ammonia sulfate in the feed.

An exponential glucose feed with a 6 hour doubling time was initiated automatically when the initial glucose bolus (15 g) was exhausted and the dissolved oxygen spiked. Up to a maximum of 30.4 g/hr, the rate of the feed was calculated according to the following equation:

$$m_s(t) = S_0 \mu e^{\mu(t-t_0)}$$

$$\mu = 0.12 \text{ min}^{-1}$$

$$S_0 = 15 \text{ g}$$

wherein μ is the specific growth rate, and $t_0$ is the time at which the initial glucose bolus was depleted. Upon reaching the maximum rate, the glucose feed was reduced to a rate of 11.4 g/hr, and held constant at this rate for the remainder of the run. In fermentation runs 060710-4, 060724-5, and 060619-5 (carbon- and nitrogen-restricted), the glucose feed was further reduced when ammonia restriction lead to glucose accumulation in the medium.

Fermentation was carried out at the reduced temperature of 30° C. Airflow in the bioreactor was set at 1 vvm; initial agitation was at 700 rpm; foam was controlled with antifoam B (Sigma-Aldrich, St. Louis, Mo.); and dissolved oxygen tension was controlled at 40% using an agitation cascade (700-1,200 rpm) and oxygen enrichment. In fermentation run 060327-3 (carbon-restricted), the pH was maintained at 7 using 20% NH$_4$OH; in fermentation runs 060710-4, 060724-5, and 060619-5 (carbon- and nitrogen-restricted), pH was maintained at 7 initially using 20% NH$_4$OH, and starting at 72 hours using a 50/50 mixture of 2.5 N NaOH and 10 N NH$_4$OH, to further restrict the amount of ammonia going into the fermentor.

Production of amorpha-4,11-diene in the host cells was induced at an OD$_{600}$ of approximately 30 by adding 1 mL of 1 M IPTG to the culture medium.

Amorpha-4,11-diene was captured by overlaying the medium with 10% (v/v) of an organic overlay. Amorpha-4,11-diene was then extracted by combining 25 uL of broth with 975 uL methanol, shaking the sample at maximum speed on a Fisher Vortex Genie2™ mixer (Scientific Industries, Inc., Bohemia, N.Y.) for at least 15 minutes, removing cells from the sample by centrifugation, and adding 10 uL of the methanol solution to 990 uL ethyl acetate containing 10 uL/L trans-caryophylene.

Samples were analyzed by GC/MS as described in Example 10.

FIGS. 14A-E show data from fermentation run 060327-3 (carbon-restricted). The fermentation produced a maximum concentration of amorpha-4,11-diene of 16 g/L (FIG. 14A). The maximum volumetric productivity of the host strain was more than 200 mg/L/hour (FIG. 14B). The maximum specific productivity of the host strain was >2 mg/L/hour/OD$_{600}$ (FIG. 14C). The concentration of ammonia in the culture medium was about 30 mM at the start of the fermentation run, rose to about 76 mM upon addition of the feed solution during the exponential growth phase, and remained above 60 mM for the remainder of the run (FIG. 14D). The maximum OD$_{600}$ reached was about 290 (FIG. 14D), corresponding to 116 g DCW/L. The concentration of glucose in the culture medium dropped from 15 g/L to below 1 g/L in less than 20 hours, and remained low (FIG. 14E). Acetate levels were low throughout the fermentation (FIG. 14E).

FIGS. 15A-E show data from fermentation runs 060710-4, 060724-5, and 060619-5 (carbon- and nitrogen-restricted). The fermentations produced a maximum concentration of amorpha-4,11-diene from about 20 g/L to 30 g/L (FIG. 15A). The maximum volumetric productivity of the host strain was more than 400 mg/L/hour in all three fermentation runs (FIG. 15B), which is significantly higher than the maximum volumetric productivity obtained in the nitrogen unrestricted fermentation (FIG. 14B). The maximum specific productivity of the host strain was >2 mg/L/hour/OD$_{600}$ for all runs, and remained high throughout the runs (FIG. 15C). The concentration of ammonia in the culture medium was about 35 mM to 50 mM at the start of the fermentation runs, dropped upon addition of the feed solution during exponential growth, and remained below 10 mM for the remainder of the run (FIG. 15D). (The lowered ammonia levels compared to fermentation run 060327-3 (FIG. 14D) are due to the lack of ammonia in the feed solution and reduced ammonia in the base used to maintain the pH. Fermentation runs 060710-4 and 060619-5 showed a spike in ammonia concentration at the end of the runs, but the spikes occurred after the bulk of the production of amorpha-4,11-diene.) The maximum OD$_{600}$ reached was 170 to 220 (FIG. 15D), corresponding to 68 g to 88 g DCW/L. The concentration of glucose in the culture medium dropped from 15 g/L to below 1 g/L in less than 20 hours, and remained low (FIG. 15E). Acetate levels were low throughout the fermentation runs (FIG. 15E).

Example 15

This example describes the production of amorpha-4,11-diene via the DXP pathway in an *Escherichia coli* host strain.

Seed cultures of host strains B003, B617, B618, and B619 were established by adding a stock aliquot of each strain to separate 125 mL flasks containing 25 mL M9-MOPS and antibiotics as detailed in Table 1, and by growing the cultures overnight.

The seed cultures were used to inoculate at an initial OD$_{600}$ of approximately 0.05, separate 250 mL flasks containing 40 mL M9-MOPS medium, 45 ug/mL thiamine, micronutrients, 1.00E-5 mol/L FeSO4, 0.1 M MOPS, 0.5% yeast extract, 20 g/L of D-glucose, and antibiotics. Cultures were incubated at 30° C. in a humidified incubating shaker at 250 rpm until they reached an OD$_{600}$ of 0.2 to 0.3, at which point the production of amorpha-4,11-diene in the host cells was induced by adding 40 uL of 1M IPTG to the culture medium.

At the time of induction, the cultures were overlain with 8 mL of an organic overlay to capture the amorpha-4,11-diene. Samples were taken at various time points, and amorpha-4,11-diene was extracted and analyzed by GC/MS as described in Example 10. Experiments were performed using 2 independent clones of each host strain, and results were averaged. Deviation between samples was found to be less than 10%.

Figure 16:
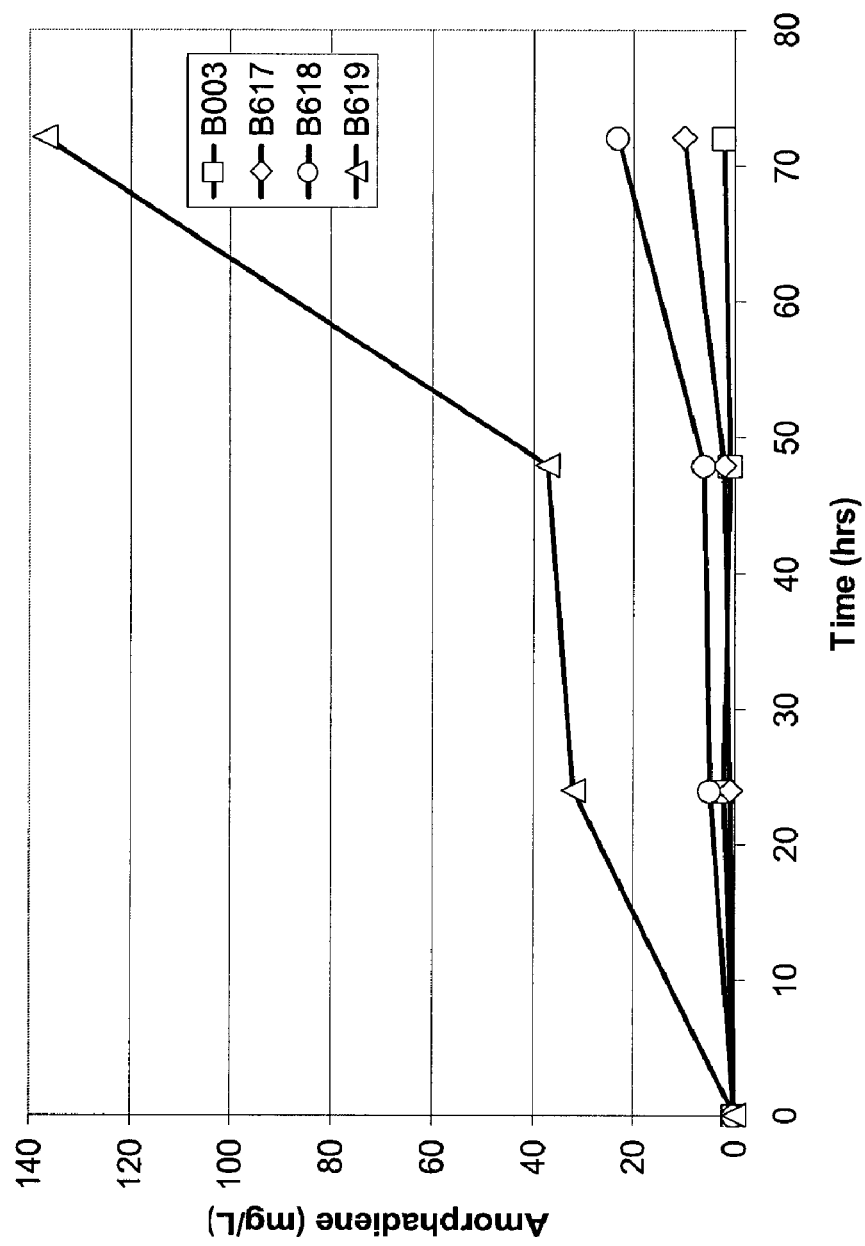
FIG. 16 shows production of amorpha-4,11-diene via the DXP pathway by an *Escherichia coli* host strain.

As shown in FIG. 16, *Escherichia coli* host strain B619, which comprises nucleotide sequences encoding enzymes of the full engineered DXP pathway, produced approximately 45 mg/g DCW amorpha-4,11-diene.

Example 16

This example describes the production of 3-methyl-but-3-en-1-ol and 3-methyl-but-2-en-1-ol in *Escherichia coli* host strains.

Seed cultures of host strains B286, B287, B288, and B291 were established by streaking out a stock aliquot of each strain on LB agar containing antibiotics as detailed in Table 1. Three independent colonies were picked for each strain, and each colony was inoculated into 7 mL of LB media containing antibiotics. The cultures were grown overnight at 37° C. on a rotary shaker at 250 rpm until late exponential phase. The cultures were then inoculated at an OD$_{600}$ of approximately 0.05, into a 250 mL flask containing 40 ml of M9-MOPS, 2% glucose, 0.5% yeast extract, and antibiotics. The cultures were grown overnight at 37° C. on a rotary shaker at 250 rpm until they reached an OD$_{600}$ of approximately 0.2, at which point they were induced by adding 40 uL of 1 M IPTG. The cultures were grown for 72 hours at 30° C. on a rotary shaker at 250 rpm. One to two times per day, the OD$_{600}$ of each culture was measured, and a 700 uL sample was removed. To extract the 3-methyl-but-3-en-1-ol and 3-methyl-but-2-en-1-ol from the culture broth, 600 uL of ethyl acetate was added to 300 uL of each removed sample. The sample was then vortexed for 15 minutes, and 400 uL of the upper ethyl acetate phase was transferred to a clean glass vial for analysis.

The samples were analyzed on a Hewlett-Packard 6890 gas chromatograph/mass spectrometer (GC/MS). A 1 uL sample was separated on the GC using a DB-5 column (Agilent Technologies, Inc., Palo Alto, Calif.) and helium carrier gas. The temperature program for the analysis was as follows: 60° C. for 3 minutes, increasing temperature at 60° C./minute to a temperature of 300° C., and a hold at 300° C. for 2 minutes. The total run time was 9 minutes. The resolved samples were analyzed by a Hewlett-Packard model 5973 mass selective detector. Previous mass spectra demonstrated that 3-methyl-3-buten-1-ol and 3-methyl-2-buten-1-ol have a retention time of 2.067 minutes using this GC protocol. To focus detection on 3-methyl-but-3-en-1-ol and 3-methyl-but-2-en-1-ol, a selective-ion-monitoring method was employed that monitors only ions 56 and 68 in 3-methyl-but-3-en-1-ol and 3-methyl-but-2-en-1-ol.

Example 17

This example describes the production of amorpha-4,11-diene by a *Saccharomyces cerevisiae* host strain.

The generation of host strain EPY224 is described in Ro et al. (*Nature* 440: 940-943; 2006) and in PCT Patent Publication WO2007/005604. Host strain EPY224 was cured of expression plasmid pRS425ADS by growth in YPD medium (Methods in Yeast Genetics: A Cold Spring Harbor Laboratory Course Manual, 2005 ed., ISBN 0-87969-728-8), plating for single colonies on YPD agar, and then patching single colonies onto CSM-Met His agar and CSM-Met Leu agar. Clones that grew on CSM-Met His agar but not on CSM-Met Leu agar were cured (i.e., had lost the plasmid pRS425ADS). One such clone was designated EPY300. EPY300 was transformed with expression plasmid pRS425-ADS-LEU2d, a plasmid identical to pRS425-ADS except that instead of LEU2 it contains a LEU2d selection marker (Erhart and Hollenberg (1983) *J. Bacteriol.* 156: 625-635) yielding host strain Y185.

Y185 host cell transformants were selected on synthetic defined media, containing 2% glucose and all amino acids except histidine, leucine, and methionine (CSM-glucose; MP Biomedicals, Solon, Ohio). The host strain EPY300 is auxotrophic for leucine biosynthesis (leu2), but expression plasmid pRS425-ADS-LEU2d in Y185 restores leucine prototrophy (LEU2). Single colonies were patched onto selective medium (CSM-glucose-histidine, leucine, methionine), and grown for 2 days. The cells were scraped from the plate and transferred to 1 mL of 25% (v/v) glycerol in a cryotube. The suspension was mixed, and then stored at −80° C.

Seed flasks of host strain Y185 were established by adding a stock aliquot of the strain to a 125 mL flask containing 25 mL of CSM-glucose lacking leucine and methionine, and by growing the cultures overnight. The cultures were used to inoculate at an initial OD$_{600}$ of approximately 0.05 a 250 mL baffled flask containing 40 mL of synthetic defined media lacking leucine, and containing 0.2% glucose, 1.8% galactose, and 1 mM methionine. The culture was incubated at 30° C. on a rotary shaker at 200 rpm. Because the presence of glucose in the media prevents induction of the GAL1 promoter by galactose, amorpha-4,11-diene production was not induced until the cells had used up the glucose in the media and had switched to using galactose as their main carbon source. At the time of inoculation, the cultures were overlain with 8 mL of an organic overlay to capture the amorpha-4,11-diene. Samples were taken at 72 hours by transferring 5 uL of the organic solvent layer to a clean glass vial containing 500 uL ethyl acetate containing a known concentration of beta- or trans-caryophyllene as an internal standard.

The organic overlay/ethyl acetate samples were analyzed on a Hewlett-Packard 6890 gas chromatograph/mass spectrometer (GC/MS) as described in Example 10.

After 72 hours of growth, 3 yeast cultures were found to produce 60.68, 54.48, and 59.25 mg/L amorpha-4,11-diene.

Example 18

This example describes the production of amorpha-4,11-diene in an *Saccharomyces cerevisiae* host strain where the host strain includes a native mevalonate pathway as well as a heterologous mevalonate pathway that is under control of a heterologous regulatory control.

Yeast strains CEN.PK2-1C (Y002) (MATA; ura3-52; trp1-289; leu2-3,112; his3Δ1; MAL2-8C; SUC2) and CEN.PK2-1D (Y003) (MATalpha; ura3-52; trp1-289; leu2-3,112; his3Δ1; MAL2-8C; SUC2) (J. P. van Dijken et al., *Enzyme Microb Technol* 26, 706 (Jun. 1, 2000) were cultivated in either standard rich medium (YPD) or in defined synthetic medium (D. Rose, F. Winston, P. Heiter, *Methods in yeast genetics: a laboratory course manual*. (Cold Spring Harbor Laboratory Press, Cold Spring Harbor, N.Y., 1990) lacking appropriate nutrients allowing for selection of integrative transformants, plasmid retention, and meiotic progeny.

Figure 7:
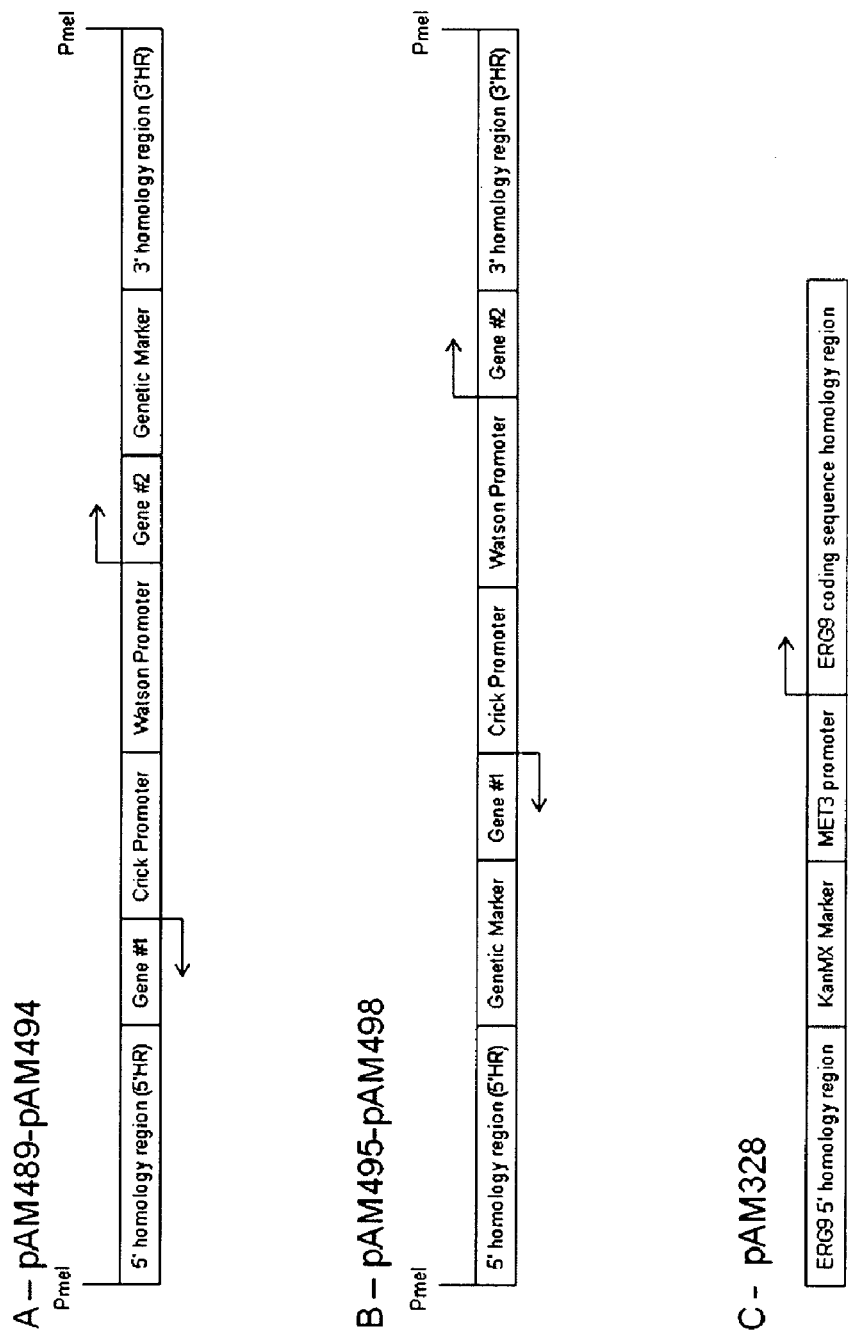
FIGS. 7A-C are schematics for the construction of plasmids pAM489-pAM498 and for pAM328.

DNA-mediated transformations into *S. cerevisiae* were conducted using the lithium acetate procedure as described by R. H. Schiestl, R. D. Gietz, *Curr Genet.* 16, 339 (December, 1989). All gene disruptions and replacements were confirmed by phenotypic analysis, colony polymerase chain reaction ("PCR") and sequencing of amplified genomic DNA. Plasmids pAM489-pAM498 were constructed using the pCR 2.1 (Invitrogen, Carlsbad Calif.) and are schematically described by FIG. 7A-C and Table 6. The HISMX marker sequences are described in M. S. Longtine et al., *Yeast* 14, 953 (July, 1998). Propagation of plasmid DNA was performed in *Escherichia coli* strain DH5α.

TABLE 6

| Strain | 5'HR | Gene #1 | Crick Promoter | Watson Promoter | Gene #2 | Genetic Marker | 3'HR |
|---|---|---|---|---|---|---|---|
| pAM489 | TRP1 | tHMGR | GAL1 | GAL10 | ERG20 | TRP1 | TRP1 |
| pAM490 | TRP1 | tHMGR | CUP1 | CUP1 | ERG20 | TRP1 | TRP1 |
| pAN491 | URA3 | tHMGR | GAL1 | GAL10 | ERG13 | URA3 | URA3 |
| pAM492 | URA3 | IDI1 | CUP1 | CUP1 | tHMGR | URA3 | URA3 |
| pAM493 | ADE1 | tHMGR | GAL1 | GAL10 | IDI1 | ADE1 | URA3 |
| pAM494 | ADE1 | tHMGR | CUP1 | CUP1 | IDI1 | ADE1 | ADE1 |

TABLE 6-continued

| Strain | 5'HR | Gene #1 | Crick Promoter | Watson Promoter | Gene #2 | Genetic Marker | 3'HR |
|---|---|---|---|---|---|---|---|
| pAM495 | HIS3 | ERG12 | GAL1 | GAL10 | ERG10 | HISMX | HIS3 |
| pAM496 | HIS3 | ERG12 | CUP1 | CUP1 | ERG10 | HISMX | HIS3 |
| pAM497 | LEU2 | ERG19 | GAL1 | GAL1 | ERG8 | HISMX | LEU2 |
| pAM498 | LEU2 | ERG19 | CUP1 | CUP1 | ERG8 | HISMX | LEU2 |

S. cerevisiae strains Y002 and Y003 were prepared for introduction of inducible mevalonate pathway genes by the following. The ERG9 promoter was replaced with the S. cerevisiae MET3 promoter by PCR amplification of the KanMX-PMET3 region from pAM328 (SEQ ID NO: 43) using primers 50-56-pw100-G (SEQ ID NO: 44) and 50-56-pw101-G (SEQ ID NO: 45) containing 45 basepairs of homology to the native ERG9 promoter. 10 μg of the resulting PCR product was transformed into exponentially growing Y002 and Y003 strains using 40% w/w polyethelene glycol 3350 (Sigma-Aldrich St Louis, Mo.), 100 mM lithium acetate (Sigma), 10 μg Salmon Sperm DNA (Invitrogen) and incubation at 30° C. for 30 minutes followed by a 42° C. heat shock for 30 minutes (as described by Schiestl & Gietz, Curr. Genet. 16: 339 (1989)). Positive recombinants were identified by their ability to grow on rich medium containing 0.5 μg/ml Geneticin (Invitrogen Co, Carlsbad, Calif.) and confirmed by diagnostic PCR. The resultant clones were given the designation Y93 (MAT A) and Y94 (MAT alpha). Next, the ADE1 open reading frame was replaced with the Candida glabrata LEU2 gene (CgLEU2). The 3.5 KB CgLEU2 genomic locus was amplified from C. glabrata genomic DNA (ATCC, Manassas, Va.) using primers 61-67-CPK066-G (SEQ ID NO: 46) and 61-67-CPK067-G (SEQ ID NO: 47) containing 50 basepairs of flanking homology to the ADE1 open reading frame (ORF). 10 μg of the resulting PCR product was transformed into exponentially growing Y93 and Y94 as described above. ade1-strains were selected for growth in the absence of leucine supplementation and confirmed by diagnostic PCR. The resultant clones were given the designation Y176 (MAT A) and Y177 (MAT alpha).

To generate S. cerevisiae strain Y188, 2 μg's of plasmid DNA from pAM491 (SEQ ID NO: 48) and pAM495 (SEQ ID NO:49), respectively, were digested overnight with PmeI (New England Biolabs, Beverly, Mass.) and introduced into exponentially growing Y176 as described above. Positive recombinants were selected for by growth on medium lacking uracil and histidine. Integration into the correct genomic locus was confirmed by diagnostic PCR.

To generate S. cerevisiae strain Y189, 2 μg's of plasmid DNA from pAM489 (SEQ ID NO: 50) and pAM497 (SEQ ID NO: 51), respectively, were digested overnight with PmeI and introduced into exponentially growing Y177 as described above. Positive recombinants were selected for by growth on medium lacking tryptophan and histidine. Integration into the correct genomic locus was confirmed by diagnostic PCR.

Approximately $1 \times 10^7$ cells from Y188 and Y189 were mixed on a YPD medium plate for 6 hours at room temperature to allow for mating. The mixed cell culture was then plated to medium lacking histidine, uracil and tryptophan to select for growth of diploid cells. 2 μg of plasmid DNA from pAM493 (SEQ ID NO: 52) was digested overnight with PmeI and introduced into exponentially growing diploid cells as described above. Positive recombinants were selected for by growth on medium lacking adenine. Integration into the correct genomic locus was confirmed by diagnostic PCR. The resultant strain was given the designation Y238.

To generate haploid strains containing the full complement of introduced genes, Y238 was sporulated in 2% potassium acetate and 0.02% raffinose liquid medium. Approximately 200 genetic tetrads (tetrads are four-spored meiotic products) were isolated using a Singer Instruments MSM300 series micromanipulator (Singer Instrument Co, LTD. Somerset, UK). Independent genetic isolates containing the appropriate complement of introduced genetic material were identified by their ability to grow in the absence of adenine, histidine, uracil, and tryptophan. Integration of all introduced DNA was confirmed by diagnostic PCR. The resultant strains were given the designation Y210 (MAT A) and Y211 (MAT alpha).

2 μg of plasmid DNA from pAM426 (SEQ ID NO:53), containing S. cerevisiae condon optimized Amorphadeine Synthase (ADS) expressed from the S. cerevisiae GAL1 promoter, was introduced into exponentially growing Y210 and Y211 as described above. S. cerevisiae strains that contained the pAM426 plasmid were selected for by their ability to grow in the absence of leucine supplementation. The resultant strains were given the designation Y225 (MAT A) and Y227 (MAT alpha).

2 μg of plasmid DNA from pAM322 (SEQ ID NO: 54), containing S. cerevisiae condon optimized Amorphadeine Synthase (ADS) and cytochrome P450 monooxygenase (AMO) expressed from the S. cerevisiae GAL1 and the cytochrome P450 oxidoreductase (CPR) expressed from the S. cerevisiae GAL10 promoter, was introduced into exponentially growing Y210 and Y211 as described above. S. cerevisiae strains that contained the pAM322 plasmid were selected for by their ability to grow in the absence of leucine supplementation. The resultant strains were given the designation Y222 (MAT A) and Y224 (MAT alpha).

Example 19

This example describes the production of α-farnesene or β-farnesene in Escherichia coli host strains.

Seed cultures of host strains B552 and B592 were established by adding a stock aliquot of each strain to a 125 mL flask containing 25 mL M9-MOPS, 0.8% glucose, 0.5% yeast extract, and antibiotics as detailed in Table 1, and by growing the cultures overnight.

The seed cultures were used to inoculate at an initial $OD_{600}$ of approximately 0.05, 250 mL flasks containing 40 mL M9-MOPS, 2% glucose, 0.5% yeast extract, and antibiotics. Cultures were incubated at 30° C. on a rotary shaker at 250 rpm until they reached an $OD_{600}$ of approximately 0.2, at which point the production of α-farnesene or β-farnesene in the host cells was induced by adding 40 uL of 1 M IPTG. At the time of induction, the cultures were overlain with 8 mL of an organic overlay to capture the α-farnesene. Samples were taken every 24 hours up to 120 hours (total of 5 time points) by transferring 2 uL to 10 uL of the organic overlay layer to a clean glass vial containing 1 mL ethyl acetate spiked with trans-caryophyllene as an internal standard. In addition, 1 mL aliquots of the cultures were spun down, cell pellets were resuspended in 250 uL sterile water, and the cell suspensions were transferred to a glass vial containing 1 mL ethyl acetate spiked with trans-caryophyllene as an internal standard. In addition, 0.5 mL aliquots of the whole culture broth were added to a glass vials containing 1 mL ethyl acetate spiked with trans-caryophyllene as an internal standard. The whole culture broth samples were extracted in the ethyl acetate by vortexing the glass vials for 10 minutes, after which 600 uL of the ethyl acetate extraction was transferred to a clean glass vial.

The organic overlay/ethyl acetate samples and the ethyl acetate-extracted whole culture broth samples were analyzed on an Agilent 6890N gas chromatograph equipped with an Agilent 5975 mass spectrometer (GC/MS) in full scan mode (50-500 m/z). To expedite run times, the temperature program and column matrix was modified to achieve optimal peak resolution and the shortest overall runtime. A 1 uL sample was separated using a HP-5MS column (Agilent Technologies, Inc., Palo Alto, Calif.) and helium carrier gas. The temperature program for the analysis was as follows: 150° C. hold for 3 minutes, increasing temperature at 25 C/minute to a temperature of 200° C., increasing temperature at 60° C./minute to a temperature of 300° C., and a hold at 300° C. for 1 minute. Previous mass spectra demonstrated that the β-farnesene synthase product was β-farnesene, and that β-farnesene had a retention time of 4.33 minutes using this GC protocol. Farnesene titers were calculated by comparing generated peak areas against a quantitative calibration curve of purified β-farnesene (Sigma-Aldrich Chemical Company, St. Louis, Mo.) in trans-caryophyllene-spiked ethyl acetate.

Host strain B592 produced approximately 400 mg/L of α-farnesene at 120 hours (averaged over 3 independent clones), and had a maximal specific productivity of approximately 46 mg/L/OD$_{600}$. Host strain B552 produced approximately 1.1 g/L of β-farnesene at 120 hours (averaged over 3 independent clones), and had a maximal specific productivity of approximately 96 mg/L/OD$_{600}$ (1 representative clone).

Example 20

This example describes the production of β-farnesene via the DXP pathway in an *Escherichia coli* host strain.

Seed cultures of host strains B650, B651, B652, and B653 were established by adding a stock aliquot of each strain to separate 125 mL flasks containing 25 mL M9-MOPS and antibiotics as detailed in Table 1, and by growing the cultures overnight.

The seed cultures were used to inoculate at an initial OD$_{600}$ of approximately 0.05 separate 250 mL flasks containing 40 mL M9-MOPS minimal medium, 45 ug/mL thiamine, micronutrients, 1.00E-5 mol/L FeSO4, 0.1 M MOPS, 0.5% yeast extract, 20 g/L of D-glucose, and antibiotics. The cultures were incubated at 30° C. in a humidified incubating shaker at 250 rpm until they reached an OD$_{600}$ of 0.2 to 0.3, at which point the production of β-farnesene in the host cells was induced by adding 40 uL of 1 M IPTG to the culture medium. At the time of induction, the cultures were overlain with 8 mL of an organic overlay to capture the β-farnesene. Samples were taken at various time points by transferring 100 uL samples of the upper organic overlay layer to a clean tube. The tube was centrifuged to separate out any remaining cells or media, and 10 uL of the organic overlay samples were transferred into 500 uL ethyl acetate spiked with beta- or trans-caryophyllene as an internal standard in clean glass GC vials. The mixtures were vortexed for 30 seconds, and then analyzed as described in Example 18. *Escherichia coli* host strain B653 produced approximately 7 mg/g DCW β-farnesene.

Example 21

This example describes the production of α-farnesene or β-farnesene in a *Saccharomyces cerevisiae* host strain.

Strain EPY300 was generated by removing the expression plasmid from *Saccharomyces cerevisiae* strain EPY224 (Ro et al. (2006) *Nature* 440: 940-943; PCT Patent Publication WO2007/005604) by culturing in rich medium. Strain EPY300 was then transformed with expression plasmids pRS425-FSA or pR425-FSB, yielding host strains Y166 and Y164, respectively.

Host cell transformants were selected on synthetic defined media, containing 2% glucose and all amino acids except leucine (SM-glu). The host strain EPY300 was auxotrophic for leucine biosynthesis (leu2), but expression plasmid pRS425-FSA or pRS425-FSB restores leucine prototrophy (LEU2). Single colonies were transferred to culture vials containing 5 mL of liquid SM-glu lacking leucine. The cultures were incubated by shaking at 30° C. until growth reaches stationary phase. The cells were stored at −80° C. in cryo-vials in 1 mL frozen aliquots made up of 400 μL 50% glycerol and 600 μL liquid culture.

Seed cultures were established by adding a stock aliquot to a 125 mL flask containing 25 mL SM-glu lacking leucine, and growing the cultures overnight. The seed cultures were used to inoculate at an initial OD$_{600}$ of approximately 0.05 250 mL baffled flasks containing 40 mL of synthetic defined media lacking leucine, 0.2% glucose, and 1.8% galactose. Cultures were incubated at 30° C. on a rotary shaker at 200 rpm. Because the presence of glucose in the media prevents induction of the Gal1 promoter by galactose, farnesene production was not induced until the cells use up the glucose in the media and switch to using galactose as their main carbon source. The cultures are overlain with 8 mL methyl oleate or isopropyl myristate. Samples were taken once every 24 hours by transferring 2-10 uL of the organic solvent layer to a clean glass vial containing 500 uL ethyl acetate containing a known concentration of beta- or trans-caryophyllene as an internal standard. In addition, 0.5 mL aliquots of the whole culture broth were added to a glass vials containing 1 mL ethyl acetate spiked with trans-caryophyllene as an internal standard. The whole culture broth samples were extracted in the ethyl acetate by vortexing the glass vials for 10 minutes, after which 600 uL of the ethyl acetate extraction was transferred to a clean glass vial.

Host strain Y166 produced approximately 9.8 mg/L of α-farnesene at 120 hours (averaged over 3 independent clones), and had a maximal specific productivity of approximately 3 mg/L/OD$_{600}$ (1 representative clone). Host strain Y164 produced approximately 56 mg/L of β-farnesene at 120 hours (averaged over 3 independent clones), and had a maximal specific productivity of approximately 20 mg/L/OD$_{600}$ (1 representative clone).

Example 22

This example describes the production of γ-terpinene, α-pinene, and terpinolene in *Escherichia coli* host strains.

Seed cultures of host strains for production of γ-terpinene (*E. coli* DH1-T1r [pMevT, pMevB-Gpps, pAM445]), α-pinene (*E. coli* DH1-T1r [pMevT, pMevB-Gpps, pAM443 or pAM442]) or terpinolene (*E. coli* DH1-T1r [pMevT, pMevB-Gpps, pAM444] were established by adding a stock aliquot of each strain to separate 125 mL flasks containing 25 mL M9-MOPS, 2% glucose, 0.5% yeast extract, and antibiotics as detailed in Table 1, and by growing the cultures overnight to late exponential phase.

The seed cultures were used to inoculate at an initial $OD_{600}$ of approximately 0.05, 250 mL flasks containing 40 mL M9-MOPS, 2% glucose, 0.5% yeast extract, and antibiotics. At time of inoculation, the cultures were also overlain with 4 mL hexadecane. Cultures were incubated at 30° C. on a rotary shaker at 200-250 rpm until they reached an $OD_{600}$ of approximately 0.2, at which point the production of the compound of interest in the host cells in the host cells was induced by adding 40 uL of 1 M IPTG. Samples were taken once per day for 96 hours by transferring 200 uL of the hexadecane layer to a 0.6 mL microfuge tube. For analysis, the hexadecane overlay was diluted 1:1 or 1:10 with ethyl acetate spiked with trans-caryophyllene as an internal standard in a 1.8 mL GC vial. In addition, 1 mL aliquots of the cultures were spun down, cell pellets were resuspended in 250 uL sterile water, and the cell suspensions were transferred to a glass vial containing 1 mL ethyl acetate spiked with trans-caryophyllene as an internal standard. The cell pellets were extracted in the ethyl acetate by vortexing the glass vials for 15 minutes, after which 500 uL of the ethyl acetate extraction was transferred to a clean glass vial.

The hexadecane/ethyl acetate samples and the ethyl acetate-extracted cell pellet samples were analyzed on an Agilent 6890N gas chromatograph equipped with an Agilent 5975 mass spectrometer (GC/MS) in full scan mode (50-500 m/z). To expedite run times, the temperature program and column matrix was modified to achieve optimal peak resolution and the shortest overall runtime. A 1 µL sample was split (a split ratio between 1:2 and 1:50 was selected based on sample concentration) and then separated using a HP-5MS column (Agilent Technologies, Inc., Palo Alto, Calif.) and helium carrier gas. The temperature program for the analysis was as follows: 75° C. hold for 3 minutes, increasing temperature at 20° C./minute to a temperature of 115° C., increasing temperature at 60° C./minute to a temperature of 300° C., and a hold at 300° C. for 0.5 minute. The various products, γ-terpinene, α-pinene, and terpinolene were observed at 5.4, 4.1, 5.4, and 5.9 minutes, respectively. Titers were calculated by comparing generated peak areas against a quantitative calibration curve of purified standards in trans-caryophyllene-spiked ethyl acetate.

Example 23

This example describes the production of linalool, limonene, β-pinene, β-phellandrene, carene, or sabinine in *Escherichia coli* host strains.

Seed cultures are established by adding a stock aliquot of each strain to separate 125 mL flasks containing 25 mL M9-MOPS, 0.5% yeast extract, 2% glucose, and antibiotics as detailed in Table 1, and by growing the cultures overnight.

The seed cultures are used to inoculate at an initial $OD_{600}$ of approximately 0.05, 250 mL baffled flasks containing 40 mL M9-MOPS, 0.5% yeast extract, 2% glucose, and antibiotics. Cultures are incubated at 30° C. on a rotary shaker at 250 rpm until they reach an $OD_{600}$ of approximately 0.2, at which point the production of the compound of interest in the host cells is induced by adding 40 ul of 1 M IPTG to the culture medium. The compound of interest is separated from the culture medium through solvent-solvent extraction, or by settling and decantation if the titer of the compound of interest is large enough to saturate the media and to form a second phase.

What is claimed is:

1. A method for producing an isoprenoid comprising:
(a) obtaining a plurality of bacterial or fungal host cells that comprise a heterologous nucleic acid encoding one or more enzymes of a mevalonate pathway for making isopentenyl pyrophosphate, wherein expression of the one or more enzymes is under control of at least one heterologous transcriptional regulator, wherein said mevalonate pathway comprises (i) an enzyme that condenses acetoacetyl-CoA with acetyl-CoA to form HMG-CoA; (ii) an enzyme that converts HMG-CoA to mevalonate; (iii) an enzyme that phosphorylates mevalonate to mevalonate 5-phosphate; (iv) an enzyme that converts mevalonate 5-phosphate to mevalonate 5-pyrophosphate; and (v) an enzyme that converts mevalonate 5-pyrophosphate to isopentenyl pyrophosphate; and
(b) culturing the bacterial or fungal host cells in a medium in which carbon source is limited so that the medium provides for about 75% or less of maximum specific growth rate for the bacterial or fungal host cells, wherein said maximum specific growth rate is a rate that would have been achieved by culturing the bacterial or fungal host cells under optimal temperature for growth of the bacterial or fungal host cells, and in a medium in which nutrients are present in excess.

2. The method of claim 1 wherein the at least one heterologous transcriptional regulator is inducible.

3. The method of claim 1 wherein the mevalonate pathway enzymes are under control of a single transcriptional regulator.

4. The method of claim 1 wherein the mevalonate pathway enzymes are under control of a multiple transcriptional regulator.

5. The method of claim 1 wherein the host cells comprise a plurality of heterologous nucleic acids encoding all of the enzymes of a mevalonate pathway.

6. The method of claim 1 wherein the bacterial cells are *E coli*.

7. The method of claim 1 wherein the heterologous nuckic acid comprises a nucleic acid sequence encoding a mevaloante pathway enzyme from a fungus having an endogenous mevalonate pathway.

8. The method of claim 1 wherein the host cells are *S. cerevisiae*.

9. The method of claim 1 wherein the heterologous nucleic acid comprises a nucleic acid sequence encoding a mevalonate pathway enzyme from a bacterium having an endogenous mevalonate pathway.

10. The method of claim 9 wherein the bacterium is of the genus selected from *Enterococcus, Pseudomonas*, and *Staphyloccoccus*.

11. The method of claim 1 wherein the heterologous nucleic acid comprises a nucleic acid sequence encoding a mevaloante pathway enzyme selected from acetyl-CoA thiolase, HMG-CoA synthase, HMG-CoA reductase, and mevalonate kinase.

12. The method of claim 1 wherein the heterologous nucleic acid comprises a nucleic acid sequence encoding a Class II HMG reductase.

13. The method of claim 1 wherein the host cells are cultured in the medium wherein nutrient and temperature both are maintained at a level below that which would provide for the maximum specific growth rate for the host cells.

14. The method of claim 1 wherein the temperature of the medium is at least 2-20° C. below the optimal temperature.

15. The method of claim 14 wherein the host cells are cultured at a temperature at least 5° C. below the optimal temperature.

16. The method of claim 14 wherein the temperature of the medium is at least 10° C. below the optimal temperature.

17. The method of claim 1 wherein the medium will provide for about 60% or less of the maximum specific growth rate.

18. The method of claim 1 wherein the medium will provide for about 50% or less of the maximum specific growth rate.

19. The method of claim 1 wherein the medium will provide for about 40% or less of the maximum specific growth rate.

20. The method of claim 1 wherein the medium will provide for about 25% or less of the maximum specific growth rate.

21. The method of claim 1 wherein the medium will provide for about 75%-10% of the maximum specific growth rate.

22. The method of claim 1 wherein the medium is nitrogen-restricted.

23. The method of claim 1 wherein the isoprenoid is produced in an amount greater than about 10 grams per liter of medium.

24. The method of claim 1 wherein the isoprenoid is produced in an amount greater than about 50 mg per gram of dry cell weight.

25. The method of any one of claims 23 or 24 wherein the amount of isoprenoid is produced in less tan about 150 hours.

26. The method of claim 23 or 24 wherein the amount of isoprenoid is produced in less than about 96 hours.

27. The method of claim 23 or 24 wherein the amount of isoprenoid is produced in less than about 72 hours.

28. The method of claim 1 wherein the isoprenoid is selected from the group consisting of a hemiterpene, monoterpene, diterpene, triterpene, tetraterpene, sesquiterpene, and polyterpene.

29. The method of claim 1 wherein the isoprenoid is a sesquiterpene.

30. The method of claim 1 wherein the isoprenoid is a $C_5$-$C_{20}$ isoprenoid.

31. The method of claim 1 wherein the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpindene and valencene.

32. The method of claim 1, wherein the nutrients comprise carbon source and nitrogen source.

33. The method of claim 29 wherein the sescjuiterpene is α-farnesene.

34. The method of claim 29 wherein the sesquiterpene is β-farnesene.

35. The method of claim 29 wherein the sesquiterpene is amorphadiene.

36. The method of claim 29 wherein the sesquiterpene is farnesol.

37. The method of claim 29 wherein the sesquiterpene is nerolidol.

38. The method of claim 30 wherein the sesquiterpene is patchoulol.

39. The method of claim 30 wherein the sesquiterpene is valencene.

40. The method of claim 1, wherein said one or more enzymes is a bacterial enzyme.

41. The method of claim 1, wherein said one or more enzymes is a fbngal enzyme.

* * * * *

UNITED STATES PATENT AND TRADEMARK OFFICE
CERTIFICATE OF CORRECTION

PATENT NO. : 7,659,097 B2
APPLICATION NO. : 11/754235
DATED : February 9, 2010
INVENTOR(S) : Neil Stephen Renninger et al.

It is certified that error appears in the above-identified patent and that said Letters Patent is hereby corrected as shown below:

Column 135, line 53, delete the word "nuckic" and replace with --nucleic--

Column 135, line 55, delete the word "mevaloante" and replace with --mevalonate--

Column 136, line 15, delete the word "mevaloante" and replace with --mevalonate--

Column 136, line 57, delete the word "tan" and replace with --than--

Column 137, line 5, delete the word "a-famesene" and replace with --a-farnesene--

Column 137, line 8, delete the word "terpindene" and replace with --terpinolene--

Column 138, line 14, delete the word "fbngal" and replace with --fungal--

Signed and Sealed this

Thirteenth Day of April, 2010

David J. Kappos
*Director of the United States Patent and Trademark Office*